US011725035B2

(12) United States Patent
Jakobsen et al.

(10) Patent No.: US 11,725,035 B2
(45) Date of Patent: Aug. 15, 2023

(54) METHODS OF TREATING A DISORDER ASSOCIATED WITH WITH INSUFFICIENT STIMULATOR OF INTERFERON GENES (STING) ACTIVITY

(71) Applicant: STipe Therapeutics ApS, Aarhus C (DK)

(72) Inventors: Martin Roelsgaard Jakobsen, Risskov (DK); Søren Riis Paludan, Åbyhøj (DK); Kasper Lisager Jønsson, Aarhus C (DK)

(73) Assignee: STipe Therapeutics ApS, Aarhus C (DK)

( * ) Notice: Subject to any disclaimer, the term of this patent is extended or adjusted under 35 U.S.C. 154(b) by 269 days.

(21) Appl. No.: 16/323,949

(22) PCT Filed: Aug. 9, 2017

(86) PCT No.: PCT/EP2017/070208
§ 371 (c)(1),
(2) Date: Feb. 7, 2019

(87) PCT Pub. No.: WO2018/029256
PCT Pub. Date: Feb. 15, 2018

(65) Prior Publication Data
US 2019/0292236 A1     Sep. 26, 2019

(30) Foreign Application Priority Data

Aug. 9, 2016 (DK) .............................. PA201670606
Feb. 8, 2017 (DK) .............................. PA201770079

(51) Int. Cl.
| | |
|---|---|
| *C07K 14/555* | (2006.01) |
| *A61P 35/00* | (2006.01) |
| *A61K 38/21* | (2006.01) |
| *C07K 14/52* | (2006.01) |
| *A61K 38/17* | (2006.01) |

(52) U.S. Cl.
CPC ........ *C07K 14/555* (2013.01); *A61K 38/1709* (2013.01); *A61K 38/21* (2013.01); *A61P 35/00* (2018.01); *C07K 14/52* (2013.01)

(58) Field of Classification Search
CPC ........ C07K 14/555; A61K 38/21; A61P 35/00
See application file for complete search history.

(56) References Cited

U.S. PATENT DOCUMENTS

| | | |
|---|---|---|
| 8,334,101 B2 | 12/2012 | Latz et al. |
| 8,603,966 B2 | 12/2013 | Wimley et al. |
| 9,163,071 B2* | 10/2015 | Harton ................... A61P 17/04 |
| 2013/0039933 A1* | 2/2013 | Barber ................... A61P 31/12 |
| | | 424/185.1 |
| 2013/0345143 A1 | 12/2013 | White et al. |
| 2015/0056224 A1 | 2/2015 | Dubensky et al. |
| 2016/0074507 A1 | 3/2016 | Manel et al. |
| 2016/0175387 A1 | 6/2016 | Bahrami et al. |
| 2020/0399335 A1 | 12/2020 | Jakobsen et al. |
| 2021/0030870 A1 | 2/2021 | Prabakaran et al. |

FOREIGN PATENT DOCUMENTS

| | | |
|---|---|---|
| EP | 1033401 A2 | 9/2000 |
| EP | 3263704 A1 | 1/2018 |
| WO | WO 2000/029427 A1 | 5/2000 |
| WO | WO 2007/009894 A1 | 1/2007 |
| WO | WO 2010/017248 A2 | 2/2010 |
| WO | WO-2011/138251 A1 | 11/2011 |
| WO | WO 2013/022991 A2 | 2/2013 |
| WO | WO-2015/095609 A1 | 6/2015 |
| WO | WO-2015/123493 A2 | 8/2015 |
| WO | WO 2015/179436 A1 | 11/2015 |
| WO | WO 2018/029256 A1 | 2/2018 |
| WO | WO 2018/206577 A1 | 11/2018 |
| WO | WO 2019/154901 A1 | 8/2019 |

OTHER PUBLICATIONS

Surpris et al., 2016, Current Opinion in Micrebiology, vol. 32, pp. 144-150, Pub Date Jul. 11, 2016 (Year: 2016).*
Kolchanov, 1988, Journal of Molecular Evolution, vol. 27, pp. 154-162. (Year: 1988).*
Pasquo, 2012, PLoS ONE, vol. 7, Issue 2, e32555 (Year: 2012).*
Li Di, The AAPS Journal, vol. 17, No. 1, Jan. 2015.*
Kumai et al. Current Opinion in Immunology, 2017, 47:57-63.*
Ablasser, A. et al., Cell intrinsic immunity spreads to bystander cells via the intercellular transfer of cGAMP, Nature, 503(7477): 530-534, Nov. 28, 2013.
Ahn, J. et al., Intrinsic Self-DNA Triggers Inflammatory Disease Dependent on STING, the Journal of Immunology, 193:4634-4642, Sep. 26, 2014.
Almine, J. et al., IFI16 and cGAS cooperate in the activation of STING during DNA sensing in human keratinocytes, Nature Communications, 8: 14392, Feb. 13, 2017.
Bridgeman, A. et al., Viruses transfer the antiviral second messenger cGAMP between cells, Science, 349(6253):1228-32, Sep. 11, 2015.
Cao, T. et al, Up-regulation of interferon inducible protein 16 contributes to psoriasis by modulating chemokine production in keratinocytes, Scientific Reports, 6:25381, May 3, 2016.

(Continued)

*Primary Examiner* — Robert S Landsman

(74) *Attorney, Agent, or Firm* — Wolf, Greenfield & Sacks, P.C.

(57) ABSTRACT

Compounds capable of mimicking the pyrin-domain of IFl16 is provided together with compounds capable of binding to the pyrin-domain of IFl16 or a fragment thereof as well as their uses in medicine. Specifically, the compounds are provided for use in the treatment of disorders associated with STING activity, including cancer and immuno-deficient or auto-immune disorders.

8 Claims, 42 Drawing Sheets

Specification includes a Sequence Listing.

(56) References Cited

OTHER PUBLICATIONS

Christensen, M. et al., Viral evasion of DNA-stimulated innate immune responses, Cellular & Molecular Immunglogy, 13; 1-10, Mar. 14, 2016.
Diner, B. et al., The functional interactome of PYHIN immune regulators reveals IFIX is a sensor of viral DNA, Mol Syst Biol, 11(787): 1 -22, Feb. 9, 2015.
Diner, B. et al., Viral DNA Sensors IFI16 and Cyclic GMP-AMP Synthase Possess Distinct Functions in Regulating Viral Gene Expression, Immune Defenses, and Apoptotic Responses during Herpesvirus Infection, mBio, 7(6):e01553-16, Nov. 15, 2016.
Dobbs, N.et al., STING activation by translocation from the ER is associated with infection and autoinflammatory disease, Cell Host Microbe, 18(2): 157-168, Aug. 12, 2015.
Gao, D. et al., Activation of cyclic GMP-AMP synthase by self-DNA causes autoimmune diseases, PNAS, pp. E5699-E5705, Sep. 14, 2015.
Gentili, M. et al., Transmission of innate immune signaling by packaging of cGAMP in viral particles, Science, 349(6253): 1232-1236, Sep. 11, 2015.
Hamers-Casterman, C. et al., Naturally occurring antibodies devoid of light chains, Nature; 363: 446-448, Jun. 3, 1993.
Hansen, K. et al., Listeria monocytogenes induces IFN expression through an IFI16-, cGAS- and STING-dependent pathway. The EMBO Journal. 33(15): 1654-1666, Jun. 26, 2014.
Hasan, M. et al; Therapeutic potential of targeting TBK1 in autoimmune diseases and interferonopathies; Pharmacol Res., 111: 336-342, Sep. 2016.
Holm, C. et al., Influenza A virus targets a cGAS-independent STING pathway that controls enveloped RNA viruses, Nature Communications, 7:10680, pp. 1-9, Feb. 19, 2016.
Jakobsen, M. et al., Correction for IFI16 senses DNA forms of the lentiviral replication cycle and controls HIV-1 replication, PNAS, 110(48): 19651-19652, Nov. 26. 2013.
Jakobsen, M. R. et al., IFI16 senses DNA forms of the lentiviral replication cycle and controls HIV-1 replication, PNAS, pp. E4571-E4580, Oct. 23, 2013.
Jin, T. et al., Structures of the HIN Domain:DNA Complexes Reveal Ligand Binding and Activation Mechanisms of the AIM Inflammasome and IFI16 Receptor, Immunity, 36(4): 561-571, Apr. 20, 2012.
Jønsson, K. et al., IFI16 is required for DNA sensing in human macrophages by promoting production and function of cGAMP, Nature Communications, 8:14391, Feb. 10, 2017.
Klarquist, J. et al., STING-mediated DNA sensing promotes antitumor and autoimmune responses to dying ceils, J Immunol., 193(12): 6124-6134, Dec. 15, 2014.
Lemos, H. et al., STING promotes the growth of tumors characterized by low antigenicity via IDO activation, Cancer Res., 76(8): 2076-2081, Apr. 15, 2016.
Li, T. et al., Human Cytomegalovirus Tegument Protein pUL83 Inhibits IFI16-Mediated DNA Sensing for Immune Evasion, Cell Host Microbe, 14(5): 591-599, Nov. 13. 2013.
Liu, S. et al., Phosphorylation of innate immune adaptor proteins MAVS, STING, and TRIF induces IRF3 activation, Science, 347(6227): aaa2630-1-aaa2630-14, Jan. 29, 2015.
Nissen, et al., Innate DNA sensing is impaired in HIV patients and IFI16 expression correlates with chronic immune activation, Clinical and Experimental Immunology, 177(1): 295-309, Jul. 2014.
Orzalli, M. et al., cGAS-mediated stabilization of IFI16 promotes innate signaling during herpes simplex virus infection, Proceedings National Academy of Sciences (PNAS), 112(14): E1773-E1781, Mar. 23, 2015.
Unterholzner, L. et al., IFI16 is an innate immune sensor for intracellular innate immune sensor for intracellular DNA, Nature Immunology, 11(11): 997-1004, Oct. 3, 2010.
Van De Weijer, M. et al., A high-coverage shRNA screen identifies TMEM129 as an E3 ligase involved in ER-associated protein degradation, Nature Communications, 5:3832, May 8, 2014.

Wu, X. et al, Molecular evolutionary and structural analysis of the cytosolic DNA sensor cGAS and STING, Nuclelc Acids Research, 42(13): 8243-8257. Jun. 30, 2014.
Zhao H. et al; The roles of interferon-inducible p200 family members IFI16 and p204 in innate immune responses, cell differentiation and proliferation; Genes & Diseases, 2(1):46-56, Nov. 1, 2014.
Khare et al., The PYRIN domain-only protein POP3 inhibits ALR inflammasomes and regulates responses to infection with DNA viruses. Nat Immunol. Apr. 2014;15(4):343-53. doi: 10.1038/ni.2829. Epub Feb. 16, 2014.
Bhatelia et al., MITA modulated autophagy flux promotes cell death in breast cancer cells. Cell Signal. Jul. 2017;35:73-83. doi: 10.1016/j.cellsig.2017.03.024. Epub Mar. 31, 2017.
Konno et al., Cyclic dinucleotides trigger ULK1 (ATG1) phosphorylation of STING to prevent sustained innate immune signaling. Cell. Oct. 24, 2013;155(3):688-98. doi: 10.1016/j.cell.2013.09.049. Epub Oct. 10, 2013.
Liu et al., Sequestosome 1/p62: a multi-domain protein with multi-faceted functions. Front Biol. 2012;7(3):189-201.
Paludan et al., Immune sensing of DNA. Immunity. May 23, 2013;38(5):870-80. doi: 10.1016/j.immuni.2013.05.004.
Prabakaran et al., Attenuation of cGAS-STING signaling is mediated by a p62/SQSTM1-dependent autophagy pathway activated by TBK1. EMBO J. Apr. 13, 2018;37(8):e97858. doi: 10.15252/embj.201797858. Epub Mar. 1, 2018.
Veeranki et al., IFI16 protein mediates the anti-inflammatory actions of the type-I interferons through suppression of activation of caspase-1 by inflammasomes. PLoS One. 2011;6(10):e27040. doi: 10.1371/journal.pone.0027040. Epub Oct. 28, 2011.
U.S. Appl. No. 16/968,398, filed Aug. 7, 2020, Jakobsen et al..
U.S. Appl. No. 16/967,703, filed Aug. 5, 2020, Prabakaran et al..
PCT/EP2019/052886, dated Mar. 13, 2019, International Search Report and Written Opinion.
PCT/EP2019/052886, dated Aug. 11, 2020, International Preliminary Report on Patentability.
PCT/EP2019/052983, dated Mar. 8, 2019, International Search Report and Written Opinion.
PCT/EP2019/052983, dated Oct. 16, 2020, International Preliminary Report on Patentability.
[No Author Listed], Multiple Sequence Alignment Clustal Omega Tool. EMBL-EBI. Cambridgeshire, UK. Accessed Nov. 10, 2022 from <https://web.archive.org/web/20160608042153/https://www.ebi.ac.uk/Tools/msa/clustalo/>, as available Jun. 8, 2016. 1 page.
Derossi et al., The third helix of the Antennapedia homeodomain translocates through biological membranes. J Biol Chem. Apr. 8, 1994;269(14):10444-50.
Fischer et al., Structure-activity relationship of truncated and substituted analogues of the intracellular delivery vector Penetratin. J Pept Res. Feb. 2000;55(2):163-72. doi: 10.1034/j.1399-3011.2000.00163.x.
Konno et al., The STING controlled cytosolic-DNA activated innate immune pathway and microbial disease. Microbes Infect. Dec. 2014;16(12):998-1001. doi: 10.1016/j.micinf.2014.10.002. Epub Oct. 18, 2014. Author Manuscript. 7 pages.
Lättig-Tünnemann et al., Backbone rigidity and static presentation of guanidinium groups increases cellular uptake of arginine-rich cell-penetrating peptides. Nat Commun. Aug. 30, 2011;2:453. doi: 10.1038/ncomms1459.
Li et al., Antitumor Activity of cGAMP via Stimulation of cGAS-cGAMP-STING-IRF3 Mediated Innate Immune Response. Sci Rep. Jan. 12, 2016;6:19049. doi: 10.1038/srep19049.
Ohkuri et al., STING contributes to antiglioma immunity via triggering type I IFN signals in the tumor microenvironment. Cancer Immunol Res. Dec. 2014;2(12):1199-208. doi: 10.1158/2326-6066.CIR-14-0099. Epub Oct. 9, 2014. Author Manuscript. 20 pages.
Prabakaran et al., A STING antagonist modulating the interaction with STIM1 blocks ER-to-Golgi trafficking and inhibits lupus pathology. EBioMedicine. Apr. 2021;66:103314. doi: 10.1016/j.ebiom.2021.103314. Epub Apr. 2, 2021.
Ruzza et al., Antennapedia/HS1 chimeric phosphotyrosyl peptide: conformational properties, binding capability to c-Fgr SH2 domain

(56) References Cited

OTHER PUBLICATIONS and cell permeability. Biopolymers. 2001;60(4):290-306. doi: 10.1002/1097-0282(2001)60:4<290::AID-BIP9991>3.0.CO;2-M.

Song et al., Decreased expression of STING predicts poor prognosis in patients with gastric cancer. Sci Rep. Feb. 8, 2017;7:39858. doi: 10.1038/srep39858.

Torchilin et al., TAT peptide on the surface of liposomes affords their efficient intracellular delivery even at low temperature and in the presence of metabolic inhibitors. Proc Natl Acad Sci U S A. Jul. 17, 2001;98(15):8786-91. doi: 10.1073/pnas.151247498. Epub Jul. 3, 2001.

Xia et al., Deregulation of STING Signaling in Colorectal Carcinoma Constrains DNA Damage Responses and Correlates With Tumorigenesis. Cell Rep. Jan. 12, 2016;14(2):282-97. doi: 10.1016/j.celrep.2015.12.029. Epub Dec. 31, 2015. Supplemental Material, 12 pages.

\* cited by examiner

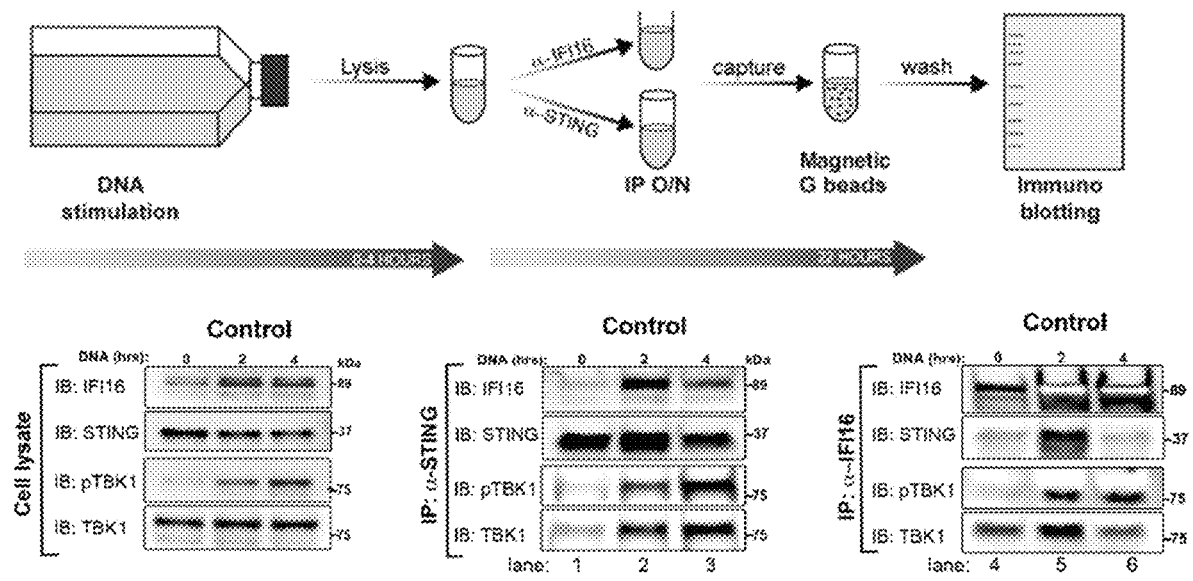
FIG. 4A
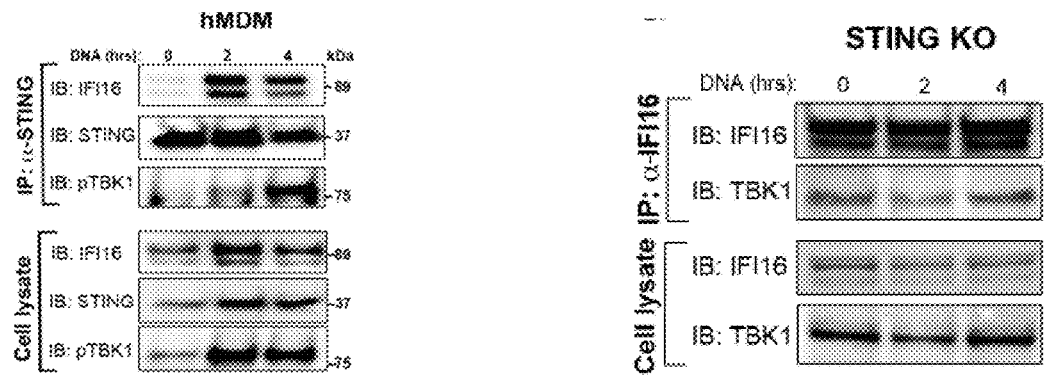
FIG. 4B
FIG. 4C
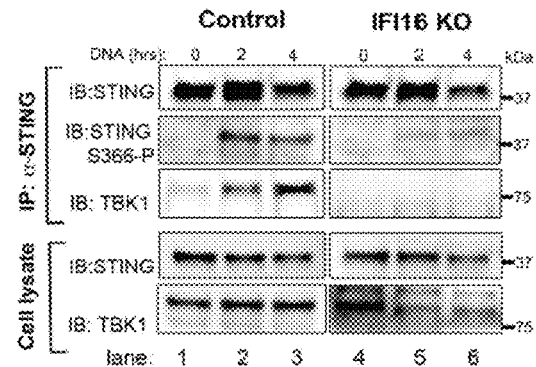
FIG. 4D

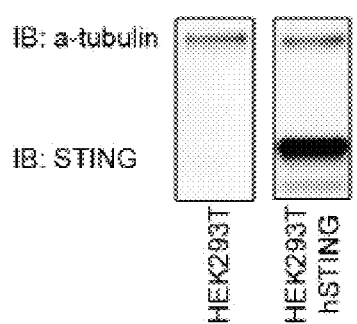
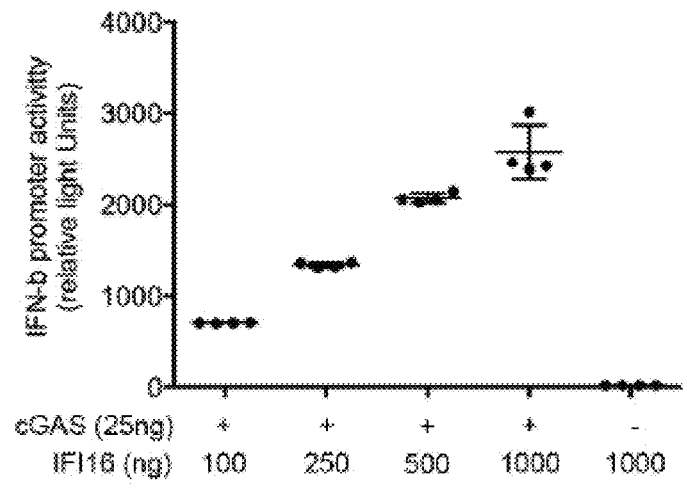
FIG. 5F
FIG. 5G
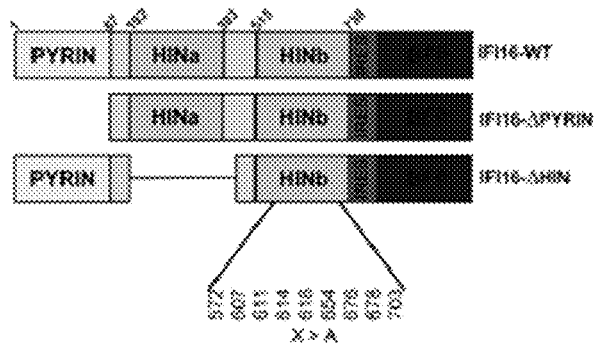
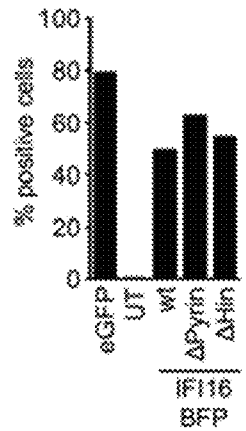
FIG. 5H

FIG. 9

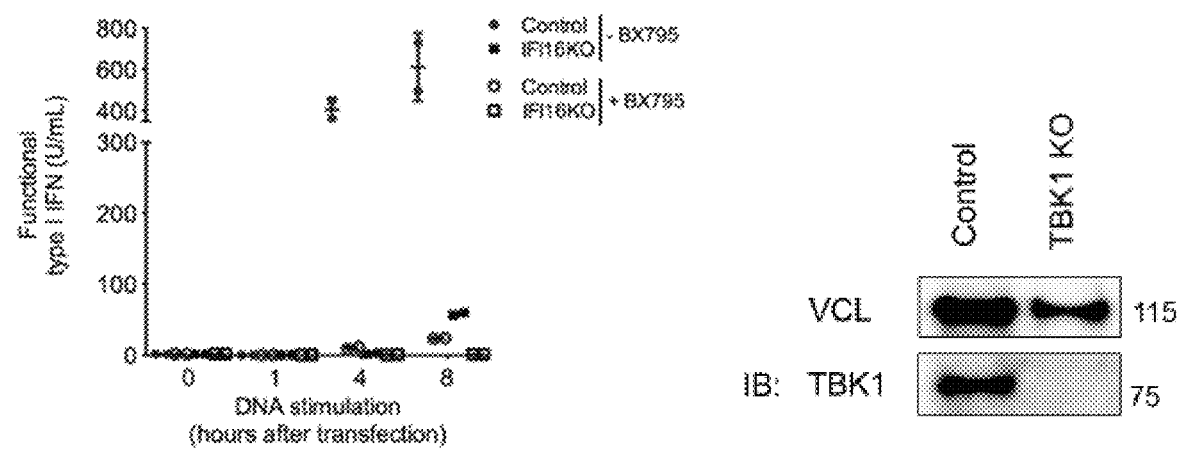
FIG. 11E
FIG. 11F
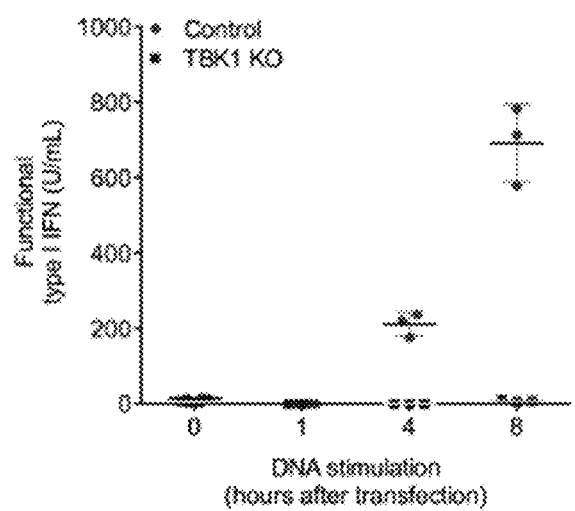
FIG. 11G

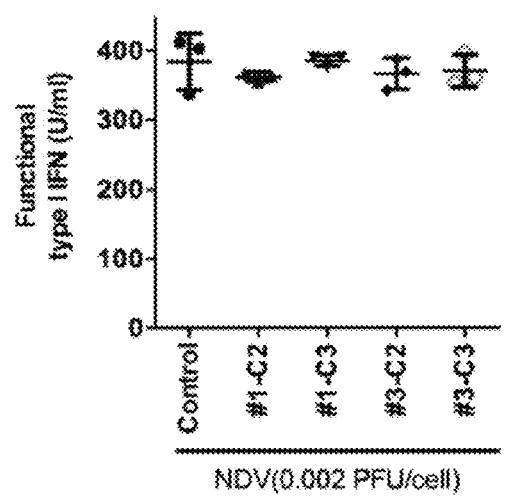
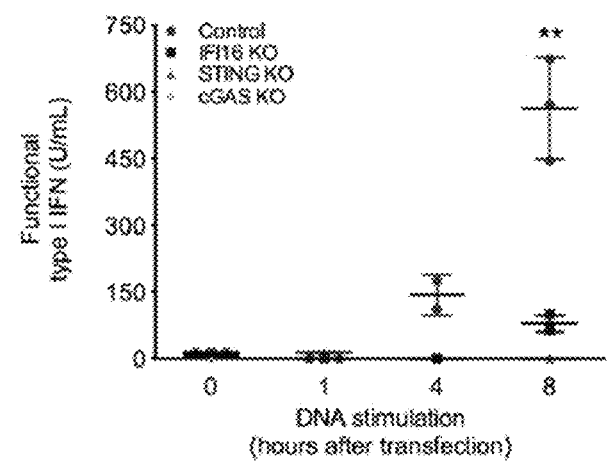
FIG. 13E
FIG. 13F
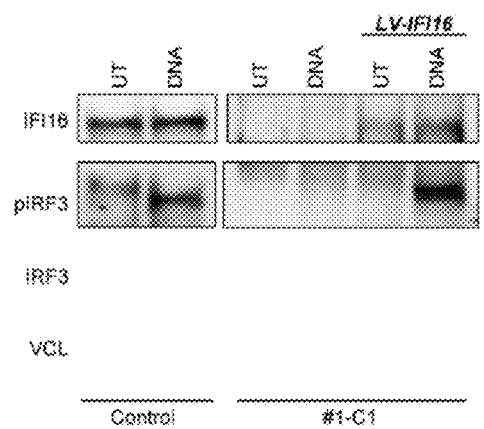
FIG. 13G
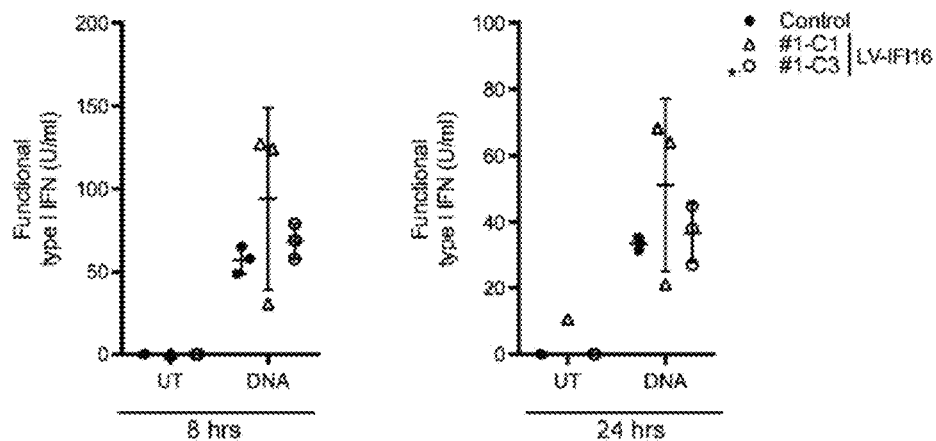
FIG. 13H

CONTROL

STING KO

```
                        SEQUENCE LISTING

<160> NUMBER OF SEQ ID NOS: 39

<210> SEQ ID NO 1
<211> LENGTH: 86
<212> TYPE: PRT
<213> ORGANISM: Homo sapiens

<400> SEQUENCE: 1

Lys Lys Tyr Lys Asn Ile Val Leu Leu Lys Gly Leu Glu Val Ile Asn
1               5                   10                  15

Asp Tyr His Phe Arg Met Val Lys Ser Leu Leu Ser Asn Asp Leu Lys
            20                  25                  30

Leu Asn Leu Lys Met Arg Glu Glu Tyr Asp Lys Ile Gln Ile Ala Asp
        35                  40                  45

Leu Met Glu Glu Lys Phe Arg Gly Asp Ala Gly Leu Gly Lys Leu Ile
    50                  55                  60

Lys Ile Phe Glu Asp Ile Pro Thr Leu Glu Asp Leu Ala Glu Thr Leu
65                  70                  75                  80

Lys Lys Glu Lys Leu Lys
                85

<210> SEQ ID NO 2
<211> LENGTH: 789
<212> TYPE: PRT
<213> ORGANISM: Homo sapiens

<400> SEQUENCE: 2

Met Ser Val Lys Met Gly Lys Lys Tyr Lys Asn Ile Val Leu Leu Lys
1               5                   10                  15

Gly Leu Glu Val Ile Asn Asp Tyr His Phe Arg Met Val Lys Ser Leu
            20                  25                  30

Leu Ser Asn Asp Leu Lys Leu Asn Leu Lys Met Arg Glu Glu Tyr Asp
        35                  40                  45

Lys Ile Gln Ile Ala Asp Leu Met Glu Glu Lys Phe Arg Gly Asp Ala
    50                  55                  60

Gly Leu Gly Lys Leu Ile Lys Ile Phe Glu Asp Ile Pro Thr Leu Glu
65                  70                  75                  80

Asp Leu Ala Glu Thr Leu Lys Lys Glu Lys Leu Lys Val Lys Gly Pro
            85                  90                  95

Ala Leu Ser Arg Lys Arg Lys Lys Glu Val Asp Ala Thr Ser Pro Ala
            100                 105                 110

Pro Ser Thr Ser Ser Thr Val Lys Thr Glu Gly Ala Glu Ala Thr Pro
            115                 120                 125

Gly Ala Gln Lys Arg Lys Lys Ser Thr Lys Glu Lys Ala Gly Pro Lys
        130                 135                 140

Gly Ser Lys Val Ser Glu Glu Gln Thr Gln Pro Pro Ser Pro Ala Gly
145                 150                 155                 160

Ala Gly Met Ser Thr Ala Met Gly Arg Ser Pro Ser Pro Lys Thr Ser
                165                 170                 175
```

```
Leu Ser Ala Pro Pro Asn Ser Ser Thr Glu Asn Pro Lys Thr Val
            180                 185                 190

Ala Lys Cys Gln Val Thr Pro Arg Arg Asn Val Leu Gln Lys Arg Pro
        195                 200                 205

Val Ile Val Lys Val Leu Ser Thr Thr Lys Pro Phe Glu Tyr Glu Thr
    210                 215                 220

Pro Glu Met Glu Lys Lys Ile Met Phe His Ala Thr Val Ala Thr Gln
225                 230                 235                 240

Thr Gln Phe Phe His Val Lys Val Leu Asn Thr Ser Leu Lys Glu Lys
                245                 250                 255

Phe Asn Gly Lys Lys Ile Ile Ile Ser Asp Tyr Leu Glu Tyr Asp
                260                 265                 270

Ser Leu Leu Glu Val Asn Glu Glu Ser Thr Val Ser Glu Ala Gly Pro
        275                 280                 285

Asn Gln Thr Phe Glu Val Pro Asn Lys Ile Ile Asn Arg Ala Lys Glu
    290                 295                 300

Thr Leu Lys Ile Asp Ile Leu His Lys Gln Ala Ser Gly Asn Ile Val
305                 310                 315                 320

Tyr Gly Val Phe Met Leu His Lys Lys Thr Val Asn Gln Lys Thr Thr
                325                 330                 335

Ile Tyr Glu Ile Gln Asp Asp Arg Gly Lys Met Asp Val Val Gly Thr
                340                 345                 350

Gly Gln Cys His Asn Ile Pro Cys Glu Glu Gly Asp Lys Leu Gln Leu
            355                 360                 365

Phe Cys Phe Arg Leu Arg Lys Lys Asn Gln Met Ser Lys Leu Ile Ser
        370                 375                 380

Glu Met His Ser Phe Ile Gln Ile Lys Lys Lys Thr Asn Pro Arg Asn
385                 390                 395                 400

Asn Asp Pro Lys Ser Met Lys Leu Pro Gln Glu Gln Arg Gln Leu Pro
                405                 410                 415

Tyr Pro Ser Glu Ala Ser Thr Thr Phe Pro Glu Ser His Leu Arg Thr
            420                 425                 430

Pro Gln Met Pro Pro Thr Thr Pro Ser Ser Phe Phe Thr Lys Lys
        435                 440                 445

Ser Glu Asp Thr Ile Ser Lys Met Asn Asp Phe Met Arg Met Gln Ile
    450                 455                 460

Leu Lys Glu Gly Ser His Phe Pro Gly Pro Phe Met Thr Ser Ile Gly
465                 470                 475                 480

Pro Ala Glu Ser His Pro His Thr Pro Gln Met Pro Pro Ser Thr Pro
                485                 490                 495

Ser Ser Ser Phe Leu Thr Thr Lys Ser Glu Asp Thr Ile Ser Lys Met
            500                 505                 510

Asn Asp Phe Met Arg Met Gln Ile Leu Lys Glu Gly Ser His Phe Pro
        515                 520                 525

Gly Pro Phe Met Thr Ser Ile Gly Pro Ala Glu Ser His Pro His Thr
        530                 535                 540

Pro Gln Met Pro Pro Ser Thr Pro Ser Ser Phe Leu Thr Thr Leu
545                 550                 555                 560

Lys Pro Arg Leu Lys Thr Glu Pro Glu Glu Val Ser Ile Glu Asp Ser
                565                 570                 575

Ala Gln Ser Asp Leu Lys Glu Val Met Val Leu Asn Ala Thr Glu Ser
            580                 585                 590
```

```
Phe Val Tyr Glu Pro Lys Glu Gln Lys Lys Met Phe His Ala Thr Val
            595                 600                 605
Ala Thr Glu Asn Glu Val Phe Arg Val Lys Val Phe Asn Ile Asp Leu
    610                 615                 620
Lys Glu Lys Phe Thr Pro Lys Lys Ile Ile Ala Ile Ala Asn Tyr Val
625                 630                 635                 640
Cys Arg Asn Gly Phe Leu Glu Val Tyr Pro Phe Thr Leu Val Ala Asp
                645                 650                 655
Val Asn Ala Asp Arg Asn Met Glu Ile Pro Lys Gly Leu Ile Arg Ser
            660                 665                 670
Ala Ser Val Thr Pro Lys Ile Asn Gln Leu Cys Ser Gln Thr Lys Gly
    675                 680                 685
Ser Phe Val Asn Gly Val Phe Glu Val His Lys Lys Asn Val Arg Gly
690                 695                 700
Glu Phe Thr Tyr Tyr Glu Ile Gln Asp Asn Thr Gly Lys Met Glu Val
705                 710                 715                 720
Val Val His Gly Arg Leu Thr Thr Ile Asn Cys Glu Glu Gly Asp Lys
                725                 730                 735
Leu Lys Leu Thr Cys Phe Glu Leu Ala Pro Lys Ser Gly Asn Thr Gly
            740                 745                 750
Glu Leu Arg Ser Val Ile His Ser His Ile Lys Val Ile Lys Thr Arg
    755                 760                 765
Lys Asn Lys Lys Asp Ile Leu Asn Pro Asp Ser Ser Met Glu Thr Ser
770                 775                 780
Pro Asp Phe Phe Phe
785

<210> SEQ ID NO 3
<211> LENGTH: 729
<212> TYPE: PRT
<213> ORGANISM: Homo sapiens

<400> SEQUENCE: 3

Met Gln Ser Thr Ser Asn His Leu Trp Leu Leu Ser Asp Ile Leu Gly
1               5                   10                  15
Gln Gly Ala Thr Ala Asn Val Phe Arg Gly Arg His Lys Lys Thr Gly
            20                  25                  30
Asp Leu Phe Ala Ile Lys Val Phe Asn Asn Ile Ser Phe Leu Arg Pro
        35                  40                  45
Val Asp Val Gln Met Arg Glu Phe Glu Val Leu Lys Lys Leu Asn His
    50                  55                  60
Lys Asn Ile Val Lys Leu Phe Ala Ile Glu Glu Thr Thr Thr Arg
65                  70                  75                  80
His Lys Val Leu Ile Met Glu Phe Cys Pro Cys Gly Ser Leu Tyr Thr
                85                  90                  95
Val Leu Glu Glu Pro Ser Asn Ala Tyr Gly Leu Pro Glu Ser Glu Phe
            100                 105                 110
Leu Ile Val Leu Arg Asp Val Val Gly Gly Met Asn His Leu Arg Glu
        115                 120                 125
Asn Gly Ile Val His Arg Asp Ile Lys Pro Gly Asn Ile Met Arg Val
    130                 135                 140
Ile Gly Glu Asp Gly Gln Ser Val Tyr Lys Leu Thr Asp Phe Gly Ala
145                 150                 155                 160
Ala Arg Glu Leu Glu Asp Asp Glu Gln Phe Val Ser Leu Tyr Gly Thr
                165                 170                 175
```

```
Glu Glu Tyr Leu His Pro Asp Met Tyr Glu Arg Ala Val Leu Arg Lys
            180                 185                 190

Asp His Gln Lys Lys Tyr Gly Ala Thr Val Asp Leu Trp Ser Ile Gly
        195                 200                 205

Val Thr Phe Tyr His Ala Ala Thr Gly Ser Leu Pro Phe Arg Pro Phe
        210                 215                 220

Glu Gly Pro Arg Arg Asn Lys Glu Val Met Tyr Lys Ile Ile Thr Gly
225                 230                 235                 240

Lys Pro Ser Gly Ala Ile Ser Gly Val Gln Lys Ala Glu Asn Gly Pro
                245                 250                 255

Ile Asp Trp Ser Gly Asp Met Pro Val Ser Cys Ser Leu Ser Arg Gly
        260                 265                 270

Leu Gln Val Leu Leu Thr Pro Val Leu Ala Asn Ile Leu Glu Ala Asp
        275                 280                 285

Gln Glu Lys Cys Trp Gly Phe Asp Gln Phe Phe Ala Glu Thr Ser Asp
        290                 295                 300

Ile Leu His Arg Met Val Ile His Val Phe Ser Leu Gln Gln Met Thr
305                 310                 315                 320

Ala His Lys Ile Tyr Ile His Ser Tyr Asn Thr Ala Thr Ile Phe His
                325                 330                 335

Glu Leu Val Tyr Lys Gln Thr Lys Ile Ile Ser Ser Asn Gln Glu Leu
        340                 345                 350

Ile Tyr Glu Gly Arg Arg Leu Val Leu Glu Pro Gly Arg Leu Ala Gln
        355                 360                 365

His Phe Pro Lys Thr Thr Glu Glu Asn Pro Ile Phe Val Val Ser Arg
        370                 375                 380

Glu Pro Leu Asn Thr Ile Gly Leu Ile Tyr Glu Lys Ile Ser Leu Pro
385                 390                 395                 400

Lys Val His Pro Arg Tyr Asp Leu Asp Gly Asp Ala Ser Met Ala Lys
                405                 410                 415

Ala Ile Thr Gly Val Val Cys Tyr Ala Cys Arg Ile Ala Ser Thr Leu
                420                 425                 430

Leu Leu Tyr Gln Glu Leu Met Arg Lys Gly Ile Arg Trp Leu Ile Glu
        435                 440                 445

Leu Ile Lys Asp Asp Tyr Asn Glu Thr Val His Lys Lys Thr Glu Val
450                 455                 460

Val Ile Thr Leu Asp Phe Cys Ile Arg Asn Ile Glu Lys Thr Val Lys
465                 470                 475                 480

Val Tyr Glu Lys Leu Met Lys Ile Asn Leu Glu Ala Ala Glu Leu Gly
                485                 490                 495

Glu Ile Ser Asp Ile His Thr Lys Leu Leu Arg Leu Ser Ser Ser Gln
        500                 505                 510

Gly Thr Ile Glu Thr Ser Leu Gln Asp Ile Asp Ser Arg Leu Ser Pro
        515                 520                 525

Gly Gly Ser Leu Ala Asp Ala Trp Ala His Gln Gly Thr His Pro
        530                 535                 540

Lys Asp Arg Asn Val Glu Lys Leu Gln Val Leu Leu Asn Cys Met Thr
545                 550                 555                 560

Glu Ile Tyr Tyr Gln Phe Lys Lys Asp Lys Ala Glu Arg Arg Leu Ala
                565                 570                 575

Tyr Asn Glu Glu Gln Ile His Lys Phe Asp Lys Gln Lys Leu Tyr Tyr
                580                 585                 590
```

```
His Ala Thr Lys Ala Met Thr His Phe Thr Asp Glu Cys Val Lys Lys
            595                 600                 605

Tyr Glu Ala Phe Leu Asn Lys Ser Glu Glu Trp Ile Arg Lys Met Leu
        610                 615                 620

His Leu Arg Lys Gln Leu Leu Ser Leu Thr Asn Gln Cys Phe Asp Ile
625                 630                 635                 640

Glu Glu Glu Val Ser Lys Tyr Gln Glu Tyr Thr Asn Glu Leu Gln Glu
                645                 650                 655

Thr Leu Pro Gln Lys Met Phe Thr Ala Ser Ser Gly Ile Lys His Thr
            660                 665                 670

Met Thr Pro Ile Tyr Pro Ser Ser Asn Thr Leu Val Glu Met Thr Leu
        675                 680                 685

Gly Met Lys Lys Leu Lys Glu Glu Met Glu Gly Val Val Lys Glu Leu
690                 695                 700

Ala Glu Asn Asn His Ile Leu Glu Arg Phe Gly Ser Leu Thr Met Asp
705                 710                 715                 720

Gly Gly Leu Arg Asn Val Asp Cys Leu
                725

<210> SEQ ID NO 4
<211> LENGTH: 379
<212> TYPE: PRT
<213> ORGANISM: Homo sapiens

<400> SEQUENCE: 4

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Leu Asn Gly Val Cys
        50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
        130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
210                 215                 220

Leu Pro Gln Gln Thr Gly Asp His Ala Gly Ile Lys Asp Arg Val Tyr
225                 230                 235                 240
```

-continued

```
Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375

<210> SEQ ID NO 5
<211> LENGTH: 32
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (21)..(32)
<223> OTHER INFORMATION: Cell penetrating motif

<400> SEQUENCE: 5

Lys Lys Tyr Lys Asn Ile Val Leu Leu Lys Gly Leu Glu Val Ile Asn
1               5                   10                  15

Asp Tyr His Phe Gly Arg Lys Lys Arg Arg Gln Arg Arg Arg Pro Gln
            20                  25                  30

<210> SEQ ID NO 6
<211> LENGTH: 32
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (21)..(32)
<223> OTHER INFORMATION: Cell penetrating motif

<400> SEQUENCE: 6

Leu Glu Val Ile Asn Asp Tyr His Phe Arg Met Val Lys Ser Leu Leu
1               5                   10                  15

Ser Asn Asp Leu Gly Arg Lys Lys Arg Arg Gln Arg Arg Arg Pro Gln
            20                  25                  30

<210> SEQ ID NO 7
<211> LENGTH: 32
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
```

```
<221> NAME/KEY: MISC_FEATURE
<222> LOCATION: (21)..(32)
<223> OTHER INFORMATION: Cell penetrating motif

<400> SEQUENCE: 7

Leu Leu Ser Asn Asp Leu Lys Leu Asn Leu Lys Met Arg Glu Glu Tyr
1               5                   10                  15

Asp Lys Ile Gln Gly Arg Lys Lys Arg Arg Gln Arg Arg Arg Pro Gln
            20                  25                  30

<210> SEQ ID NO 8
<211> LENGTH: 31
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (20)..(31)
<223> OTHER INFORMATION: Cell penetrating motif

<400> SEQUENCE: 8

Glu Glu Tyr Asp Lys Ile Gln Ile Ala Asp Leu Met Glu Glu Lys Phe
1               5                   10                  15

Arg Gly Asp Gly Arg Lys Lys Arg Arg Gln Arg Arg Arg Pro Gln
            20                  25                  30

<210> SEQ ID NO 9
<211> LENGTH: 32
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (21)..(32)
<223> OTHER INFORMATION: Cell penetrating motif

<400> SEQUENCE: 9

Asp Leu Met Glu Glu Lys Phe Arg Gly Asp Ala Gly Leu Gly Lys Leu
1               5                   10                  15

Ile Lys Ile Phe Gly Arg Lys Lys Arg Arg Gln Arg Arg Arg Pro Gln
            20                  25                  30

<210> SEQ ID NO 10
<211> LENGTH: 32
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (21)..(32)
<223> OTHER INFORMATION: Cell penetrating motif

<400> SEQUENCE: 10

Ala Gly Leu Gly Lys Leu Ile Lys Ile Phe Glu Asp Ile Pro Thr Leu
1               5                   10                  15

Glu Asp Leu Ala Gly Arg Lys Lys Arg Arg Gln Arg Arg Arg Pro Gln
            20                  25                  30

<210> SEQ ID NO 11
<211> LENGTH: 31
<212> TYPE: PRT
```

```
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (20)..(31)
<223> OTHER INFORMATION: Cell penetrating motif

<400> SEQUENCE: 11

Glu Asp Ile Pro Thr Leu Glu Asp Leu Ala Glu Thr Leu Lys Lys Glu
1               5                   10                  15

Lys Leu Lys Gly Arg Lys Lys Arg Arg Gln Arg Arg Arg Pro Gln
            20                  25                  30

<210> SEQ ID NO 12
<211> LENGTH: 70
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (59)..(70)
<223> OTHER INFORMATION: Cell penetrating motif

<400> SEQUENCE: 12

Asn Asp Leu Lys Leu Asn Leu Lys Met Arg Glu Glu Tyr Asp Lys Ile
1               5                   10                  15

Gln Ile Ala Asp Leu Met Glu Glu Lys Phe Arg Gly Asp Ala Gly Leu
            20                  25                  30

Gly Lys Leu Ile Lys Ile Phe Glu Asp Ile Pro Thr Leu Glu Asp Leu
        35                  40                  45

Ala Glu Thr Leu Lys Lys Glu Leu Lys Gly Arg Lys Lys Arg Arg
    50                  55                  60

Gln Arg Arg Arg Pro Gln
65                  70

<210> SEQ ID NO 13
<211> LENGTH: 66
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (55)..(66)
<223> OTHER INFORMATION: Cell penetrating motif

<400> SEQUENCE: 13

Lys Lys Tyr Lys Asn Ile Val Leu Leu Lys Gly Leu Glu Val Ile Asn
1               5                   10                  15

Asp Tyr His Phe Arg Met Val Lys Ser Leu Leu Ser Asn Asp Leu Lys
            20                  25                  30

Leu Asn Leu Lys Met Arg Glu Glu Tyr Asp Lys Ile Gln Ile Ala Asp
        35                  40                  45

Leu Met Glu Glu Lys Phe Gly Lys Lys Arg Arg Gln Arg Arg Arg
    50                  55                  60

Pro Gln
65

<210> SEQ ID NO 14
```

```
<211> LENGTH: 62
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (51)..(62)
<223> OTHER INFORMATION: Cell penetrating motif

<400> SEQUEN

<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MOD_RES
<222> LOCATION: (1)..(1)
<223> OTHER INFORMATION: Leu is conjugated to a biotin moiety
<220

```
<220> FEATURE:
<221> NAME/KEY: MOD_RES
<222> LOCATION: (1)..(1)
<223> OTHER INFORMATION: Ala is conjugated to a biotin moiety
<220> FEATURE:
<221> NAME/KEY: MISC_FEATURE
<222> LOCATION: (21)..(32)
<223> OTHER INFORMATION: Cell penetrating motif

<400> SEQUENCE: 20

Ala Gly Leu Gly Lys Leu Ile Lys Ile Phe Glu Asp Ile Pro Thr Leu
1               5                   10                  15

Glu Asp Leu Ala Gly Arg Lys Lys Arg Arg Gln Arg Arg Pro Gln
            20                  25                  30

<210> SEQ ID NO 21
<211> LENGTH: 31
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MOD_RES
<222> LOCATION: (1)..(1)
<223> OTHER INFORMATION: Glu is conjugated to a biotin moiety
<220> FEATURE:
<221> NAME/KEY: MISC_FEATURE
<222> LOCATION: (20)..(31)
<223> OTHER INFORMATION: Cell penetrating motif

<400> SEQUENCE: 21

Glu Asp Ile Pro Thr Leu Glu Asp Leu Ala Glu Thr Leu Lys Lys Glu
1               5                   10                  15

Lys Leu Lys Gly Arg Lys Lys Arg Arg Gln Arg Arg Arg Pro Gln
            20                  25                  30

<210> SEQ ID NO 22
<211> LENGTH: 70
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MOD_RES
<222> LOCATION: (1)..(1)
<223> OTHER INFORMATION: Asn is conjugated to a biotin moiety
<220> FEATURE:
<221> NAME/KEY: MISC_FEATURE
<222> LOCATION: (59)..(70)
<223> OTHER INFORMATION: Cell penetrating motif

<400> SEQUENCE: 22

Asn Asp Leu Lys Leu Asn Leu Lys Met Arg Glu Glu Tyr Asp Lys Ile
1               5                   10                  15

Gln Ile Ala Asp Leu Met Glu Glu Lys Phe Arg Gly Asp Ala Gly Leu
            20                  25                  30

Gly Lys Leu Ile Lys Ile Phe Glu Asp Ile Pro Thr Leu Glu Asp Leu
                35                  40                  45

Ala Glu Thr Leu Lys Lys Glu Lys Leu Lys Gly Arg Lys Lys Arg Arg
    50                  55                  60

Gln Arg Arg Arg Pro Gln
65                  70

<210> SEQ ID NO 23
<211> LENGTH: 66
```

```
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MOD_RES
<222> LOCATION: (1)..(1)
<223> OTHER INFORMATION: Lys is conjugated to a biotin moiety
<220> FEATURE:
<221> NAME/KEY: MISC_FEATURE
<222> LOCATION: (55)..(66)
<223> OTHER INFORMATION: Cell penetrating motif

<400> SEQUENCE: 23

Lys Lys Tyr Lys Asn Ile Val Leu Leu Lys Gly Leu Glu Val Ile Asn
1               5                   10                  15

Asp Tyr His Phe Arg Met Val Lys Ser Leu Leu Ser Asn Asp Leu Lys
            20                  25                  30

Leu Asn Leu Lys Met Arg Glu Glu Tyr Asp Lys Ile Gln Ile Ala Asp
        35                  40                  45

Leu Met Glu Glu Lys Phe Gly Arg Lys Lys Arg Arg Gln Arg Arg Arg
    50                  55                  60

Pro Gln
65

<210> SEQ ID NO 24
<211> LENGTH: 62
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MOD_RES
<222> LOCATION: (1)..(1)
<223> OTHER INFORMATION: His is conjugated to a biotin moiety
<220> FEATURE:
<221> NAME/KEY: MISC_FEATURE
<222> LOCATION: (51)..(62)
<223> OTHER INFORMATION: Cell penetrating motif

<400> SEQUENCE: 24

His Phe Arg Met Val Lys Ser Leu Leu Ser Asn Asp Leu Lys Leu Asn
1               5                   10                  15

Leu Lys Met Arg Glu Glu Tyr Asp Lys Ile Gln Ile Ala Asp Leu Met
            20                  25                  30

Glu Glu Lys Phe Arg Gly Asp Ala Gly Leu Gly Lys Leu Ile Lys Ile
        35                  40                  45

Phe Glu Gly Arg Lys Lys Arg Arg Gln Arg Arg Arg Pro Gln
    50                  55                  60

<210> SEQ ID NO 25
<211> LENGTH: 32
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (21)..(32)
<223> OTHER INFORMATION: Cell penetrating motif

<400> SEQUENCE: 25

Lys Lys Tyr Lys Asn Ile Val Leu Leu Lys Gly Leu Glu Val Ile Asn
1               5                   10                  15
```

```
Asp Tyr His Phe Gly Arg Lys Lys Arg Arg Gln Arg Arg Pro Gln
            20                  25                  30
```

```
<210> SEQ ID NO 26
<211> LENGTH: 20
<212> TYPE: PRT
<213> ORGANISM: Artificial sequence
<220> FEATURE:
<223> OTHER INFORMATION: Synthetic pyrin domain analog
<220> FEATURE:
<221> NAME/KEY: MOD_RES
<222> LOCATION: (1)..(1)
<223> OTHER INFORMATION: Lys is conjugated to a biotin moiety

<400> SEQUENCE: 26

Lys Lys Tyr Lys Asn Ile Val Leu Leu Lys Gly Leu Glu Val Ile Asn
1               5                   10                  15

Asp Tyr His Phe
            20
```

```
<210> SEQ ID NO 27
<211> LENGTH: 31
<212> TYPE: PRT
<213> ORGANISM: Artificial sequence
<220> FEATURE:
<223> OTHER INFORMATION: Synthetic pyrin domain analog including a cell
      penetrating motif
<220> FEATURE:
<221> NAME/KEY: MISC_FEATURE
<222> LOCATION: (19)..(31)
<223> OTHER INFORMATION: Cell penetrating motif

<400> SEQUENCE: 27

Glu Asp Ile Pro Thr Leu Glu Asp Leu Ala Glu Thr Leu Lys Lys Glu
1               5                   10                  15

Lys Leu Lys Gly Arg Lys Lys Arg Arg Gln Arg Arg Arg Pro Gln
            20                  25                  30
```

```
<210> SEQ ID NO 28
<211> LENGTH: 19
<212> TYPE: PRT
<213> ORGANISM: Artificial sequence
<220> FEATURE:
<223> OTHER INFORMATION: Synthetic pyrin domain analog
<220> FEATURE:
<221> NAME/KEY: MOD_RES
<222> LOCATION: (1)..(1)
<223> OTHER INFORMATION: Glu is conjugated to a biotin moiety

<400> SEQUENCE: 28

Glu Asp Ile Pro Thr Leu Glu Asp Leu Ala Glu Thr Leu Lys Lys Glu
1               5                   10                  15

Lys Leu Lys
```

```
<210> SEQ ID NO 29
<211> LENGTH: 522
<212> TYPE: PRT
<213> ORGANISM: Homo sapiens

<400> SEQUENCE: 29

Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30

Asp Pro Thr Glu Ser Pro Ala Ala Pro Glu Ala Ala Leu Pro Lys Ala
```

```
                35                  40                  45
Gly Lys Phe Gly Pro Ala Arg Lys Ser Gly Ser Arg Gln Lys Ser
 50                  55                  60

Ala Pro Asp Thr Gln Glu Arg Pro Val Arg Ala Thr Gly Ala Arg
 65                  70                  75                  80

Ala Lys Lys Ala Pro Gln Arg Ala Gln Asp Thr Gln Pro Ser Asp Ala
                 85                  90                  95

Thr Ser Ala Pro Gly Ala Glu Gly Leu Glu Pro Pro Ala Ala Arg Glu
                100                 105                 110

Pro Ala Leu Ser Arg Ala Gly Ser Cys Arg Gln Arg Gly Ala Arg Cys
                115                 120                 125

Ser Thr Lys Pro Arg Pro Pro Gly Pro Trp Asp Val Pro Ser Pro
130                 135                 140

Gly Leu Pro Val Ser Ala Pro Ile Leu Val Arg Arg Asp Ala Ala Pro
145                 150                 155                 160

Gly Ala Ser Lys Leu Arg Ala Val Leu Glu Lys Leu Lys Leu Ser Arg
                165                 170                 175

Asp Asp Ile Ser Thr Ala Ala Gly Met Val Lys Gly Val Val Asp His
                180                 185                 190

Leu Leu Leu Arg Leu Lys Cys Asp Ser Ala Phe Arg Gly Val Gly Leu
                195                 200                 205

Leu Asn Thr Gly Ser Tyr Tyr Glu His Val Lys Ile Ser Ala Pro Asn
210                 215                 220

Glu Phe Asp Val Met Phe Lys Leu Glu Val Pro Arg Ile Gln Leu Glu
225                 230                 235                 240

Glu Tyr Ser Asn Thr Arg Ala Tyr Tyr Phe Val Lys Phe Lys Arg Asn
                245                 250                 255

Pro Lys Glu Asn Pro Leu Ser Gln Phe Leu Glu Gly Glu Ile Leu Ser
                260                 265                 270

Ala Ser Lys Met Leu Ser Lys Phe Arg Lys Ile Ile Lys Glu Glu Ile
                275                 280                 285

Asn Asp Ile Lys Asp Thr Asp Val Ile Met Lys Arg Lys Arg Gly Gly
290                 295                 300

Ser Pro Ala Val Thr Leu Leu Ile Ser Glu Lys Ile Ser Val Asp Ile
305                 310                 315                 320

Thr Leu Ala Leu Glu Ser Lys Ser Ser Trp Pro Ala Ser Thr Gln Glu
                325                 330                 335

Gly Leu Arg Ile Gln Asn Trp Leu Ser Ala Lys Val Arg Lys Gln Leu
                340                 345                 350

Arg Leu Lys Pro Phe Tyr Leu Val Pro Lys His Ala Lys Glu Gly Asn
                355                 360                 365

Gly Phe Gln Glu Glu Thr Trp Arg Leu Ser Phe Ser His Ile Glu Lys
                370                 375                 380

Glu Ile Leu Asn Asn His Gly Lys Ser Lys Thr Cys Cys Glu Asn Lys
385                 390                 395                 400

Glu Glu Lys Cys Cys Arg Lys Asp Cys Leu Lys Leu Met Lys Tyr Leu
                405                 410                 415

Leu Glu Gln Leu Lys Glu Arg Phe Lys Asp Lys Lys His Leu Asp Lys
                420                 425                 430

Phe Ser Ser Tyr His Val Lys Thr Ala Phe Phe His Val Cys Thr Gln
                435                 440                 445

Asn Pro Gln Asp Ser Gln Trp Asp Arg Lys Asp Leu Gly Leu Cys Phe
                450                 455                 460
```

Asp Asn Cys Val Thr Tyr Phe Leu Gln Cys Leu Arg Thr Glu Lys Leu
465                 470                 475                 480

Glu Asn Tyr Phe Ile Pro Glu Phe Asn Leu Phe Ser Ser Asn Leu Ile
                485                 490                 495

Asp Lys Arg Ser Lys Glu Phe Leu Thr Lys Gln Ile Glu Tyr Glu Arg
            500                 505                 510

Asn Asn Glu Phe Pro Val Phe Asp Glu Phe
        515                 520

<210> SEQ ID NO 30
<211> LENGTH: 507
<212> TYPE: PRT
<213> ORGANISM: Mus musculus

<400> SEQUENCE: 30

Met Glu Asp Pro Arg Arg Thr Thr Ala Pro Arg Ala Lys Lys Pro
1               5                   10                  15

Ser Ala Lys Arg Ala Pro Thr Gln Pro Ser Arg Thr Arg Ala His Ala
            20                  25                  30

Glu Ser Cys Gly Pro Gln Arg Gly Ala Arg Ser Arg Arg Ala Glu Arg
        35                  40                  45

Asp Gly Asp Thr Thr Glu Lys Pro Arg Ala Pro Gly Pro Arg Val His
    50                  55                  60

Pro Ala Arg Ala Thr Glu Leu Thr Lys Asp Ala Gln Pro Ser Ala Met
65                  70                  75                  80

Asp Ala Ala Gly Ala Thr Ala Arg Pro Ala Val Arg Val Pro Gln Gln
                85                  90                  95

Gln Ala Ile Leu Asp Pro Glu Leu Pro Ala Val Arg Glu Pro Gln Pro
            100                 105                 110

Pro Ala Asp Pro Glu Ala Arg Lys Val Val Arg Gly Pro Ser His Arg
        115                 120                 125

Arg Gly Ala Arg Ser Thr Gly Gln Pro Arg Ala Pro Arg Gly Ser Arg
    130                 135                 140

Lys Glu Pro Asp Lys Leu Lys Lys Val Leu Asp Lys Leu Arg Leu Lys
145                 150                 155                 160

Arg Lys Asp Ile Ser Glu Ala Ala Glu Thr Val Asn Lys Val Val Glu
                165                 170                 175

Arg Leu Leu Arg Arg Met Gln Lys Arg Glu Ser Glu Phe Lys Gly Val
            180                 185                 190

Glu Gln Leu Asn Thr Gly Ser Tyr Tyr Glu His Val Lys Ile Ser Ala
        195                 200                 205

Pro Asn Glu Phe Asp Val Met Phe Lys Leu Glu Val Pro Arg Ile Glu
    210                 215                 220

Leu Gln Glu Tyr Tyr Glu Thr Gly Ala Phe Tyr Leu Val Lys Phe Lys
225                 230                 235                 240

Arg Ile Pro Arg Gly Asn Pro Leu Ser His Phe Leu Glu Gly Glu Val
                245                 250                 255

Leu Ser Ala Thr Lys Met Leu Ser Lys Phe Arg Lys Ile Ile Lys Glu
            260                 265                 270

Glu Val Lys Glu Ile Lys Asp Ile Asp Val Ser Val Lys Glu Lys
        275                 280                 285

Pro Gly Ser Pro Ala Val Thr Leu Leu Ile Arg Asn Pro Glu Glu Ile
    290                 295                 300

Ser Val Asp Ile Ile Leu Ala Leu Glu Ser Lys Gly Ser Trp Pro Ile

```
                305                 310                 315                 320
Ser Thr Lys Glu Gly Leu Pro Ile Gln Gly Trp Leu Gly Thr Lys Val
                325                 330                 335

Arg Thr Asn Leu Arg Arg Glu Pro Phe Tyr Leu Val Pro Lys Asn Ala
                340                 345                 350

Lys Asp Gly Asn Ser Phe Gln Gly Glu Thr Trp Arg Leu Ser Phe Ser
                355                 360                 365

His Thr Glu Lys Tyr Ile Leu Asn Asn His Gly Ile Glu Lys Thr Cys
                370                 375                 380

Cys Glu Ser Ser Gly Ala Lys Cys Cys Arg Lys Glu Cys Leu Lys Leu
385                 390                 395                 400

Met Lys Tyr Leu Leu Glu Gln Leu Lys Lys Glu Phe Gln Glu Leu Asp
                405                 410                 415

Ala Phe Cys Ser Tyr His Val Lys Thr Ala Ile Phe His Met Trp Thr
                420                 425                 430

Gln Asp Pro Gln Asp Ser Gln Trp Asp Pro Arg Asn Leu Ser Ser Cys
                435                 440                 445

Phe Asp Lys Leu Leu Ala Phe Phe Leu Glu Cys Leu Arg Thr Glu Lys
                450                 455                 460

Leu Asp His Tyr Phe Ile Pro Lys Phe Asn Leu Phe Ser Gln Glu Leu
465                 470                 475                 480

Ile Asp Arg Lys Ser Lys Glu Phe Leu Ser Lys Lys Ile Glu Tyr Glu
                485                 490                 495

Arg Asn Asn Gly Phe Pro Ile Phe Asp Lys Leu
                500                 505

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gagtagcgcg agcacagcta                                                 20

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
gtaccaacgc ttgaagacc                                                  19

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gttccgaggt gatgctggtt                                                 20

<210> SEQ ID NO 34
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 34
gaccagccct atcaagaaag                                                  20

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
gactcggtgg gatccatcg                                                   19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
gagcacactc tccggtacc                                                   19

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
gtcagattct ggtagtccat                                                  20

<210> SEQ ID NO 38
<211> LENGTH: 100
<212> TYPE: DNA
<213> ORGANISM: Artificial Sequence
<220> FEATURE:
<223> OTHER INFORMATION: Synthetic

<400> SEQUENCE: 38
agaaaagttc cgaggtgatg ctggtttggg caaactaata aaattttcg aagatatacc       60 aaggcttgaa gacctggctg aaactcttaa aaagaaaag                            100

<210> SEQ ID NO 39
<211> LENGTH: 100
<212> TYPE: DNA
<213> ORGANISM: Artificial Sequence
<220> FEATURE:
<223> OTHER INFORMATION: Synthetic

<400> SEQUENCE: 39
agtaaaagga ccagccctat caagaaagag gaagaaggaa gtggatgcta cttcacctgc      60
accctccaca agcagcactg tcaaaactga aggagcagag                           100
```

METHODS OF TREATING A DISORDER ASSOCIATED WITH WITH INSUFFICIENT STIMULATOR OF INTERFERON GENES (STING) ACTIVITY

RELATED APPLICATIONS

This application is a national stage filing under 35 U.S.C. § 371 of international PCT application PCT/EP2017/070208, filed Aug. 9, 2017, which claims the benefit of DKPA201770079 filed on Feb. 8, 2017, which claims the benefit of DKPA201670606 filed on Aug. 9, 2016, the entire contents of each of which are incorporated by reference herein.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Mar. 6, 2023, is named 5211070000US00-SUBSEQ-DQB and is 42,843 bytes in size.

BACKGROUND

Innate immune activation by cytosolic DNA from microbial pathogens is a potent trigger of type I Interferon (IFN) and pro-inflammatory cytokines. The pathway that leads to IFN activation has been extensively studied both in terms of the proteins binding cytosolic DNA and those needed for subsequent downstream signalling and immune activation. Although multiple candidates have been suggested as sensors for cytosolic DNA, particularly two proteins have been demonstrated by separate laboratories to play a role in DNA-driven IFN responses. These are cyclic GMP-AMP synthetase (cGAS) and IFN gamma-inducible factor 16 (IFI16). IFI16, a cytosolic and nuclear protein, has been associated with induction of type I IFN (IFN-α and IFN-β) upon stimulation with single-stranded and double-stranded DNA and by infection with different herpesviruses, human immunodeficiency virus type 1 (HIV) and bacteria. cGAS is a cytosolic protein, which is important for sensing all forms of structured DNA and recognized as the pivotal sensor of microbial DNA. It has the enzymatic capacity to produce the second messenger cyclic GMP-AMP (cGAMP), which docks onto the endoplasmic reticulum-bound protein stimulator of interferon genes (STING). This interaction induces conformational changes that allow STING to homodimerize, migrate from the ER, and recruit TANK-binding kinase 1 (TBK1). How TBK1 is actively recruited to STING is currently unknown, but absence of TBK1 binding to STING results in impaired immune activation. A recent report demonstrated that TBK1 binding to STING initiates a complex cascade of events including phosphorylation of STING as well as recruitment and activation of IFN regulatory factor 3 (IRF3). Lack of phosphorylation of STING at Ser$^{366}$ abolishes downstream signalling and immune activation, demonstrating the importance of precise and direct activation of STING. Studies of cGAS-deficient mice proved a clear phenotype in innate immune responses. As mice do not have a direct ortholog to human IFI16, data from IFI16-deficient mouse models are not available. Due to the lack of a definitive murine IFI16 ortholog, mouse models are poorly suitable to resolve the potential interconnection between cGAS and IFI16 in the innate immune response to foreign DNA.

In contrast to the well-described mechanism of action of cGAS in DNA sensing, there is limited knowledge on how IFI16 is related to STING-dependent signalling and also whether IFI16 may or may not be redundant to the cGAS-STING-TBK1 pathway. Previous findings have shown that the affinity of cGAS for DNA is relatively weak (Kd in the 20 uM range) and that specific sizes or structures of the DNA are required for cGAS to engage binding. Thus it seem plausible that cGAS responds efficiently to cytosolic DNA with help from one or more co-factors.

SUMMARY

The present invention discloses novel functions of human IFI16 in the cGAS-STING pathway. Furthermore, the invention discloses that the pyrin-domain of IFI16 may be involved in the IFI16 and STING activity. These findings open up an entire new approach for regulation of STING activity and thereby modulation of the innate immune response.

Thus, in one aspect, a compound is provided, which is capable of mimicking the pyrin-domain of IFI16. This compound is in a preferred embodiment a polypeptide, for example a polypeptide comprising or consisting of pyrin-domain of human IFI16 or a fraction and/or functional homologue thereof. Alternatively, the provided compound is a compound is capable of binding a polypeptide comprising or consisting of pyrin-domain of human IFI16 or a fraction and/or functional homologue thereof.

The compound may also comprise one or more conjugated moieties, such as in particular a cell-penetrating peptide.

The provided compounds are in a particular aspect also in one aspect provided herein for use in medicine, i.e. for use as a medicament, including for use in treatment of disorders associated with insufficient STING activity or disorders associated with excessive STING activity. It is also understood that the compounds are provided for the treatment of any disorder, which modulation of STING activity could prevent or ameliorate.

In another aspect, a method is provided of treating a disorder associated with STING activity comprising administering the compound or the polypeptide of the invention to an individual in need thereof.

In one embodiment the invention relates to a compound capable of binding to the pyrin-domain of IFI16 or a fragment thereof for use in the treatment of a disorder associated with STING activity.

In one embodiment the invention relates to a method of treating a disorder associated with STING activity comprising administering a compound capable of binding to the pyrin-domain of IFI16 or a fragment thereof to an individual in need thereof.

The invention also provides methods of identifying a compound capable of binding the pyrin-domain of IFI16, said method comprising the steps of
   providing a pyrin-domain of IFI16 or a fragment thereof
   providing a library of test compounds
   contacting the pyrin-domain of IFI16 with said test compounds
   detecting and isolating test compounds, which interact with the pyrin-domain of IFI16 or the fragment thereof
thereby identifying an anti-inflammatory agent.

In addition, the invention provides compounds capable of mimicking the pyrin-domain of IFI16, thereby inducing STING activity. In particular, said compounds may comprise or consist of the pyrin-domain of IFI16 or a fragment thereof.

The invention also provides polypeptides comprising or consisting of the pyrin-domain of IFI16 or a fragment thereof, wherein the polypeptides optionally may be linked to at least one conjugated moiety.

The invention also provides methods of identifying a compound capable of mimicking the pyrin-domain of IFI16, said method comprising the steps of
 providing a library of test compounds
 testing whether said test compounds are capable of inducing STING activity
thereby identifying a compound capable of mimicking IFI16 pyrin domain.

In one embodiment the invention provides compounds capable of mimicking the pyrin-domain of IFI16 or polypeptides comprising the pyrin-domain of IFI16 or a fragment thereof, for use in the treatment of a disorder associated with insufficient STING activity

DESCRIPTION OF DRAWINGS

(FIGS. 1A-1B) Type I IFN expression was evaluated in control, IFI16 KO, cGAS KO and STING KO THP-1 cells challenged with HSV1 (e) or hCMV (f) 18 hrs after infection using a MOI of 3. (FIG. 1C) Type I IFN expression was evaluated in control and IFI16 KO cells at 2, 4 and 8 hrs after HSV1 infection using a MOI of 10. Data in (FIGS. 1A-1B) represent the mean±SD of biological triplicates, representative of two independent experiments. Unpaired t-test corrected for multiple comparisons using Holm-Sidak was been performed to evaluate the significance. *P<0.05; ** P<0.01.

(FIG. 2A) Control and IFI16 CRISPR KO THP-1 cells were transfected with dsDNA at various concentrations and IFN induction measured after 6 hrs. (FIGS. 2B-2C) Control and IFI16 KO cells were transfected with dsDNA (4 µg/ml) at indicated time-points (FIG. 2B) or poly (I:C) (1 µg/ml or 5 µg/ml) for 20 hours (FIG. 2C), hereafter supernatants were evaluated for type I IFN expression. (FIG. 2D) Whole cell lysates from control or IFI16 KO cells stimulated with dsDNA (4 µg/ml) at indicated time-points were subjected to immunoblotting using antibodies against STING, pIRF3, pTBK1, total TBK, total IRF3, and vinculin (VCL) as loading control. (FIG. 2E) Control or IFI16 KO cells were transfected with dsDNA (4 µg/ml) for two and four hours. The cells were fixed and stained with anti-IFI16 (Green) and anti-STING (Red) specific antibodies. DNA was visualized with DAPI (blue).

Data represent mean±SD of biological triplicates, representative of three independent experiments. Unpaired t-test corrected for multiple comparisons using Holm-Sidak was been performed to evaluate the significance. *P<0.05;  P<0.01; *P<0.001.

FIGS. 3A-3D: STING dimerization and phosphorylation is dependent on IFI16.

Figure 3A:
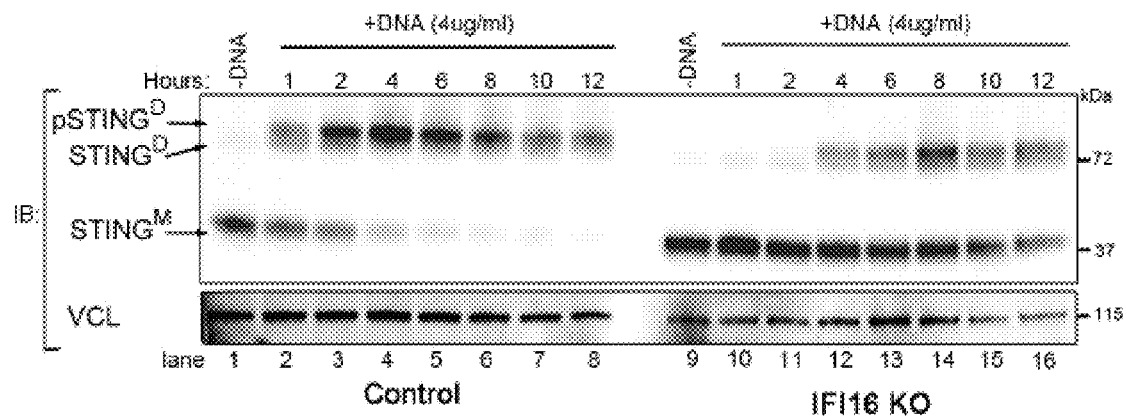
Figure 3B:
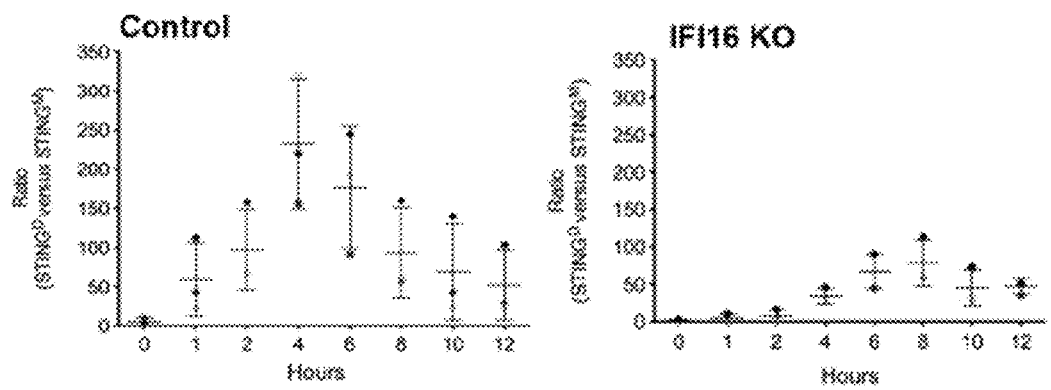
Figure 3C:
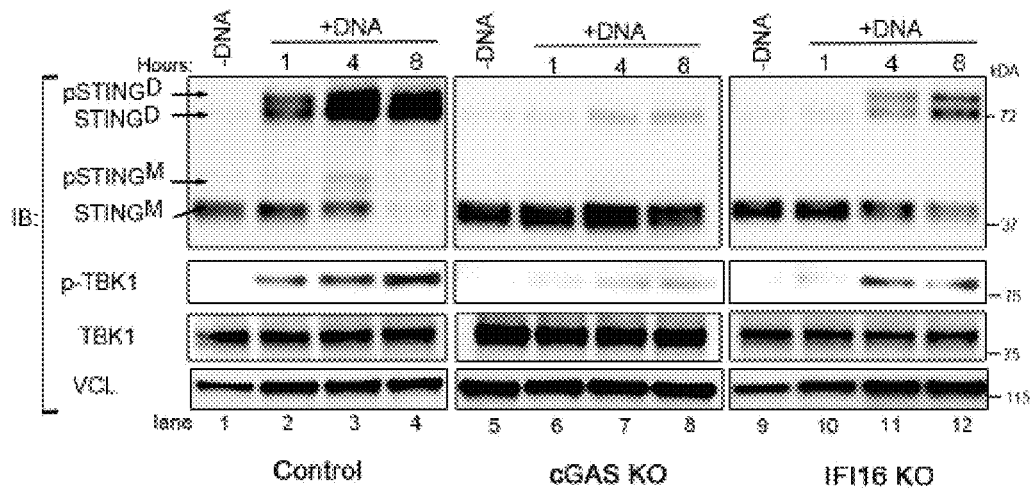
Figure 3D:
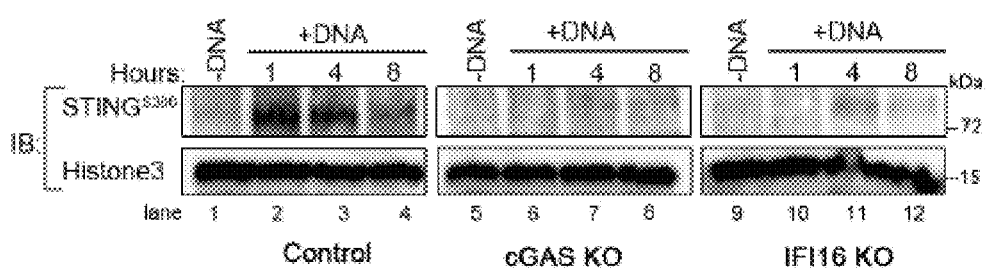

(FIGS. 3A-3B) Control and IFI16 KO THP-1 cells were stimulated with dsDNA (4 µg/ml) at indicated time-points and whole cell lysates were subjected to immunoblotting of STING dimerization by semi-native gel electrophoresis. Vinculin (VCL) was used as loading control. (FIG. 3B) The quantification of band intensity of $STING^{Dimer}$ vs $STING^{Monomer}$ was done using ImageJ software of three independent experimental setups. (FIGS. 3C-3D) Control, cGAS KO and IFI16 KO cells were stimulated with dsDNA (4 µg/ml) at indicated time-points and whole cell lysates were subjected to both semi-native gel electrophoresis and standard SDS-page. Membranes were probed with antibodies against STING, p-TBK1 and VCL (FIG. 3C) or phosphor-specific STING S366 and Histone3 as loading control (FIG. 3D). Data presented in (FIGS. 3A, 3C) are representative of at least three independent experiments, whereas data in (FIG. 3D) is representative of two independent experiments.

FIGS. 4A-4F: Recruitment of TBK1 to STING is dependent on IFI16 interactions.

(FIG. 4A) Schematic illustration of the workflow of co-immunoprecipitation experiments. Cleared cell lysates (CCL) of THP-1 cells stimulated with dsDNA (4 µg/ml) for 2 and 4 hrs were subjected to over-night co-immunoprecipitation with antibodies indicated in each panel. Lysates from control cells were co-IP with STING (lane 1-3) or IFI16 (lane 4-6). Input and elutes were analysed by gel electrophoresis followed by immunoblotting (IB) with the indicated antibodies. (FIG. 4B) STING co-IP samples from primary human MDMs after IB with the indicated antibodies. (FIG. 4C) STING co-IP samples from control (lane 1-3) and IFI16 KO (lane 4-6) THP-1 cells after IB with the indicated antibodies. (FIG. 4D) IFI16 co-IP samples from STING KO THP-1 cells after IB with the indicated antibodies. Each blot is representative of three independent experiments. (FIG. 4E) Control or IFI16 KO cells were stimulated with dsDNA (4 µg/ml) for 2 hrs, fixed and stained for DAPI (blue), anti-IFI16 (green) or anti-IRF3 (red) and subjected to confocal imaging at ×63 oil lens. (FIG. 4F) Quantification of IRF3 localisation of at least 50 individual cells treated as described in FIG. 4E.

FIGS. 5A-5J: cGAMP production is regulated by IFI16.

(FIG. 5A) External calibration curve of spiked (2'3'-3'5')-cGAMP into cell extract prior to column purification were used to quantify cGAMP production in stimulated cells. The calibration curve was linear up to a concentration of at least 400 nM with an R2 of 0.991. The chromatogram demonstrates the peak detected using synthetic cGAMP. (FIG. 5B) LC-MS/MS chromatograms of whole cell lysates from control and IFI16 KO THP-1 cells stimulated with dsDNA for 2, 4 or 8 hrs. (FIG. 5C) Quantitative LC-MS/MS analysis of control and IFI16 KO THP-1 of three individual single clones. (FIG. 5D) Immunoblotting of HEK29T with or without stable transduction of human IFI16 (CE, cytoplasmic extract; ME, membrane extract; NE, nuclear extract; PE, pellet extract). (FIG. 5E) Quantitative LC-MS/MS analysis of HEK293T with or without stable transduction of human IFI16 24 hrs after transfection with increasing doses of cGAS expressing plasmid. (FIG. 5F) Immunoblotting of HEK293T with or without stable transduction of human STING. (FIG. 5G) $HEK293T^{STING}$ cells were transfected with cGAS expressing plasmid (25 ng/well) and increasing doses of IFI16 expressing plasmid (0, 250, 500, 750 and 1000 ng/well). STING activation was evaluated 24 hrs later by measuring expression of an IFN-β promoter Firefly gene normalized to a beta-actin promotor Renilla gene. (FIG. 5H) Diagram of IFI16 domains and the two different IFI16-mutants used to transient express IFI16 protein in HEK293T stable expressing human STING. An eGFP expressing plasmid was used as negative control. Transfection efficiencies were evaluated by measuring eGFP or BFP by Flow cytometry. (FIG. 5I) $HEK293T^{STING}$ cells were transfected with cGAS expressing plasmid (25 ng/well) and increasing doses of plasmids expressing wt, Pyrin or Hin IFI16 mutant. (FIG.

5J) HEK293T$^{STING}$ cells were transfected with cGAS expressing plasmid (25 ng/well) and increasing doses of plasmids expressing Pyrin containing proteins; MNDA, IFIX or IFI16.

Data in (FIGS. 5C, 5E, 5G, 5I, and 5J) represent mean±SD of biological triplicates from three independent experimental setups. Unpaired t-test corrected for multiple comparisons using Holm-Sidak was performed to evaluate the significance. For data in (FIG. 5I) One-way ANOVA was performed to evaluate significance. *P<0.05;  P<0.01, * P<0.001.

FIGS. 6A-6F: IFI16 regulates cGAMP-mediated STING activation.

(FIG. 6A) Control, IFI16, cGAS, STING KO THP-1 cells or (FIG. 6B) MDMs with IFI16 siRNA knockdown, were infused with cGAMP (50 nM) at indicated time-points and subsequently evaluated for type I IFN secretion. (FIG. 6C) STING dimerization analysis by semi-native western blotting. Upper lane represents an overexposure of the dimer STING band. Total STING was run on a separate SDS-Page gel. (FIG. 6D) Control and IFI16 KO cells were infused with cGAMP (50 nM) for 2 hrs, fixed and stained for DAPI (blue), IFI16 (green) and IRF3 (red). (FIG. 6E) IRF3 translocation from cytoplasm to nuclear saturation were quantified by counting >50 separate images of control or IFI16 KO cells 2 hrs post cGAMP infusion. (FIG. 6F) Subcellular fractions of control and IFI16 KO cells stimulated with 50 nM cGAMP for 1 hour were immunoblotted for phosphorylated IRF3 and total IRF3 in cytosolic (cyto) and nuclear (nucl) fractions. Data in (FIGS. 6A-6B) represent mean±SD of biological triplicates from (FIG. 6A) three independent experimental setups or (FIG. 6B) one donor; (FIGS. 6C-6F) data is representative of one of three independent experiments.

FIGS. 7A-7D: IFI16 regulates STING activation through its PYRIN domain.

(FIG. 7A) Control and TBK1 KO or (FIG. 7B) Control and IFI16 KO THP-1 cells were infused with cGAMP (50 nM) for 30 min, 1, 4 and 8 hours and whole cell lysates was used to evaluate STING dimerization (upper panel) and specific STING phosphorylation at Ser$^{366}$ (lower panel). (FIG. 7C) HEK293T$^{STING}$-IFI16 expressing cells were infused with cGAMP (range from 50-250 nM) for 16 hrs and the degree of STING activation was evaluated by measuring expression of an IFN-β promoter Firefly gene normalized to a beta-actin promotor Renilla gene. (FIG. 7D) HEK293T-cGAS expressing cells were co-cultured with HEK293T$^{STING}$ that had been transfected with eGFP or one of the three IFI16 variants. Twenty-four hours after culturing cGAMP transfer and STING activation was evaluated by measuring expression of IFN-β promoter Firefly gene normalized to beta-actin promotor Renilla gene.

Data represent mean±SD of biological triplicates, representative of three independent experiments. Unpaired t-test corrected for multiple comparisons using Holm-Sidak was performed to evaluate the significance. *P<0.05; ** P<0.01.

Figure 8A:
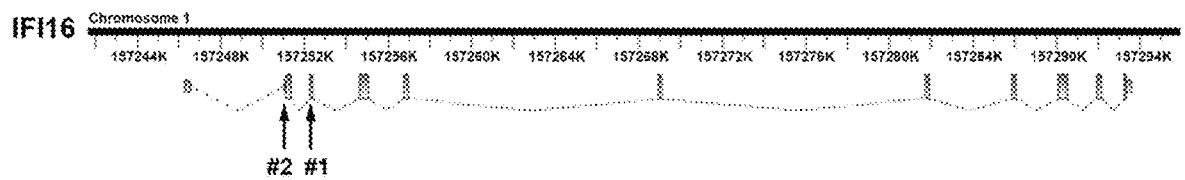
Figures 8B, 8C:
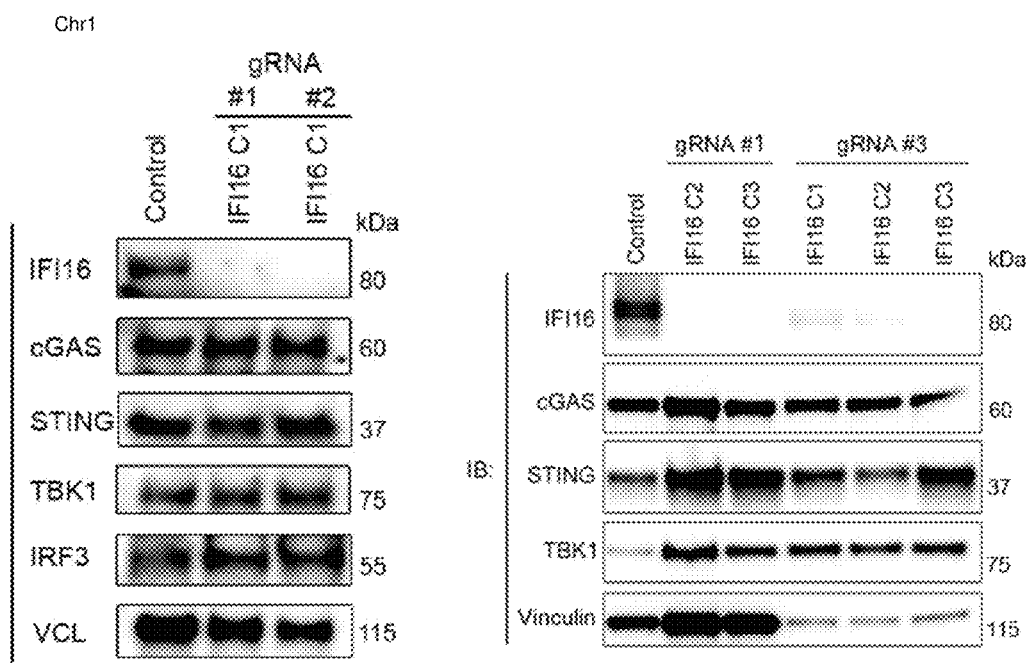

FIGS. 8A-8C. Generation of CRISPR-Cas9 mediated gene knock out in THP-1 cells.

(FIG. 8A) Graphical representation of the specific gRNA targets for IFI16 using fancyGENE software analysis tool. Introns (dashed) and exons (grey). Black arrows indicate Cas9 endonuclease mediated double stranded breaks. For information about the sequences see Materials and methods. (FIG. 8B) Effect of CRISPR gene disruption was evaluated by western blotting on PMA-differentiated THP-1 cells with the indicated immunoblotting (IB) for gRNA target 1 clone 1 and gRNA target 2 clone 1. (FIG. 8C) Evaluation of additional two IFI16 KO clones from gRNA target 1 and three clones from the third gRNA target.

Figure 9:
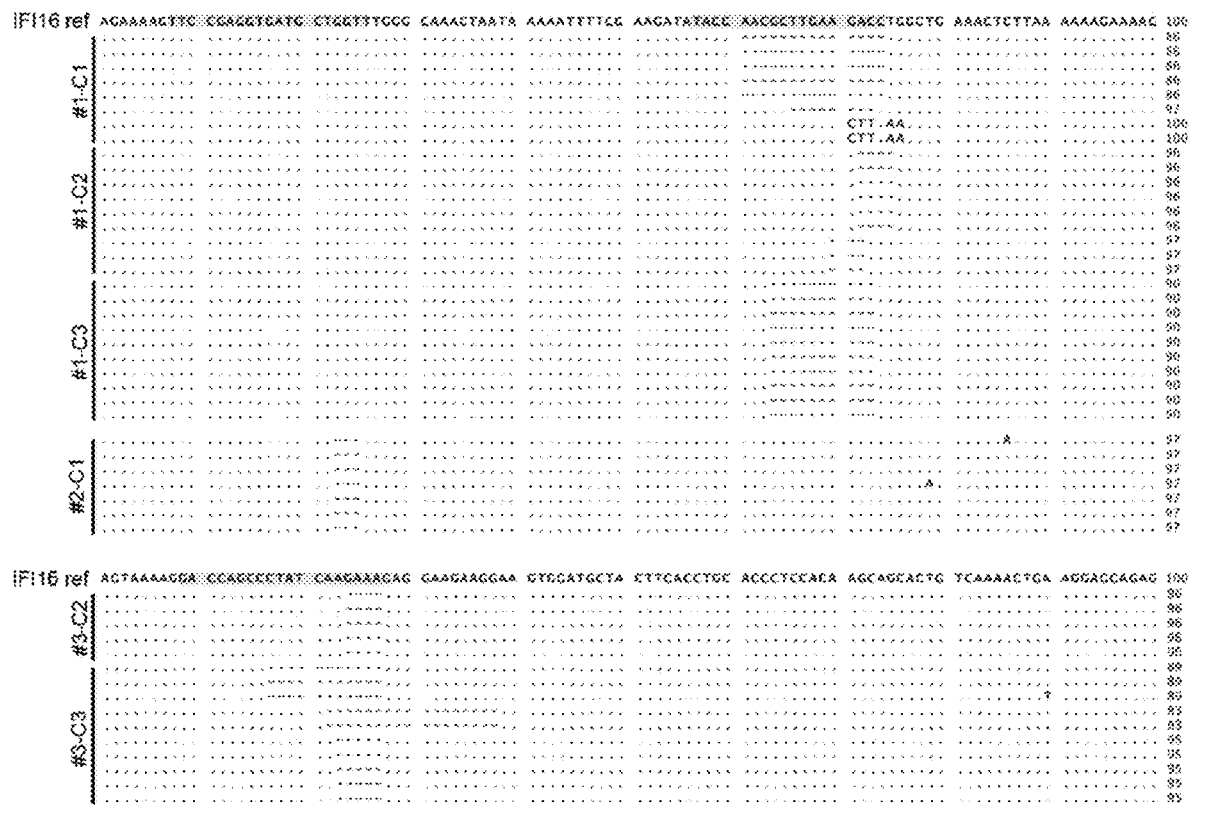

FIG. 9 Sequencing evaluation of the gene disruption in each THP1 IFI16 KO clone represented in (FIGS. 8B-8C) with the exception of gRNA #3 clone 1, which was not depleted of IFI16 and therefore excluded for further analysis. Yellow boxes represent the target area of the gRNA's (from top to bottom, SEQ ID NOs: 38-39).

Figure 10A:
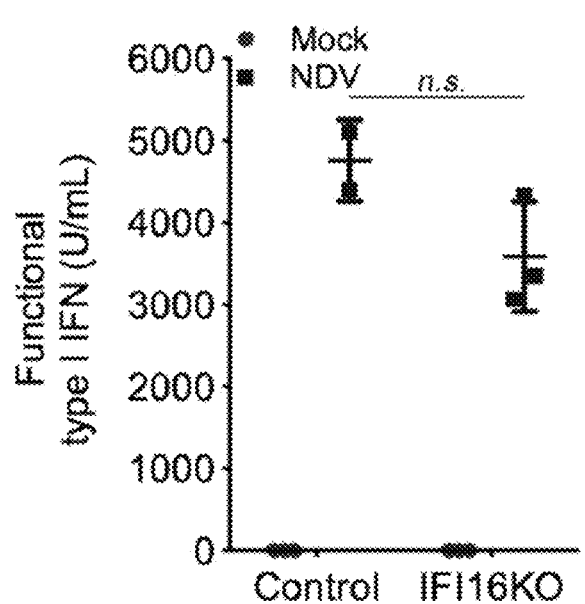
Figure 10B:
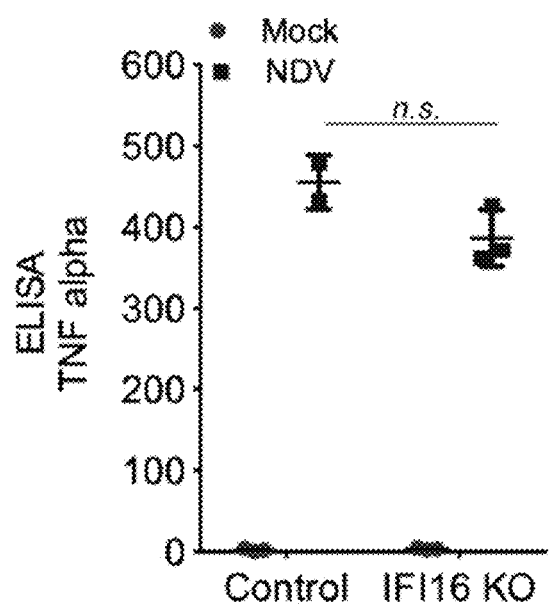
Figure 10C:
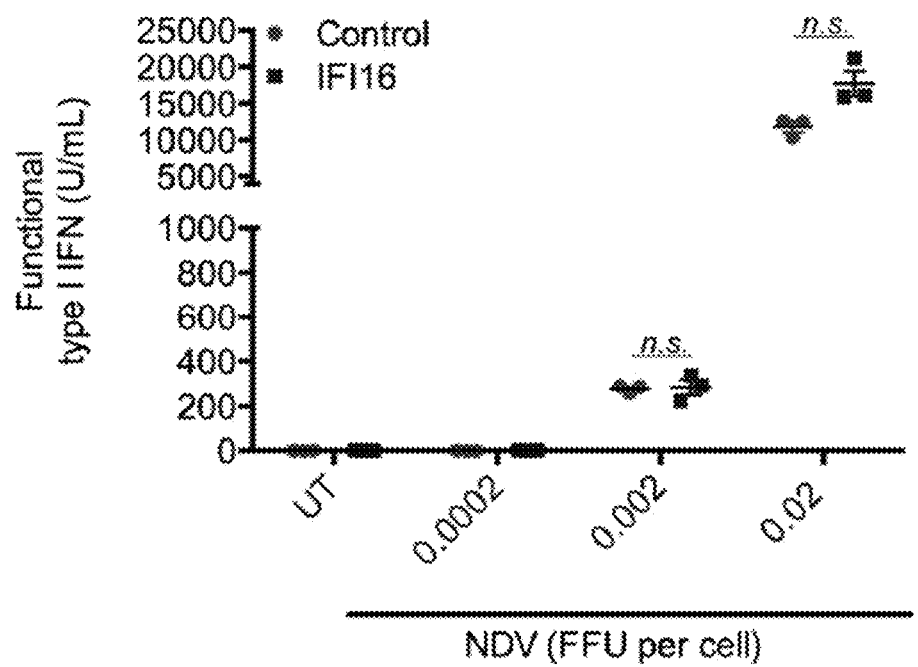

FIGS. 10A-10C. Innate immune induction by NDV infection is independent of IFI16 expression.

(FIG. 10A) Control and IFI16 KO cells were infected with NDV (FFU 0.01) for 20 hours and lysates evaluated for type I IFN expression using the HEK-Blue IFN-assay. (FIG. 10B) Same cell lysates from (FIG. 10A) were used to determine TNF-α expression using ELISA. (FIG. 10C). Control and IFI16 KO cells were infected with diluted series of NDV and type I IFN expression measured 20 hrs p.i. Data represent the mean±SD of biological triplicates. Unpaired t-test was performed to evaluate the significance. n.s., non-significant difference.

FIGS. 11A-11G. Robust induction of type I IFN by various forms of dsDNA is dependent on IFI16 expression.

Figure 11A:
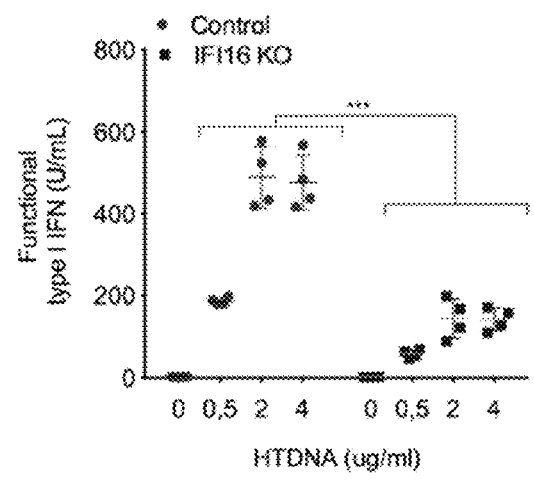

Control and IFI16 KO THP-1 cells were stimulated by lipofectamine transfection using (FIG. 11A) Herring testis dsDNA (0.5, 2 or 4 µg/ml) analysed for type I IFN induction. (FIG. 11B) As control of carrier, control and IFI16 KO cells were stimulated with lipofectamine (4 µl/ml) and evaluated as in (FIG. 11A). (FIG. 11C) Control and IFI16 KO cells were stimulated with dsDNA (4 µg/ml) at indicated time points and CXCL10 secretion measured by ELISA. (FIG. 11D) TNF-α ELISA analysis on supernatants from control and IFI16 KO cells stimulated with Poly I:C at indicated concentrations for 18 hrs. (FIG. 11E) Control and IFI16 KO cells were incubated with TBK1 inhibitor BX795 for 2 hrs prior to dsDNA transfection (4 µg/ml). Type 1 IFN secretion was measured at the indicated time points. (FIG. 11F) Immunoblotting of TBK1 in control and TBK1 KO cells. (FIG. 11G) Control and TBK1 KO cells were stimulated dsDNA (4 µg/ml) and analysed for type I IFN induction at indicated time points.

Data represent the mean±SD of biological triplicates, representative of three independent experiments. Unpaired t-test corrected for multiple comparisons using Holm-Sidak was performed to evaluate the significance. *P<0.05;  P<0.01; * P<0.001.

Figure 12A:
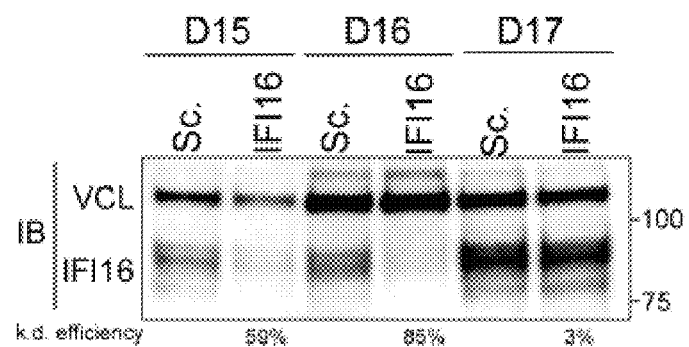
Figure 12B:
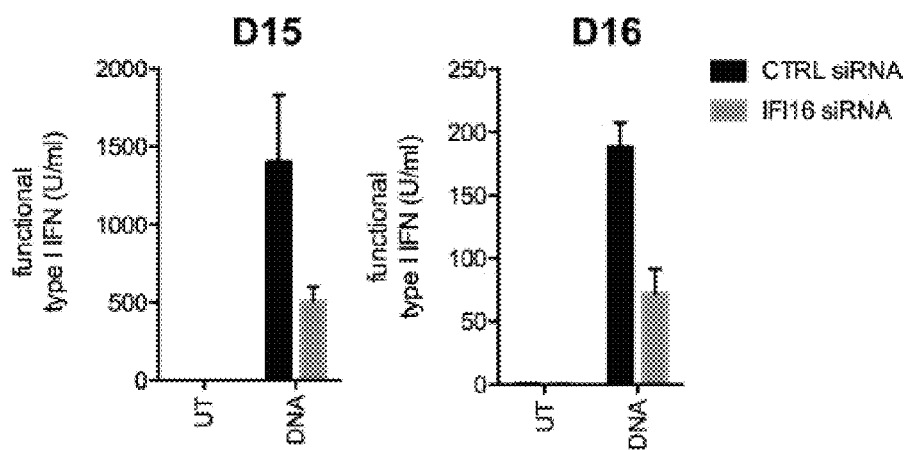
Figure 12C:
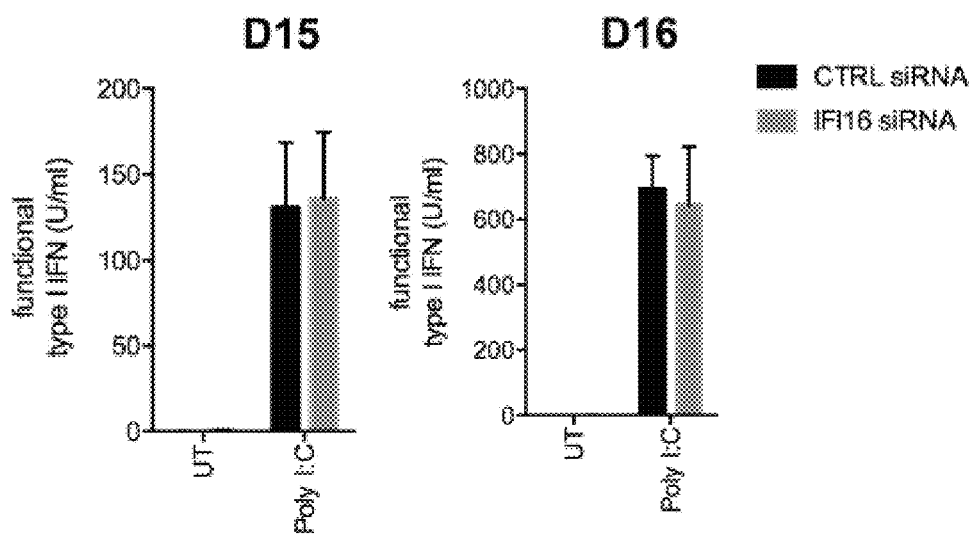

FIGS. 12A-12C. Type I IFN by dsDNA is dependent on IFI16 expression in primary human MDMs. (FIG. 12A) Level of IFI16 expression was measured by immunoblotting in three MDMs donors treated with scramble (Sc.) and IFI16-specific (IFI16) siRNA pool. Donor 15 and 16 with significant IFI16 knockdown were stimulated with either (FIG. 12B) dsDNA (4 ug/ml) or (FIG. 12C) poly(I:C) (1 ug/ml) for 20 hrs and then analysed for type I IFN expression using the HEK-Blue IFN-bioassay. The donor 17 was excluded due to limited knockdown efficiency.

FIGS. 13A-13H. Multiple CRISPR gRNA targeting IFI16 demonstrate similar phenotypes.

Figure 13A:
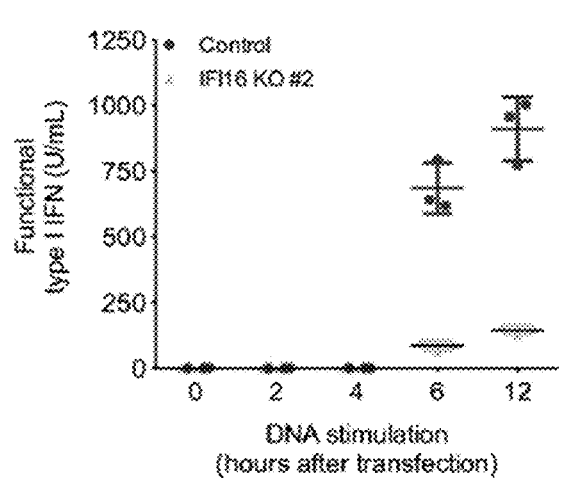
Figure 13B:
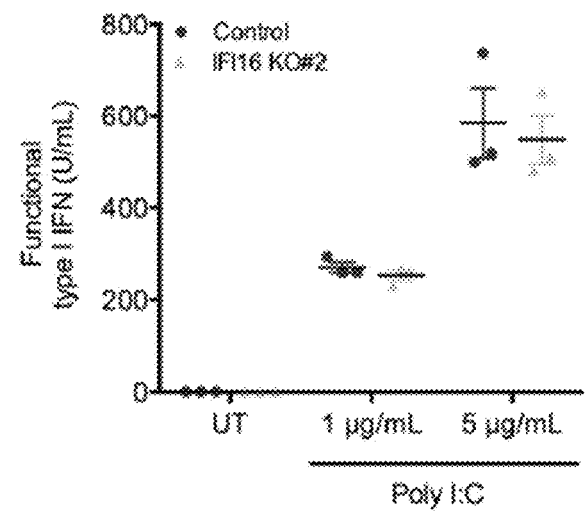
Figure 13C:
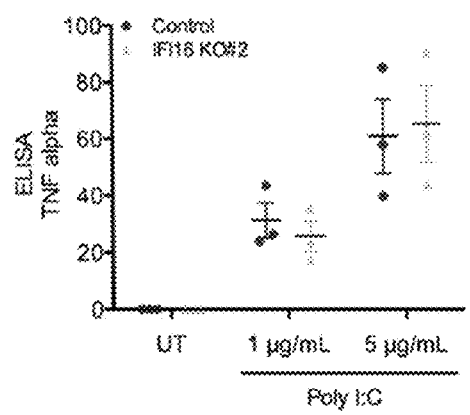
Figure 13D:
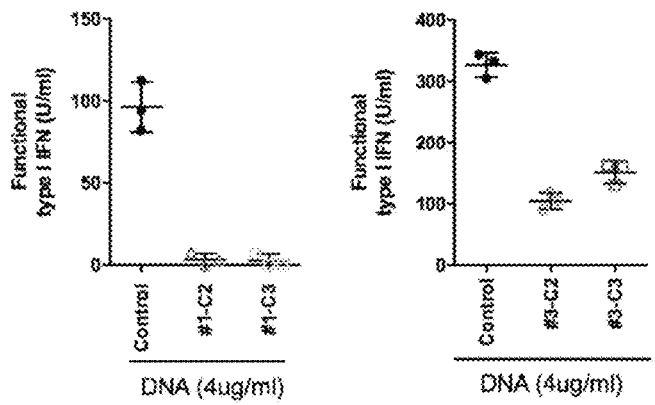

Control and IFI16 KO #2 cells were stimulated with dsDNA (4 µg/ml) at indicated time-points and evaluated for type I IFN induction (FIG. 13A); polyI:C (1 µg/ml or 5 µg/ml) for 18 hours and evaluated for type I IFN induction (FIG. 13B) or TNF-α protein expression (FIG. 13C). Four different PMA-differentiated THP-1 KO clones of IFI16 (see FIG. 8C) were (FIG. 13D) transfected with dsDNA or (FIG. 13E) infected with NDV (0.002 FFU/cell) for 20 hrs and evaluated for type I IFN induction. (FIG. 13F) PMA-differentiated THP-1 cells from control, cGAS KO, STING KO and IFI16 KO #2 were transfected with dsDNA (4 μg/ml) at indicated time-points and evaluated for type I IFN induction. (FIG. 13G) IFI16 gene expression was reconstituted in two THP1 IFI16 KO clones using lentiviral delivery. (FIG. 13H) Forty-eight hours later cells were transfected with dsDNA (4 ug/ml) and evaluated for type I IFN responses after 8 and 24 hrs. Data represent the mean±SD of biological triplicates, representative of (FIGS. 13A-13F) three and (FIG. 13H) two independent experiments. Unpaired t-test was performed to evaluate the significance. *P<0.05; ** P<0.01.

FIGS. 14A-14E: STING dimerization upon DNA stimulation.

(FIG. 14A) Whole cell lysate from control cells stimulated with dsDNA (4 μg/ml) at indicated time-points were left untreated or treated with alkaline phosphatase for 30 minutes before SDS-Page gel electrophoresis and immunoblotting with antibodies against STING and vinculin (VCL). Data are representative of two independent experiments. (FIG. 14B) STING puncta were quantified by counting fifty separate images of control or IFI16 KO cells 4 hrs p.t. (corresponding to FIG. 2E). (FIG. 14C) Confocal microscopy illustrating STING expression in THP1 Control or STING KO cells with (upper, ×40; lower ×63-olie objectives). (FIG. 14D) Control THP-1 cells were stimulated with dsDNA (4 μg/ml) at indicated hours and subjected to either native or non-native gel electrophoresis including reducing agents. Immunoblotting was done with antibodies against STING. Vinculin (VCL) was used as loading control. Data are representative of two independent experiments. (FIG. 14E) Control and IFI16 KO #2 THP-1 cells were stimulated with lipofectamine or lipofectamine+dsDNA (4 μg/ml) at indicated hours and subjected to semi-native gel electrophoresis and immunoblotting with antibodies against STING and pTBK1. Data are representative of two independent experiments.

FIG. 15.

Control and IFI16-KO cells (in triplicates) were stimulated with dsDNA (4 μg/ml) for 6 hours before extracting total RNA. RNAseq was performed using ProtonIon and the differentially expressed genes identified using the Partek Gene Specific Analysis Algorithm (customer.partek.com/GSAWhitePaper.pdf). Total gene expression (number of reads normalised to total reads) are presented for 6 selected genes: IFI44L, VIPERIN, IFNB1, MX1, APOBEC3F and GBPS. The box represents interquartile range, with the line in the middle representing the median while the whiskers symbolize 90% to 10% range.

FIG. 16.

Cleared cell lysates (CCL) of THP-1 STING KO or IFI16 KO cells stimulated with dsDNA (4 μg/ml) for 2 and 4 hrs were subjected to over-night co-immunoprecipitation with antibodies indicated in each panel. Lysates from control cells were co-IP with STING (left panel) or IFI16 (right panel). Input and elutes were analysed by gel electrophoresis followed by immunoblotting (IB) with the indicated antibodies. Each blot is representative of two independent experiments. Asterisk marker indicates an unspecific band at approximately 50 kDa in the cell lysate fraction. The specific band for STING is 37 kDa.

FIG. 17.

HEK293Tcells were transfected with either 25 ng or 50 ng plasmid encoding for the constitutive active mutant of IRF3 (IRF3-5D) or MAVS, together with increasing doses of plasmids expressing IFI16 wildtype. Level of activation was evaluated 24 hrs later by measuring expression of an IFN-β promoter driven Firefly gene normalized to a beta-actin promotor Renilla gene. Data represent the mean±SD of biological triplicates, representative of two independent experiments.

FIG. 18.

STING trafficking from ER localisation to cytosolic puncta was evaluated in control and IFI16 KO cells infused with 50 nM cGAMP for 1 hour. Cells were fixed and stained for DAPI (blue) and STING (red).

FIGS. 19A-19E.

Figure 19A:
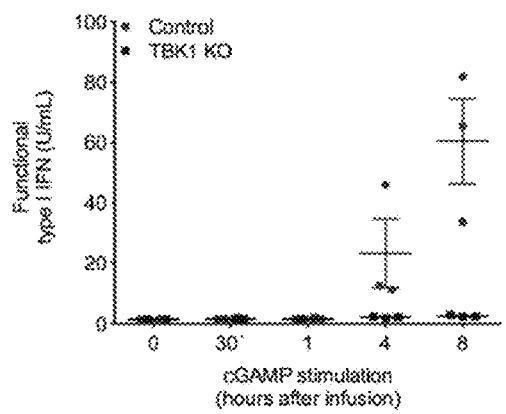
Figure 19B:
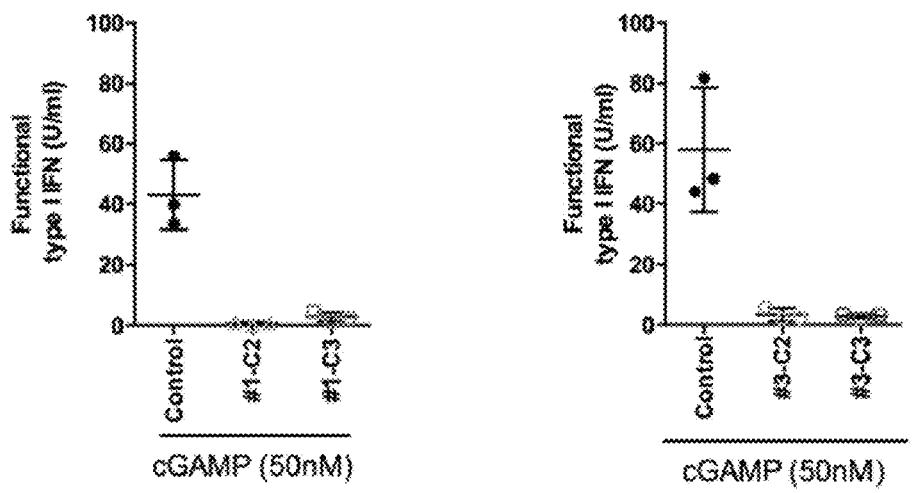
Figure 19C:
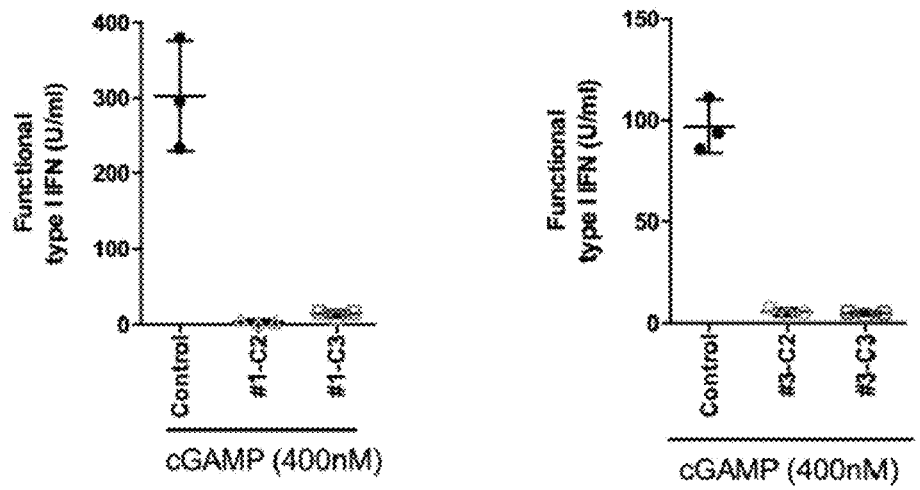

(FIG. 19A) Control and TBK1 KO THP-1 cells were stimulated with cGAMP (50 nM) and type I IFN secretion was evaluated at indicated time points. (FIGS. 19B-19C). Four different PMA-differentiated THP-1 KO clones of IFI16 (see FIG. 9) were infused with (FIG. 19B) 50 nM or (FIG. 19C) 400 nM cGAMP and evaluated for type I IFN induction 20 hrs later. (FIG. 19D) IFI16 gene expression was reconstituted in two THP-1 IFI16 KO clones using lentiviral delivery. Forty-eight hours later cells were infused with cGAMP (50 nM) and evaluated for type I IFN responses after 8 and 20 hrs. (FIG. 19E) Control and IFI16 KO THP-1 cells were infused with low (50 nM) and high doses (400 nM) of cyclic-di-AMP (c-di-AMP) and evaluated for type I IFN induction 20 hrs later.

Data represent the mean±SD of biological triplicates, representative of (FIG. 19A-19C) three and (FIG. 19D-19E) two independent experiments. Unpaired t-test was performed to evaluate the significance. *P<0.05; ** P<0.01.

FIG. 20.

HEK293T$^{STING}$ cells were transfected with either control plasmid (eGFP) or IFI16-wt plasmid at 100 ng/well. Twenty-fours later cells were stimulated with increasing doses of cGAMP infused with digitonin. STING activation was evaluated 24 hrs later by measuring expression of an IFN-b promoter Firefly gene normalized to a beta-actin promotor Renilla gene.

FIG. 21.

Proposed two-step model of the function of IFI16 in regulating the STING signalling events following DNA sensing in human macrophages.

Figure 22:
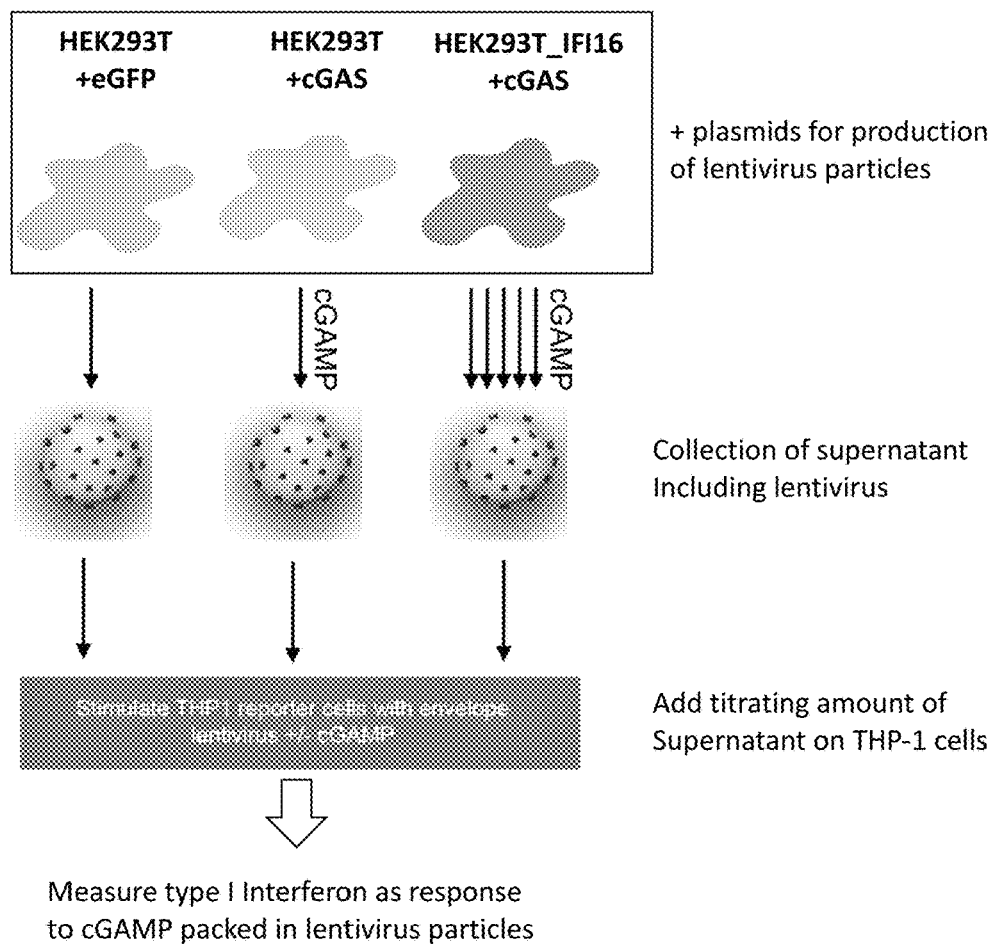

FIG. 22. Illustration of the experimental process of production lentiviral particle carrying cGAMP and verification of their immunological capacity to trigger Interferon production FIG. 23. Evaluation of type I interferon production in THP1 cells stimulated with a low (50 ul) and high (200 ul) inoculum of lentiviral particles produced in HEK293T cells or HEK293T-IFI16 cells.

Figure 24:
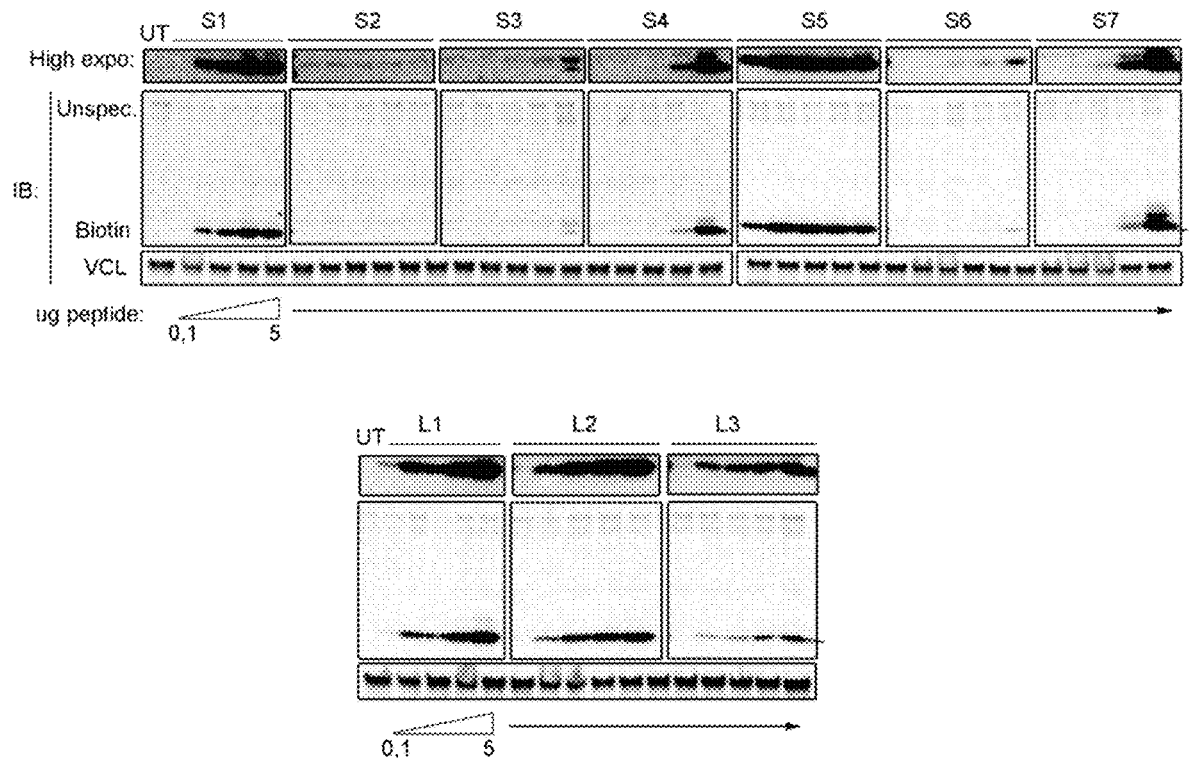

FIG. 24. Uptake in HEK293T cells. Results demonstrate that all peptides are capable of penetrating cells at different degrees.

Figure 25:

FIG. 25. Uptake in human PBMCs. Results demonstrate that all peptides ae able to penetrate PBMCs.

Figure 26:
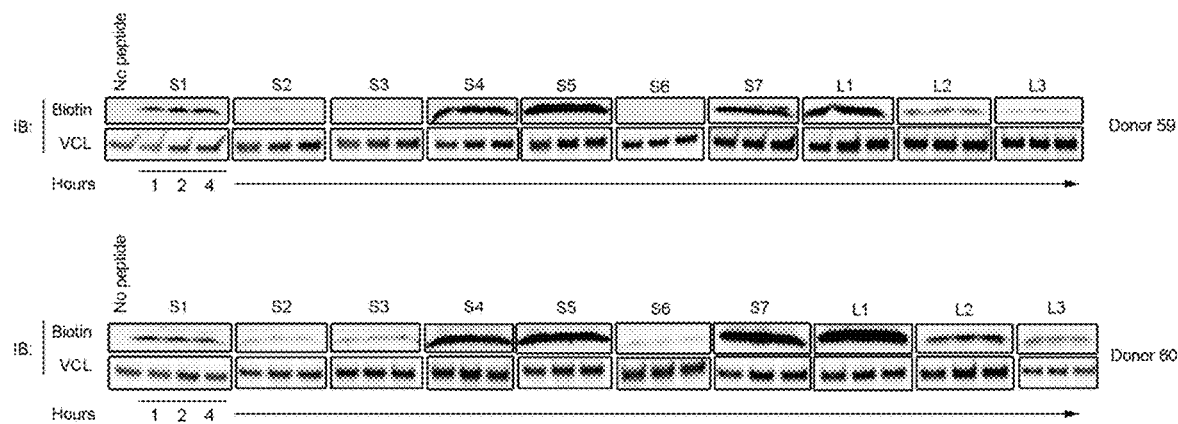

FIG. 26. Uptake in human PBMCs—time kinetics. Results show which peptides show faster uptake and stable expression within the PBMC culture.

Figure 27:
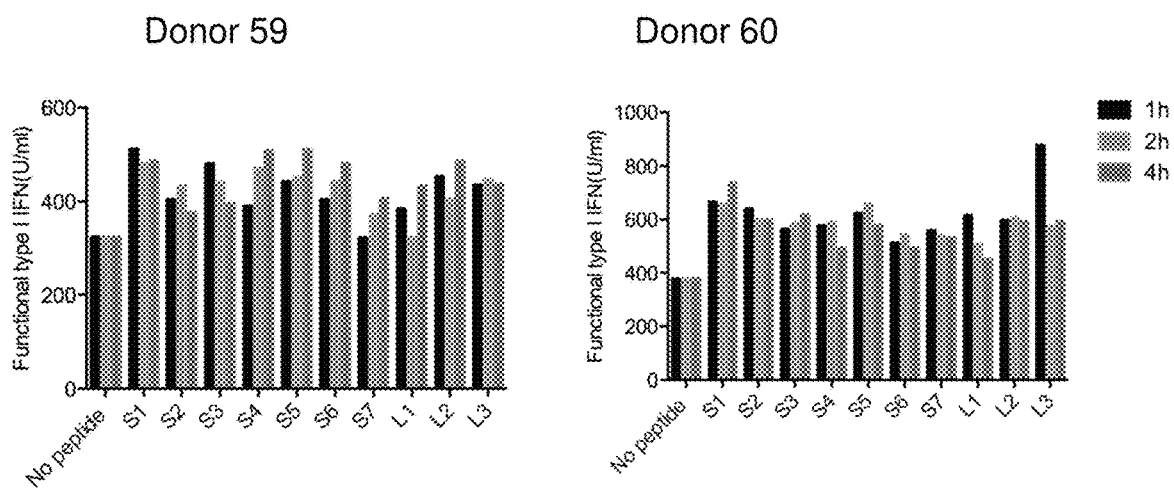
Figure 27:
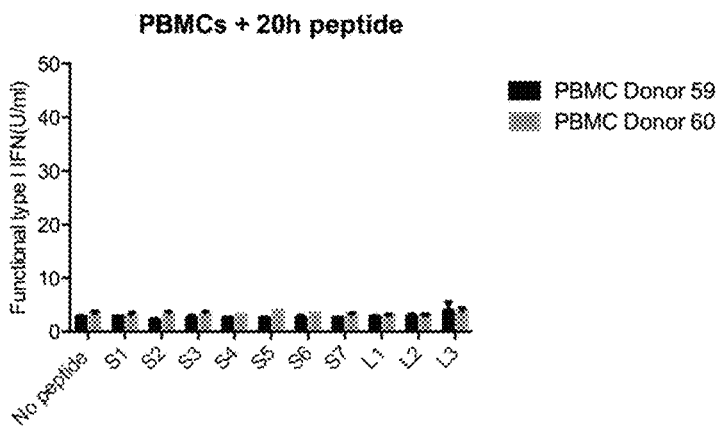

FIG. 27. Stimulation of PBMCs with DNA in combination with peptides. Results demonstrate that PBMCs stimulated with DNA give a robust IFN signal but in combination with most peptides this response increase further. Also, this increased response is dependent on the kinetic of peptide uptake. Furthermore, peptides alone do not lead to any IFN response.

Figure 28:
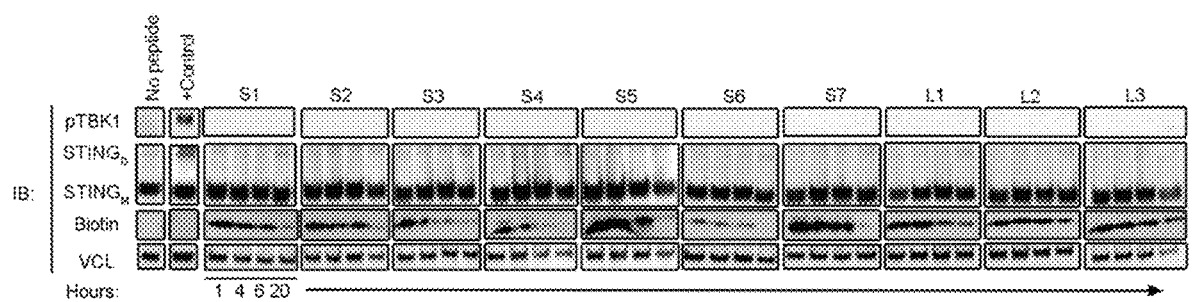

FIG. 28. Stimulation of macrophages (PMA-differentiated THP1 cells) with peptides. Results demonstrate that most peptides are degraded within cells after 20 hrs but also that some peptides lead to a preactivated form of STING (e.g. dimerization of STING=STING$_D$). None of the peptides lead to phosphorylation of TBK1, supporting that peptides alone do not trigger IFN responses.

Figure 29:
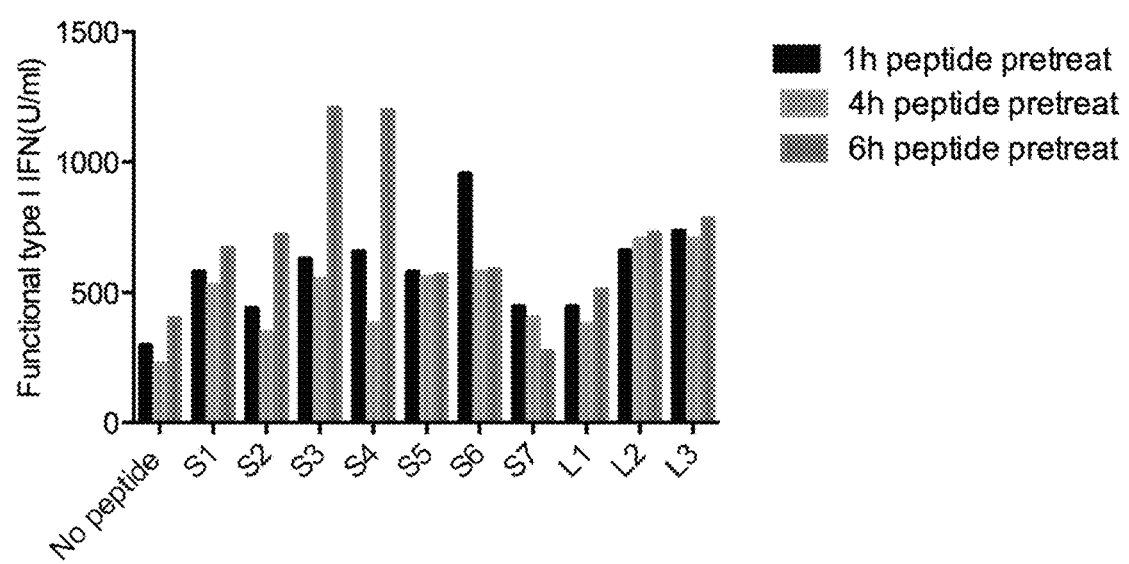

FIG. 29. Stimulation of macrophages (PMA-differentiated THP1 cells) with peptides and cGAMP. Results demonstrate that the best peptides had superior effects on cGAMP stimulation of up to 3 fold enhanced IFN responses compared to cells without peptides.

Figure 30:
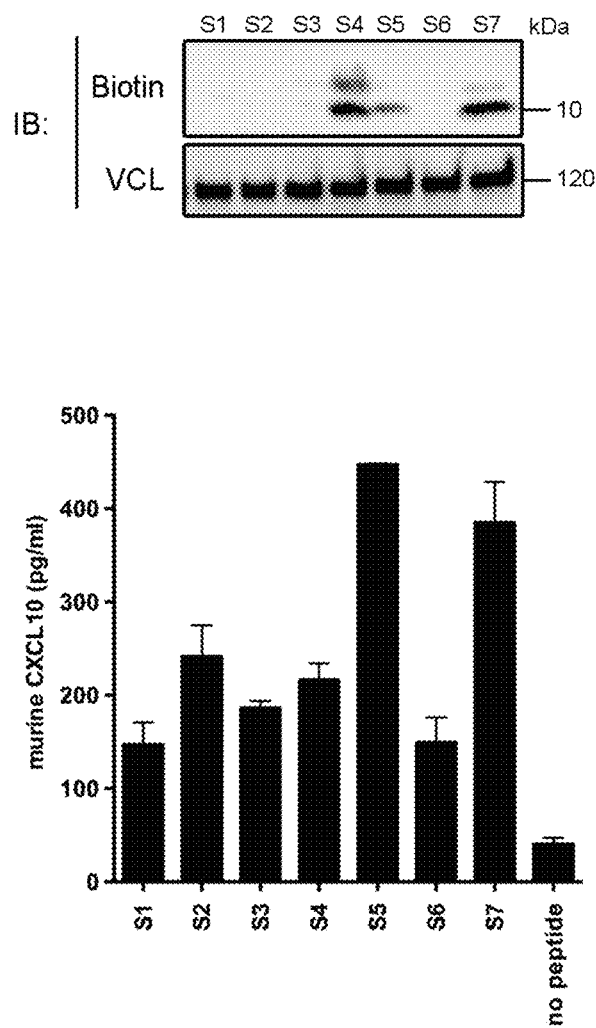

FIG. 30. Stimulation of murine macrophages with peptides and cGAMP. Results show that some peptides had poor stability in the murine macrophage model. However all peptides demonstrated superior enhanced immune responses in combination with cGAMP—measured by CXCL10 secretion.

Figure 31A:
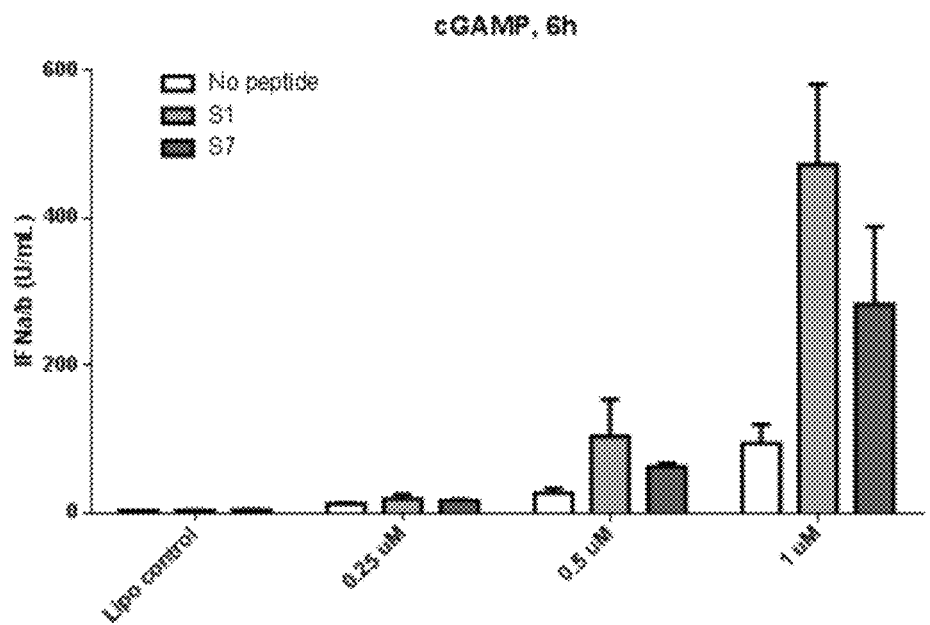
Figure 31B:
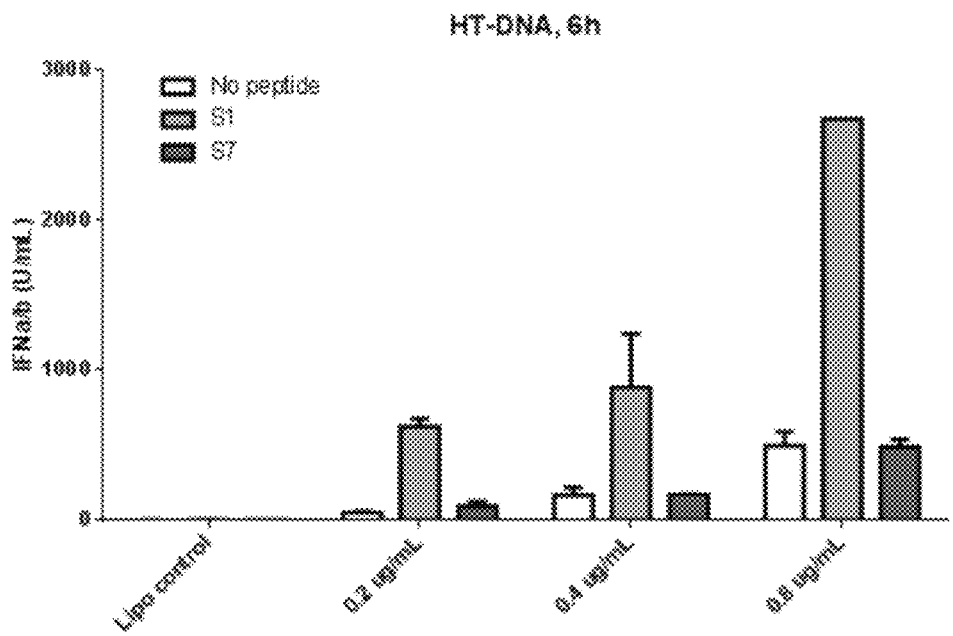
Figure 31C:
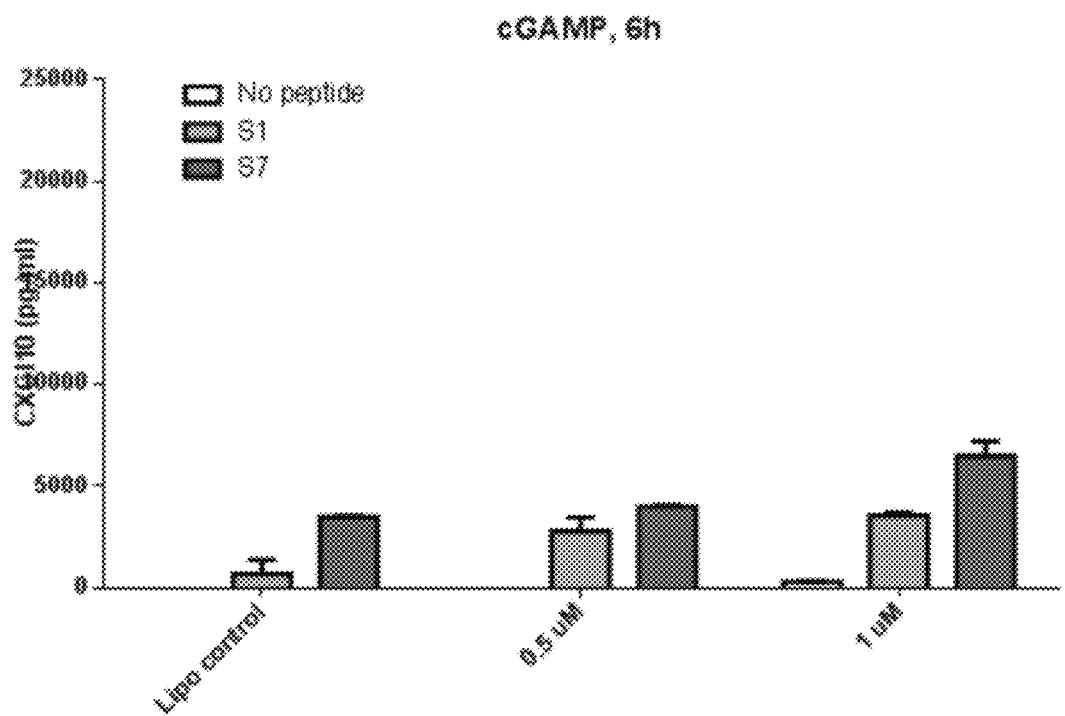
Figure 31D:
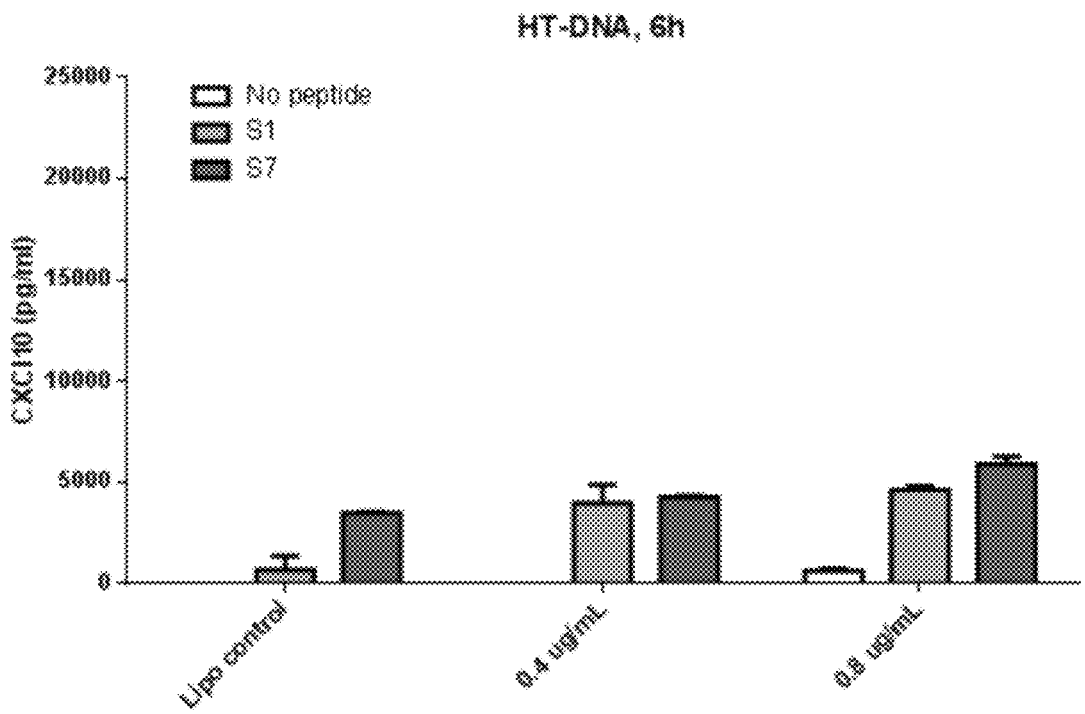

FIGS. 31A-31D. Preactivation of human primary macrophages with specific peptides and co-stimulation with cGAMP (FIG. 31A, 31C) or Herring testis DNA (HT-DNA) (FIG. 31B, 31D). Results show that peptides are able to induce strong immune responses 6 hours post stimulation, measured by type I IFN (FIGS. 31A, 31B) and T-cell recruitment cytokine CXCL10 (FIGS. 31C, 31D).

Figure 32A:
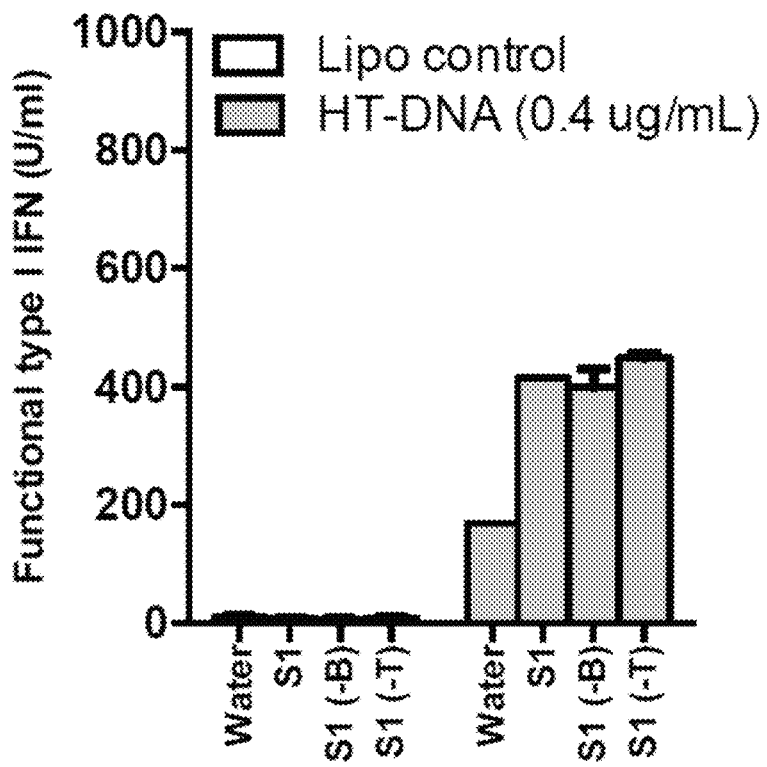
Figure 32B:
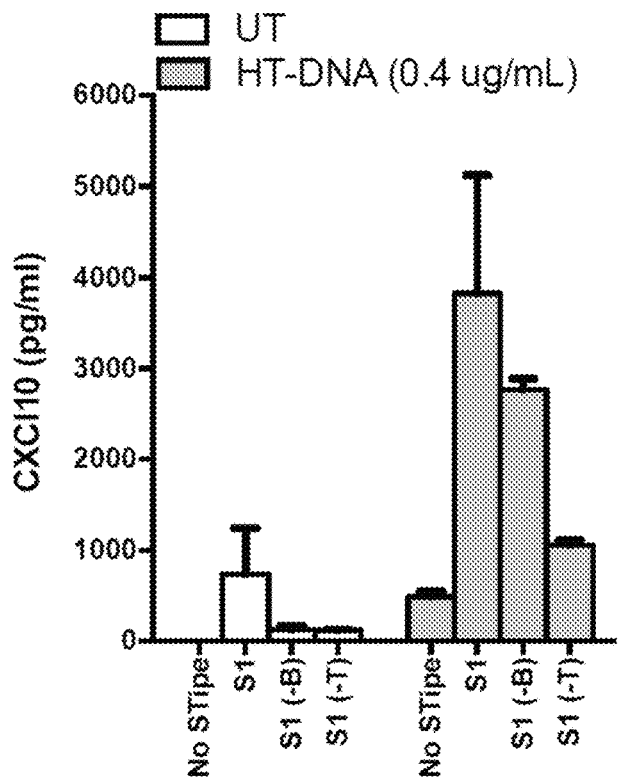

FIGS. 32A-32B. Evaluation of peptide with N- and C-terminus modifications. Results show that peptides without biotin (—B) (SEQ ID NO: 25) is capable of inducing type I IFN (FIG. 32A) and CXCL10 (FIG. 32B) response in humane macrophages co-stimulated with HT-DNA that is significantly higher as compared to none-peptide treated cells. In addition, peptides without biotin (—B) respond in a similar manner as peptides that include both biotin and cell penetrating motif (S1 (SEQ ID NO: 25). Peptides without cell penetrating domain (-T) (SEQ ID NO: 26) but with biotin demonstrate decreased efficacy on CXCL10 production (FIG. 32B) but still strong type I IFN signalling (FIG. 32A).

Figure 33A:
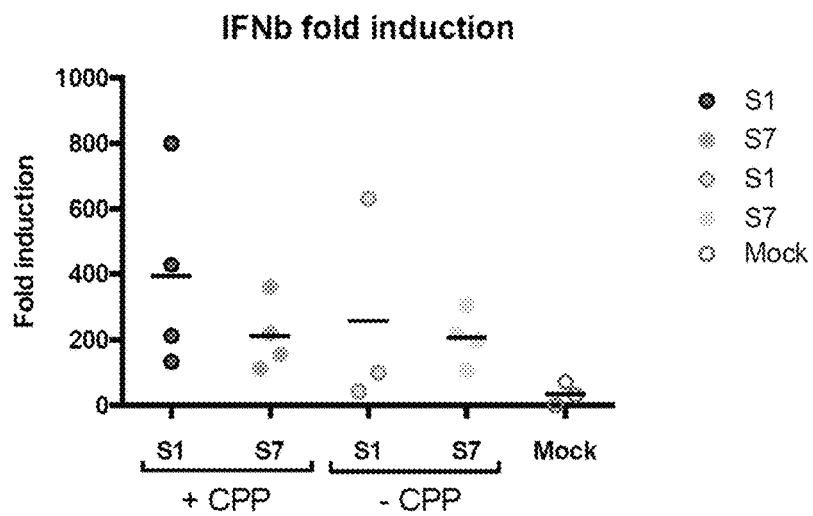
Figure 33B:
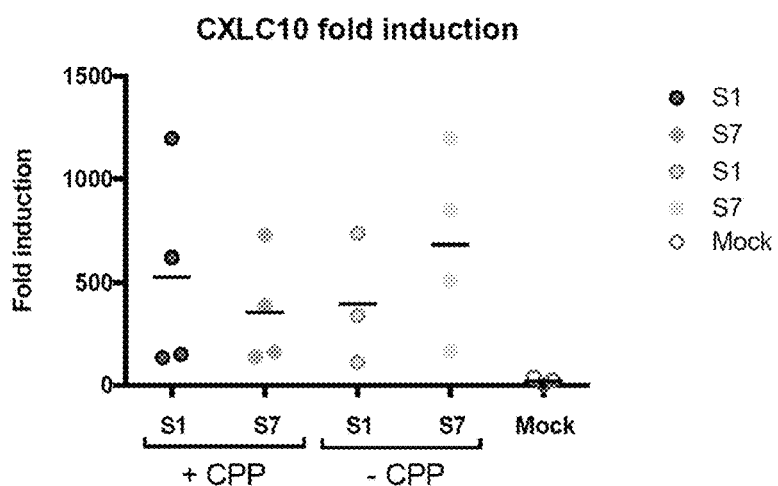
Figure 33C:
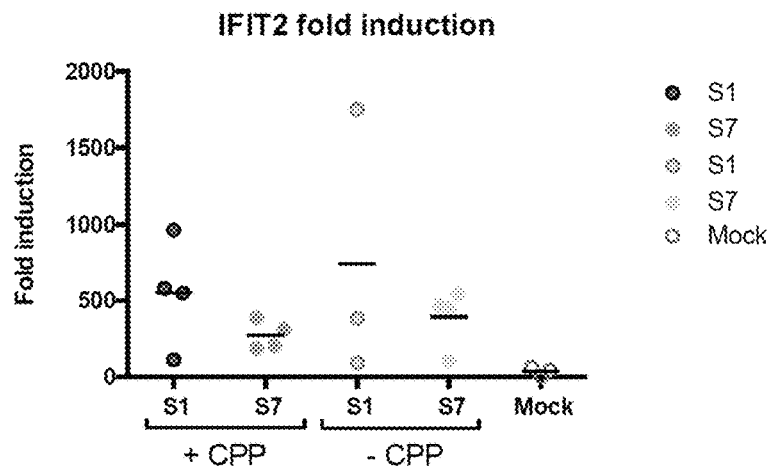

FIGS. 33A-33C. In vivo evaluation of peptides. Results show that subcutaneous injection with low doses of peptides generate strong innate immune activation 6 hours p.i. in C57BL/6J mice, measured by fold induction of IFNb, CXCL10 and IFIT2 mRNA expression. Peptides without cell penetration motif (-CPP) (SEQ ID NO: 26 (S1 (-CPP)) and SEQ ID NO: 28 (S7 (-CPP))) demonstrate similar immune responses as peptides including the motif. Mock treated mice were injected with physiological salt water.

Figure 34:
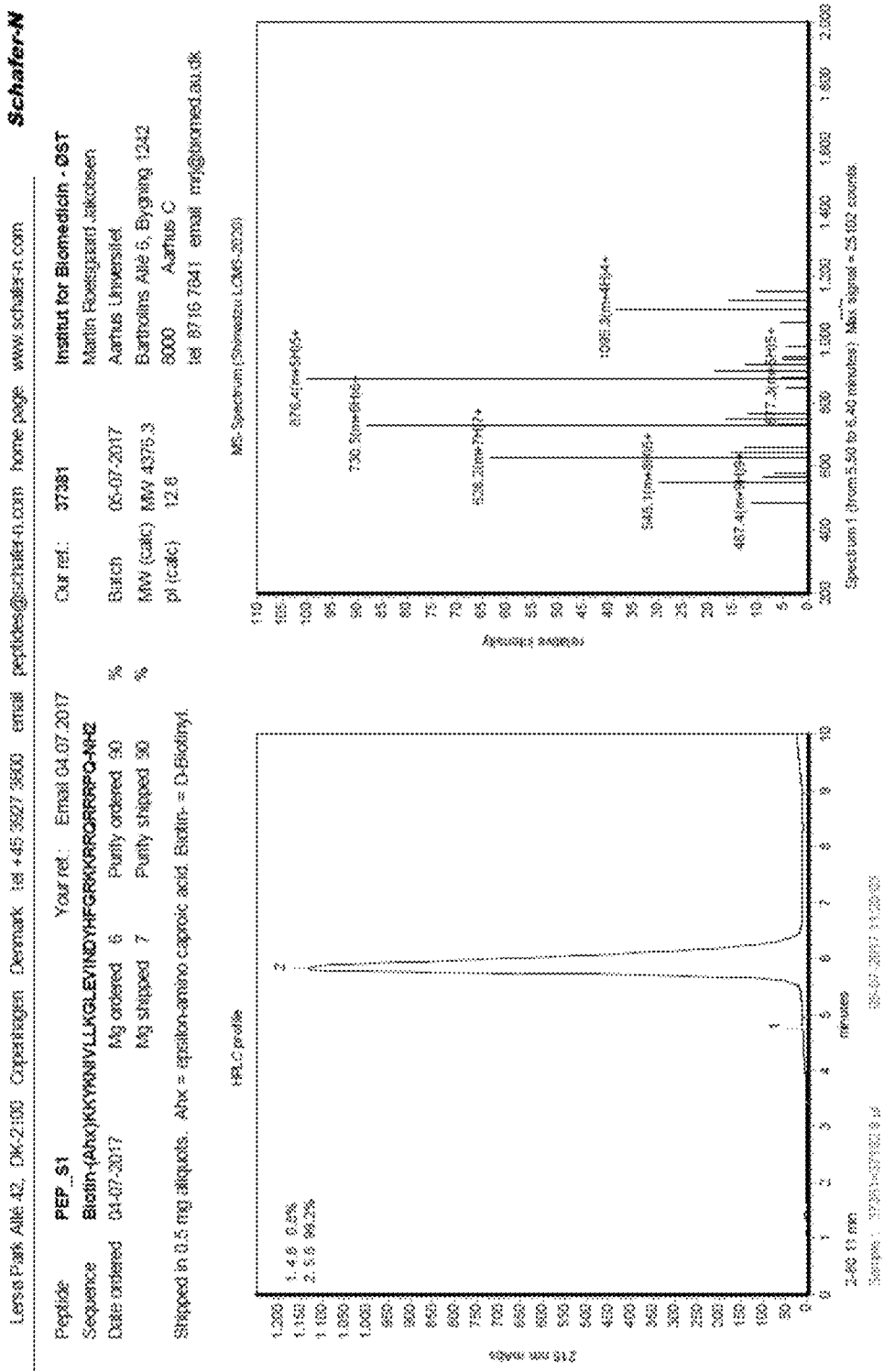

FIG. 34. Specifications for purification of peptide S1 (SEQ ID NO: 15)

DETAILED DESCRIPTION

Definitions

The term "comprising" should be understood in an inclusive manner. Hence, by way of example, a composition comprising compound X, may comprise compound X and optionally additional compounds.

The term "polypeptide" as used herein refers to a chain of amino acid monomers linked by peptide (amide) bonds. Said chain may comprise any number of amino acid monomers, but typically comprise at least 5 amino acids. The polypeptide may comprise any amino acid, however preferably consists of naturally occurring amino acids.

The term "small organic molecules or compounds" refers herein to non-oligomeric, carbon containing compounds producible by chemical synthesis and generally having a size of less than 600 mass units.

Compound Capable of Binding to the Pyrin-Domain of IFI16

The invention relates to compounds capable of binding to the pyrin-domain of IFI16. In particular said compounds may be capable of binding directly to the pyrin-domain of IFI16. In particular, said compound may be a compound, which is capable of inhibiting IFI16 activity and/or STING activity as described herein below in the section "IFI16 activity and STING activity". Such compounds may herein also be referred to "IFI16 pyrin inhibitor" or simply as "compound of the invention".

The IFI16 pyrin inhibitor may be any compound capable of binding to the pyrin-domain of IFI16 or a fragment thereof. The pyrin-domain of IFI16 is described herein below in more detail in the section "IFI16". It is preferred that the compound is capable of selectively binding the pyrin-domain of IFI16, and thus said compound preferably binds the pyrin-domain of IFI16 with at least 10 times higher affinity than to a non-specific polypeptide (e.g. BSA). It may further be preferred that said compound binds the pyrin-domain of IFI16 with higher affinity, e.g, with at least 2× higher affinity than it binds to any other polypeptide.

In some embodiments the compound may be capable of binding the pyrin-domain of IFI16 or a fragment thereof with an affinity corresponding to a $K_D$ of about $10^{-7}$ M or less, such as about $10^{-8}$ M or less, such as about $10^{-9}$ M or less, for example about $10^{-10}$ M or less, or even about $10^{-11}$ M or even less.

The IFI16 pyrin inhibitor may be any kind of compound. In one embodiment the IFI16 pyrin inhibitor is a small molecule interacting with the pyrin-domain of IFI16. The small molecule may in particular be a small organic molecule. Typically, small molecules, such as small organic molecules are molecules of 600 mass units or less.

In another embodiment the IFI16 pyrin inhibitor is a polypeptide. Polypeptides capable of binding to the pyrin-domain of IFI16 may be identified in any useful manner, for example by screening a library of test polypeptides with the pyrin-domain of IFI16 or a fragment thereof for polypeptides capable of binding the pyrin-domain of IFI16. Non-limiting examples of methods for identifying polypeptides capable of binding the pyrin-domain of IFI16 include phage display, phage-display peptide biopanning; pull-down binding competition assays; Fluorescent Resonance Energy Transfer assay (FRET); Biocore analysis; or Database/Bioinformatics based methods.

In one embodiment of the invention the IFI16 pyrin inhibitor is an antibody, an antigen-binding fragment of an antibody or a synthetic antibody specifically binding the pyrin-domain of IFI16 or a fragment thereof.

The antibody may be any antibody. For example, the antibody may be a naturally occurring antibody or a functional homologue thereof. A naturally occurring antibody is a heterotetrameric glycoproteins capable of recognising and binding an antigen comprising two identical heavy (H) chains and two identical light (L) chains inter-connected by disulfide bonds. Each heavy chain comprises or preferably consists of a heavy chain variable region (abbreviated herein as $V_H$) and a heavy chain constant region (abbreviated herein as $C_H$). Each light chain comprises or preferably consists a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs).

The naturally occurring antibody may also be a heavy-chain antibody (HCAbs) as produced by camelids (camels, dromedaries and llamas). HCAbs are homodimers of heavy chains only, devoid of light chains and the first constant domain (Hamers-Casterman et al., 1993).

The naturally occurring antibody according to the invention may for example be selected from the group consisting of IgG, IgM, IgA, IgD and IgE. The subunit structures and three-dimensional configurations of these different classes of immunoglobulins are well known.

Naturally occurring antibodies according to the invention may be antibodies of a particular species, for example the antibody may be a murine, a rat, a rabbit, a goat, a sheep, a chicken, a donkey, a camelid or a human antibody. The antibody according to the invention may however also be a hybrid between antibodies from several species, for example the antibody may be a chimeric antibody, such as a humanised antibody.

The antibody according to the invention may be a monoclonal antibody, such as a naturally occurring monoclonal antibody or it may be polyclonal antibodies, such as naturally occurring polyclonal antibodies.

The antigen binding fragment of an antibody may be any protein or polypeptide containing an antigen binding site. Preferably, the antigen binding site comprises at least one CDR, or more preferably a variable region.

Thus the antigen binding site may comprise a $V_H$ and/or $V_L$. It is preferred that the antigen binding site comprises one or more CDRs, preferably at least 1, more preferably at least 2, yet more preferably at least 3, even more preferably at least 4, yet more preferably at least 5, even more preferably 6 CDRs. It is preferable that the antigen binding site comprises at least one CDR3, more preferably at least the CDR3 of the heavy chain.

The antigen binding fragment of antibody may also be a heterospecific antibody, a single chain antibody or a recombinant antibody. The fragments may also be Fab fragments or scFv.

Synthetic antibodies may for example be recombinant antibodies, nucleic acid aptamers and non-immunoglobulin protein scaffolds.

Recombinant antibodies may be generated in vitro by expression from recombinant genes. The recombinant genes may be based on antibody genes from any species of antibody-producing animal, which optionally may be manipulated to generate new antibodies or antibody fragments, such as Fab fragments and scFv.

Synthetic antibodies may also be non-immunoglobulin derived. Such molecules typically differ in structure to that of an antibody and can for example be generated from nucleic acids, as in the case of aptamers, or from protein scaffolds, for example peptide aptamers, into which hypervariable loops are inserted to form the antigen binding site.

The synthetic antibody may also be an affimer protein, which is a small robust affinity reagents with a molecular weight of 12-14 kDa. Affimers are engineered to bind to their target proteins with high affinity and specificity. The Affimer protein scaffold is derived from the cysteine protease inhibitor family of cystatins, which contains two variable peptide loops and a variable N-terminal sequence, which can be engineered to provide a high affinity binding surface for the pyrin-domain of IFI16.

Pyrin-Domain of IFI16 Analogues

The invention also relates to compounds capable of mimicking the pyrin-domain of IFI16. The term "mimicking", as used herein in relation to the pyrin-domain of IFI16 is meant to indicate that the relevant compound is capable of exerting the same inducing effect of STING activity as IFI16. Such compounds are herein referred to as "pyrin-domain analogues". Preferably, said pyrin-domain analogues are capable of inducing STING activity. Thus, the pyrin-domain analogues may be capable of inducing any of the STING activities described herein below in the section "IFI16 activity and STING activity". In particular, the pyrin-domain analogue may be capable of facilitating interaction between TBK1 and STING.

The pyrin-domain analogues may be any kind of compound. In one embodiment the IFI16 pyrin inhibitor is a small molecule capable of mimicking the pyrin-domain of IFI16. The small molecule may in particular be a small organic molecule. Typically, small molecules, such as small organic molecules are molecules of 600 mass units or less.

Preferably, the pyrin-domain analogue is a polypeptide. Polypeptides capable of inducing STING activity may be identified in any useful manner, for example by screening a library of test polypeptides for polypeptides capable of inducing STING activity.

In preferred embodiments the pyrin-domain analogue is a polypeptide comprising the pyrin-domain of IFI16 or a fragment thereof, wherein said polypeptide optionally may be conjugated to a conjugated moiety, such as at least one conjugated moiety.

In particular, the pyrin-domain analogue may be a polypeptide comprising:

the pyrin-domain of human IFI16 (human pyrin-domain) provided herein as SEQ ID NO:1;

a fragment of said human pyrin-domain consisting of a consecutive sequence of at least 5 amino acids of SEQ ID NO:1; or a functional homologue of the human pyrin-domain sharing at least 70% sequence identity with SEQ ID NO:1, wherein the polypeptide optionally may be conjugated to a conjugated moeity Thus, the invention also relates to polypeptides comprising or consisting of the pyrin-domain of IFI16 or a fragment thereof, wherein said pyrin-domain or fragment thereof may be any of the pyrin-domains or fragments thereof described herein below in the section "IFI16".

Polypeptides comprising the pyrin-domain or a fragment thereof according to the present invention are preferably not too large. Accordingly it may be preferred that such polypeptide consists of at the most 150 amino acids, such as of the most 100 amino, for example at the most 80 amino acids.

In one embodiment, the polypeptide of the present invention is selected from SEQ ID NO: 5-28, as recited herein below, wherein the underlined sequence indicate a conjugated cell penetrating motif:

SEQ ID NO: 5:
KKYKNIVLLKGLEVINDYHF<u>GRKKRRQRRRPQ</u>-NH2

SEQ ID NO: 6:
LEVINDYHFRMVKSLLSNDL<u>GRKKRRQRRRPQ</u>-NH2

SEQ ID NO: 7:
LLSNDLKLNLKMREEYDKIQ<u>GRKKRRQRRRPQ</u>-NH2

SEQ ID NO: 8:
EEYDKIQIADLMEEKFRGD<u>GRKKRRQRRRPQ</u>-NH2

SEQ ID NO: 9:
DLMEEKFRGDAGLGKLIKIF<u>GRKKRRQRRRPQ</u>-NH2

SEQ ID NO: 10:
AGLGKLIKIFEDIPTLEDLA<u>GRKKRRQRRRPQ</u>-NH2

SEQ ID NO: 11:
EDIPTLEDLAETLKKEKLK<u>GRKKRRQRRRPQ</u>-NH2

-continued

SEQ ID NO: 12:
NDLKLNLKMREEYDKIQIADLMEEKFRGDAGLGKLIKIFEDIPTLEDLAE
TLKKEKLK<u>GRKKRRQRRRPQ</u>-NH2

SEQ ID NO: 13:
KKYKNIVLLKGLEVINDYHFRMVKSLLSNDLKLNLKMREEYDKIQIADLM
EEKF<u>GRKKRRQRRRPQ</u>-NH2

SEQ ID NO: 14:
HFRMVKSLLSNDLKLNLKMREEYDKIQIADLMEEKFRGDAGLGKLIKIFE
<u>GRKKRRQRRRPQ</u>-NH2

SEQ ID NO: 15:
S1: Biotin-KKYKNIVLLKGLEVINDYHF<u>GRKKRRQRRRPQ</u>-NH2

SEQ ID NO: 16:
S2: Biotin-LEVINDYHFRMVKSLLSNDL<u>GRKKRRQRRRPQ</u>-NH2

SEQ ID NO: 17:
S3: Biotin-LLSNDLKLNLKMREEYDKIQ<u>GRKKRRQRRRPQ</u>-NH2

SEQ ID NO: 18:
S4: Biotin-EEYDKIQIADLMEEKFRGD<u>GRKKRRQRRRPQ</u>-NH2

SEQ ID NO: 19:
S5: Biotin-DLMEEKFRGDAGLGKLIKIF<u>GRKKRRQRRRPQ</u>-NH2

SEQ ID NO: 20:
S6: Biotin-AGLGKLIKIFEDIPTLEDLA<u>GRKKRRQRRRPQ</u>-NH2

SEQ ID NO: 21:
S7: Biotin-EDIPTLEDLAETLKKEKLK<u>GRKKRRQRRRPQ</u>-NH2

SEQ ID NO: 22:
L1: Biotin-
NDLKLNLKMREEYDKIQIADLMEEKFRGDAGLGKLIKIFEDIPTLEDLAE
TLKKEKLK<u>GRKKRRQRRRPQ</u>-NH2

SEQ ID NO: 23:
L2: Biotin-
KKYKNIVLLKGLEVINDYHFRMVKSLLSNDLKLNLKMREEYDKIQIADLM
EEKF<u>GRKKRRQRRRPQ</u>-NH2

SEQ ID NO: 24:
L3: Biotin-
HFRMVKSLLSNDLKLNLKMREEYDKIQIADLMEEKFRGDAGLGKLIKIFE
<u>GRKKRRQRRRPQ</u>-NH2

The polypeptide may optionally be additionally conjugated to at least one moiety. The at least one conjugated moieties can be attached at the N-terminus or the C-terminus or even to an amino acid sidechain of the polypeptide.

In one embodiment the conjugated moiety is a peptide, a sugar, a lipid, a cell-penetrating peptide (CPP) or any other chemical group that can be covalently linked to a polypeptide. The conjugated moiety may also improve physical properties of the polypeptide, such as its solubility, stability or half-life. In one embodiment, the conjugated moiety is a detectable moiety that could be used for imaging of the polypeptide; for example, the conjugated moiety is a biotin molecule. Specifically, the polypeptide may be conjugated to one or more fatty acids or fatty acid-like moieties in order to prolong in vivo half-life.

In one embodiment, the conjugated moiety may be a compound that masks the polypeptide from the host immune system, such as a polyethylene glycol (PEG) polymer chain or a modified PEG, for example NPEG. PEG or modified PEG may also prolong the in vivo half-life of the peptide.

In one embodiment, the polypeptide comprises an N-terminal biotin conjugated moiety and a C-terminal CPP conjugated moiety.

In one preferred embodiment, the polypeptide comprises a C-terminal CPP conjugated moiety.

IFI16

Interferon-gamma-inducible protein 16 (IFI16) is a cytosolic and nuclear protein also known as interferon-inducible myeloid differentiation transcriptional activator. In humans IFI16 is encoded by the IFI16 gene, and the amino acid sequence of human IFI16 is provided herein as SEQ ID NO:2.

IFI16 contains several domains including a pyrin-domain, 2 HIN domains (HIN-A and HIN-B) and a BFP domain. An overview of the domain structure of IFI16 is provided herein in FIG. 5H. Three isoforms of IFI16 exists, which are generated by alternative splice sites. All three isoforms contain the Pyrin and HIN domains. The present invention relates to pyrin-domain analogues e.g. polypeptides comprising or consisting of the pyrin-domain of IFI16, as well as to compounds capable of binding the pyrin-domain of IFI16.

In human IFI16 the pyrin-domain is positioned at aa 10 to 88 of SEQ ID NO:2. Pyrin-domains of other IFI16 proteins can be determined by aligning the IFI16 to human IFI16 of SEQ ID NO:2 and identifying the amino acids corresponding to amino acid 10 to 88 of SEQ ID NO:2.

The pyrin-domain of IFI16 may in particular be the pyrin-domain of human IFI16. The amino acid sequence of human IFI16 is provided herein as SEQ ID NO:1.

The pyrin-domain of IFI16 may however also be a functional homologue of the pyrin-domain of human IFI16 sharing at least 70%, such as at least 75%, for example at least 80%, such as at least 85%, for example at least 90% m, such as at least 95%, for example at least 98% sequence identity with SEQ ID NO:1. A functional homologue of the pyrin-domain of human IFI16 preferably has one or more of the activities of the IFI16 described herein below in the section "IFI16 activity and STING activity".

The invention also relates to fragments of the pyrin domain of IFI16 as well as to compounds binding such fragments. Fragments of the pyrin-domain of IFI16 may be any fragment of any of the pyrin domains described above. Typically, the fragments comprise at least 5 consecutive amino acids of a pyrin-domain of IFI16.

In one embodiment, the fragment comprise at least 5, such as at least 10, for example at least 15, such as at least 20, for example in the range of 5 to 70, such as in the range of 5 to 60, for example in the range of 5 to 50, such as in the range of 10 to 70, for example in the range of 10 to 60, such as in the range of 10 to 50 consecutive amino acids of the pyrin-domain of human IFI16 of SEQ ID NO:1.

In another embodiment, the fragment comprise at least 5, such as at least 10, for example at least 15, such as at least 20, for example in the range of 5 to 70, such as in the range of 5 to 60, for example in the range of 5 to 50, such as in the range of 10 to 70, for example in the range of 10 to 60, such as in the range of 10 to 50 consecutive amino acids of a functional homologue of the pyrin-domain of human IFI16 of SEQ ID NO:1.

It may be preferred that aforementioned fragments of the pyrin-domain of IFI16 also retain one or more of the activities of IFI16 described herein below in the section "IFI16 activity and STING activity".

Polypeptides

In generally preferred embodiments, the "IFI16 pyrin inhibitor" and/or "pyrin-domain analogues" as defined herein above are polypeptides. In a preferred embodiment, the polypeptide is selected from the group consisting of SEQ ID NO: 5-28, as described elsewhere herein.

In certain embodiment, the polypeptides additionally comprise one or more conjugated moieties. For example, the polypeptide may comprise an N- or C-terminal biotin moiety. In preferred embodiments, the polypeptide comprises a cell-penetrating peptide (CPP), which can be attached to the N- or C-terminus of a polypeptide of the invention or even attached to one or more side chains. Cell-penetrating peptides (CPPs) are short peptides that facilitate cellular intake/uptake of the IFI16 pyrin inhibitor and/or pyrin-domain analogues of the present invention. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. CPPs can mediate cell penetration through different pathways, such as be direct penetration, endocytosis-mediated translocation, or translocation through the formation of a transitory structure (e.g. inverted micelles).

In one preferred embodiment, the CPP is the HIV TAT sequence or a modification thereof.

Peptides of the present invention may be manufactured by standard chemical synthetic methods, or by using recombinant expression systems, or by any other suitable state-of-the-art method. Thus, the peptides of the invention may be synthesized in a number of ways, including, inter alia, methods comprising:

(a) synthesizing the peptide by means of solid-phase or liquid-phase methodology, either stepwise or by fragment assembly, and isolating and purifying the final peptide product; or (b) expressing a nucleic acid construct that encodes the peptide in a host cell, and recovering the expression product from the host cell culture; or (c) effecting cell-free in vitro expression of a nucleic acid construct that encodes the peptide, and recovering the expression product;

or employing any combination of methods as in (a), (b) and (c) to obtain fragments of the peptide, subsequently joining (e.g., ligating) the fragments to obtain the complete peptide, and recovering the peptide.

It may be preferable to synthesize compounds of the invention by means of solid-phase or liquid-phase peptide synthesis, the methodology of which is well known to persons of ordinary skill in the art of peptide synthesis. Reference may also be made in this respect to, for example, Fields, G. B. et al., 2002, "Principles and practice of solid-phase peptide synthesis" in: Synthetic Peptides (2nd Edition), and examples provided therein.

In one embodiment, the polypeptides are synthesized on a peptide synthesizer using standard Fmoc-peptide synthesis, using HBTU as activator and N-methylmorpholine as the tertiary amine during activations. NMP (n'-methyl pyrrolidone) may be used as solvent. The coupling times may be approximately 1 h at RT. The peptides may also be side-chain deprotected in TFA:EDT:TIPS:H2O 94:2:1:3. After precipitation in diethyl ether, the peptides should be dissolved, e.g. in H2O, and purified on a C18-column in water acetonitrile gradients containing 0.1% TFA. Choice of resin is within the capabilities of those of skill in the art, however, a preferred suitable resin is resin polystyrene aminomethyl-resin, which is preferable derivatized with a Rink-amide linker. Polypeptides are preferably provided with at least 90% purity.

Administration

Pharmaceutical compositions of the invention may be administered to a patient in need of such treatment at various sites, for example administration at sites which bypass absorption, such as in an artery or vein or in the brain, and at sites which involve absorption, such as in the skin, under the skin, in a muscle or in the abdomen. More generally, administration of pharmaceutical compositions according to the invention may be by a variety of routes of administration, such as for example parenteral, intracranial, epidermal, dermal or transdermal routes. In some embodiments, other routes such as lingual, sublingual, buccal, oral, vaginal or rectal may be useful. Parenteral administration (of a pharmaceutical composition of the invention) may be performed, for example, by subcutaneous, intramuscular, intraperitoneal or intravenous injection by means of a syringe, for example a pen-like syringe. Alternatively, parenteral administration can take place by means of an infusion pump, e. g. in the form of a device or system borne by a subject or patient and advantageously comprising a reservoir containing a liquid composition of the invention and an infusion pump for delivery/administration of the composition to the subject or patient, or in the form of a corresponding miniaturized device suitable for implantation within the body of the subject or patient.

IFI16 Activity and STING Activity

The invention relates to pyrin-domain analogues, e.g. polypeptides comprising the pyrin-domain of IFI16 or fragments thereof. Said pyrin-domain of IFI16 or fragments thereof preferably has one or more of the IFI16 activities described in this section.

The invention also relates to compounds capable of binding the pyrin-domain of IFI16. Preferably said compounds are capable of inhibiting one or more of the IFI16 activities described in this section.

The invention demonstrates that IFI16 is capable of interacting with the TANK-binding kinase 1 (TBK1). The amino acid sequence of human TBK1 is provided herein as SEQ ID NO:3.

In one embodiment of the invention it is preferred that the pyrin-domain of IFI16 as well as fragments thereof are capable of interacting with TBK1. It is also preferred that IFI16 pyrin inhibitors are capable of inhibiting or at least reducing interaction between IFI16 and TBK1. Reduction of interaction is preferably at least a 2-fold reduction of the interaction. Interaction with TBK1 may for example be determined by immunoprecipitation of IFI16, the pyrin-domain of IFI16 or fragments thereof using antibodies to IFI16 or said fragments, and subsequent detection of TBK1 precipitating with IFI16 or fragments thereof, e.g. by Western blotting with antibodies to TBK1. The interaction may also be performed in the reverse manner, by immunoprecipitation of TBK1 using antibodies to TBK1, and subsequent detection of IFI16, the pyrin-domain of IFI16 or a fragment thereof precipitating with TBK1, e.g. by Western blotting. One non-limiting example of determining interaction between IFI16 and TBK1 is described herein below in Example 1 in the section "IFI16 recruits TBK1 to STING to initiate IRF3 activation".

The invention demonstrates that IFI16 is capable of interacting with the endoplasmic reticulum-bound protein stimulator of interferon genes (STING). The amino acid sequence of human STING is provided herein as SEQ ID NO:4.

In one embodiment of the invention it is preferred that the pyrin-domain of IFI16 as well as fragments thereof are capable of interacting with STING. It is furthermore, preferred that said pyrin-domain of IFI16 as well as fragments thereof are capable of increasing STING activity. It is also preferred that IFI16 pyrin inhibitors are capable of inhibiting or at least reducing interaction between IFI16 and STING. Reduction of interaction is preferably at least a 2-fold reduction of the interaction. Interaction with STING may for example be determined by immunoprecipitation of IFI16, the pyrin-domain of IFI16 or fragments thereof using antibodies to IFI16 or said fragments, and subsequent detection of STING precipitating with IFI16 or fragments thereof, e.g. by Western blotting with antibodies to STING. The interaction may also be performed in the reverse manner, by immunoprecipitation of STING using antibodies to STING, and subsequent detection of IFI16, the pyrin-domain of IFI16 or a fragment thereof precipitating with STING, e.g. by Western blotting. One non-limiting example of determining interaction between IFI16 and STING is described herein below in Example 1 in the section "IFI16 recruits TBK1 to STING to initiate IRF3 activation".

The invention also demonstrates that IFI16 is capable recruiting TBK1 to STING. In one embodiment of the invention it is preferred that the pyrin-domain of IFI16 as well as fragments thereof are capable of facilitating interaction between TBK1 and STING. It is also preferred that IFI16 pyrin inhibitors are capable of inhibiting or at least reducing interaction between TBK1 and STING. Reduction of interaction is preferably at least a 2-fold reduction of the interaction. Interaction between TBK1 and STING may for example be determined by immunoprecipitation of TBK1 using antibodies to TBK1, and subsequent detection of STING precipitating with TBK1, e.g. by Western blotting with antibodies to STING. The interaction may also be performed in the reverse manner, by immunoprecipitation of STING using antibodies to STING, and subsequent detection of TBK1 precipitating with STING, e.g. by Western blotting. One non-limiting example of determining interaction between IFI16 and STING is described herein below in Example 1 in the section "IFI16 recruits TBK1 to STING to initiate IRF3 activation".

The invention also demonstrates that the pyrin domain of IFI16 is involved in STING activation through direct binding of cyclic-di-nucleotides (CDNs). In one embodiment of the invention it is preferred that the pyrin-domain of IFI16 as well as fragments thereof are capable of inducing STING activation, in particular the pyrin-domain of IFI16 as well as fragments thereof are capable of inducing STING activation in the presence of CDNs. It is also preferred that IFI16 pyrin inhibitors are capable of inhibiting or at least reducing STING activation e.g. following the "introduction of" or "stimulation with" CDNs or any small molecule derived of or similar to CDNs.

STING activation may be determined in a number of different ways including the following:

STING activation may be determined by determining STING phosphorylation. Thus, it may be preferred that the pyrin domain of IFI16 or fragments thereof are capable of inducing phosphorylation of STING, e.g inducing an at least 2 fold increase in phosphorylation of STING. It is also preferred that IFI16 pyrin inhibitors are capable of inhibiting or at least reducing phosphorylation of STING. Thus, preferably said IFI16 pyrin inhibitors are capable of reducing phosphorylation of STING at least 2-fold. Said phosphorylation of STING may in particular be phosphorylation of Ser$^{366}$ of STING of SEQ ID NO:4.

Phosphorylation of STING, and particularly phosphorylation of Ser$^{366}$ of STING of SEQ ID NO:4 may be determined in any useful manner, for example as described herein below in Example 1 in the section "The IFI16 PYRIN domain is essential for promoting cGAMP-mediated STING signalling".

STING activation may also be determined as activation of expression of type I IFN or inflammatory cytokines in cells capable of expressing type I IFN or cytokines. Examples of such cells include macrophages, dendritic cells, keratinocytes, fibroblasts, monocytes, epithelia cells, B cells, or NK cells. Thus, STING activation may be determined by determining expression of type I IFN or cytokines in such cells. Thus, it may be preferred that the pyrin domain of IFI16 or fragments thereof are capable of inducing expression of type I IFN or cytokines in such cells, e.g. inducing an at least 2 fold increase in expression of type I IFN in such cells, e.g. in macrophages. It is also preferred that IFI16 pyrin inhibitors are capable of inhibiting or at least reducing expression of type I IFN or cytokines in such cells, e.g. in macrophages. Thus, preferably said IFI16 pyrin inhibitors are capable of reducing expression of type I IFN or of cytokines from such cells, e.g. macrophages by at least 2-fold.

Expression of type I IFN or cytokines may be determined by any useful manner, for example as described herein below in Example 1.

STING activation may also be determined as activation of IFNβ promoter activity. Thus, it may be preferred that the pyrin domain of IFI16 or fragments thereof are capable of activating IFNβ promoter activity, e.g inducing an at least 2 fold increase in IFNβ promoter activity. It is also preferred that IFI16 pyrin inhibitors are capable of inhibiting or at least reducing activity of the IFNβ promoter. Thus, preferably said IFI16 pyrin inhibitors are capable of reducing activity of the IFNβ promoter by at least 2-fold.

Activity of the IFNβ promoter may for example be determined in recombinant cells comprising a nucleic acid construct encoding a reporter protein under the control of the IFNβ promoter. IFNβ promoter can also be determined in cell free expression systems allowing expression of a reporter protein under the control of the IFNβ promoter. A non-limiting useful method for determining IFNβ promoter activity is described herein below in Example 1 in the section "The IFI16 PYRIN domain is essential for promoting cGAMP-mediated STING signalling".

In one embodiment of the invention it is preferred that the pyrin-domain of IFI16 as well as fragments thereof are capable of binding to the caspase recruitment domain (CARD), which is contained in different proteins including the apoptotic speck protein (ASC). It is also preferred that the IFI16 pyrin inhibitors of the invention are capable of inhibiting or at least reducing interaction between IFI16 and CARD containing proteins, such as ASC. Reduction of interaction is preferably at least a 2-fold reduction of the interaction. Interaction between IFI16 and CARD containing proteins such as ASC may for example be determined by immunoprecipitation of either protein or a fragment thereof, and subsequent detection of co-precipitating of the other protein. ASC is an adaptor protein necessary for the assemble of the IFI16 inflammasome, and accordingly IFI16 pyrin inhibitors may block inflammasome mediated by CARD containing proteins such as ASC.

Method of Identifying

In one embodiment the invention relates to a method of identifying a compound capable of binding the pyrin-domain of IFI16, said method comprising the steps of providing a pyrin-domain of IFI16 or a fragment thereof providing a library of test compounds contacting the pyrin-domain of IFI16 with said test compounds detecting and isolating test compounds, which interact with the pyrin-domain of IFI16 or the fragment thereof thereby identifying a compound capable of binding the pyrin-domain of IFI16. Said compound may be useful as an anti-inflammatory agent, as an inhibitor of STING or as an I-IFN antagonist.

Said pyrin-domain of IFI16 or fragment thereof may be any of the pyrin-domains of IFI16 or fragments thereof described herein above in the section "IFI16".

The test compounds may be any of kind of compound, for example the test compounds may be selected from the group consisting of peptides, small organic molecules, antibodies, antigen binding fragments of antibodies and synthetic antibodies, for example any of the peptides, small organic molecules, antibodies, antigen binding fragments of antibodies and synthetic antibodies described herein above in the section "Compound capable of binding to the pyrin-domain of IFI16".

In one embodiment the invention relates to a method of identifying a compound capable of mimicking the pyrin-domain of IFI16, said method comprising the steps of providing a library of test compounds testing whether said test compounds are capable of inducing STING activity thereby identifying a compound capable of mimicking IFI16.

The test compounds may be any of kind of compound, for example the test compounds may be selected from the group consisting of polypeptides and small organic molecules, for example any of the polypeptides and small organic molecules described herein above in the section "Pyrin-domain of IFI16 analogues".

The libraries may comprise any suitable number of test compounds, for example at least 100 different test compounds, such as 1000 different test compounds, for example at least 10,000 different test compounds, such as 100,000 different test compounds.

The libraries may be in any useful format. Thus, the library may simply be a mixture of compounds. When the test compounds are peptides, then the library may be in form of organisms, vira or phages expressing the test compounds. It is also possible that the test compounds of the library are spatially separated from each other to allow easy identification of the compound(s) capable of binding the pyrin-domain of IFI16 or a fragment thereof. Spatial separation may be achieved in a number of ways, for example by use of small containers, such a microtiter plates or the test compounds of the library may be immobilised on solid support.

Disorder Associated with STING Activity

In one embodiment, the invention relates to compounds capable of binding to the pyrin-domain of IFI16 or a fragment thereof for use in the treatment of a disorder associated with STING activity. Said compounds may for example be any of the compounds described herein above in the section "Compound capable of binding the pyrin-domain of IF16, in particular the compound may be any of the IFI16 pyrin inhibitors described herein.

The disorder associated with STING activity may for example be a disorder characterised with by increased STING activity or by undesired STING activity. Said STING activity may for example be any of the activities described herein above in the section "IFI16 activity and STING activity". The disorder may also be associated with TBK1 activity.

Numerous disorders have been associated with STING activity for example as described in any of the following references: STING-mediated DNA sensing promotes antitumor and autoimmune responses to dying cells. http://www.ncbi.nlm.nih.gov/pubmed/25385820

STING Promotes the Growth of Tumors Characterized by Low Antigenicity via IDO Activation. http://www.ncbi.nlm.nih.gov/pubmed/26964621

Intrinsic Self-DNA Triggers Inflammatory Disease Dependent on STING. http://www.jimmunol.org/content/193/9/4634.long STING Activation by Translocation from the ER Is Associated with Infection and Autoinflammatory Disease. http://www.ncbi.nlm.nih.gov/pubmed/26235147

Activation of cyclic GMP-AMP synthase by self-DNA causes autoimmune diseases. http://www.ncbi.nlm.nih.gov/pubmed/26371324

Therapeutic potential of targeting TBK1 in autoimmune diseases and interferonopathies. http://www.ncbi.nlm-.nih.gov/pubmed/27353409

In one embodiment the disorder associated with STING activity is an inflammatory disorder. Said inflammatory disorder may for example be selected from the group consisting of psoriasis, Crohn's disease and Inflammatory bowel disease (IBD).

In one embodiment the disorder associated with STING activity is an auto-immune disease. Said autoimmune disease may for example be selected from the group consisting of systemic lupus erythematosus (SLE), Aicardi-Goutieres syndrome, Sjogren's syndrome, STING-associated vasculopathy with onset in infancy (SAVI), Type 1 diabetes and multiple sclerosis.

The disorder may also be both an inflammatory disorder and an auto-immune disease. Thus, many auto-immune diseases are also inflammatory disorders.

In one embodiment of the invention the disorder associated with STING activity is cancer. In particular, said cancer may be a cancer induced by chronic inflammatory signalling. However, cancer types, which are not related to chronic inflammatory signaling, are also relevant targets for treatment. For example said cancer may be a cutaneous skin tumour, for example basal cell (BCC) or squamous cell carcinoma (SCC).

Disorder Associated with Insufficient STING Activity

In one embodiment the invention relates to a polypeptide comprising or consisting of the pyrin-domain of IFI16 or a fragment thereof for use in the treatment of a disorder associated with insufficient STING activity.

As demonstrated by the present invention, the pyrin-domain of IFI16 or a fragment thereof may induce STING activity. Accordingly, the pyrin-domain of IFI16 or fragments thereof may be useful for treating disorders associated with insufficient STING activity. Useful pyrin-domains of IFI16 or fragments thereof are described above in the section "IFI16".

In one embodiment the disorder is cancer. Cancer (malignant neoplasm) is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). Most cancers form a tumor but some, like leukemia, do not.

Thus, the disorder may be cancer, for example a cancer selected from the group consisting of: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

The disorder may also be an infection with DNA pathogens, where IFN is deleterious. Such disorders include for example malaria or listeria.

Method of Treatment and Combination Therapy

As described herein the invention in some embodiments relates to compounds capable of binding the pyrin-domain of IFI16, as well as to pyrin-domain analogues e.g. polypeptides comprising the pyrin-domain of IFI16 or fragments for use in methods of treatment. Thus, a method is also provided of treating a disorder associated with STING activity comprising administering an IFI16 pyrin inhibitor and/or a pyrin-domain analogue, as defined herein above, to an individual in need thereof.

However, the IFI16 pyrin inhibitor and/or pyrin-domain analogue as defined elsewhere herein are also provided generally for use in medicine, i.e. for use as a medicament. These compounds can be used for the treatment of any clinical condition, which can be treated, prevented or ameliorated by modulation of STING activity.

In one aspect, a use is provided of an IFI16 pyrin inhibitor and/or a pyrin-domain analogue, as defined herein above, for the preparation of a medicament, for example for the preparation of a medicament for the treatment of a disorder associated with STING activity, either insufficient or excessive STING activity. As mentioned above, the disorder may be any clinical condition, which can be treated, prevented or ameliorated by modulation of STING activity.

The uses and methods provided herein for medical use and/or for treatment of a disorder as specified herein, may also involve a combination therapy, where the "IFI16 pyrin inhibitor" and/or "pyrin-domain analogues" as defined herein above are combined with at least one additional active compound. The at least one additional active compound may be administered before, concomitantly or subsequent to the administration of the IFI16 pyrin inhibitor and/or pyrin-domain analogue.

In one preferred embodiment, the IFI16 pyrin inhibitor and/or pyrin-domain analogue is provided for use in the treatment of cancer, and in this embodiment, administration of an IFI16 pyrin inhibitor and/or pyrin-domain analogue is administered together with an anticancer agent.

This agent is preferably a chemotherapeutic agent. The chemotherapeutic agent is preferably administered by systemic administration, for example by intravenous injection of a solution comprising the chemotherapeutic agent or by oral administration. The chemotherapeutic agent may be selected from alkylating agents, anti-metabolites, anti-microtubule agents, topoisomerase inhibitors and cytotoxic antibiotics.

In one embodiment, the chemotherapeutic agent is an alkylating agent. An alkylating agent is used in cancer treatment as an antineoplastic agent that attaches an alkyl group ($CnH2n+1$) to DNA. The alkyl group is attached to the guanine base of DNA, at the number 7 nitrogen atom of the purine ring. Since cancer cells, in general, proliferate faster and with less error-correction than healthy cells, cancer cells are more sensitive to DNA damage, alkylated DNA. Dialkylating agents can react with two different 7-N-guanine residues, and monoalkylating agents can react only with one 7-N of guanine.

Examples of alkylating agents are Nitrogen mustards, such as Cyclophosphamide, Mechlorethamine or mustine (HN2) (trade name Mustargen), Uramustine or uracil mustard, Melphalan, Chlorambucil, Ifosfamide and Bendamustine.

Other examples are Nitrosoureas, such as Carmustine, Lomustine and Streptozocin. In another embodiment, the alkylating agent is an Alkyl sulfonate, such as Busulfan. In another embodiment, the agent is Thiotepa or an analogue thereof.

The chemotherapeutic agent may also be a Platinum-based chemotherapeutic agent, which acts as an alkylating agent. These agents do not have an alkyl group, but nevertheless damage DNA, by permanently coordinating to DNA to interfere with DNA repair. These agents are sometimes referred to as "alkylating-like". Such agents include Cisplatin, Carboplatin, Nedaplatin, Oxaliplatin, Satraplatin, and Triplatin tetranitrate.

In yet another embodiment, the chemotherapeutic agent is an alkylating agent selected from procarbazine, altretamine, tetrazines, such as dacarbazine, mitozolomide and temozolomide.

In one embodiment, the chemotherapeutic agent is an alkylating agent, a topoisomerase inhibitor, such as Irinotecan, which targets type 1 topoisomerase or Etoposide, which targets type 2 topoisomerase. In another embodiment, the chemotherapeutic agent is a vascular endothelial growth factor (VEGF) inhibitor, such as Bevazizumab.

In another embodiment, the chemotherapeutic agent is selected from Nitrogen mustards, such as Cyclophosphamide, Mechlorethamine or mustine (HN2) (trade name Mustargen), Uramustine or uracil mustard, Melphalan, Chlorambucil, Ifosfamide and Bendamustine. In another embodiment, the chemotherapeutic agent is selected from Nitrosoureas, such as Carmustine, Lomustine and Streptozocin. In another embodiment, the chemotherapeutic agent is selected from Alkyl sulfonates, such as Busulfan. In another embodiment, the chemotherapeutic agent is Thiotepa or an analogue thereof. In another embodiment, the chemotherapeutic agent is selected from Platinum-based chemotherapeutic agents, such as Cisplatin, Carboplatin, Nedaplatin, Oxaliplatin, Satraplatin, and Triplatin tetranitrate. In another embodiment, the chemotherapeutic agent is selected from procarbazine, altretamine or tetrazines, such as dacarbazine, mitozolomide and temozolomide. In another embodiment, the chemotherapeutic agent is selected from topoisomerase inhibitors such as amsacrine, etoposide, etoposide phosphate, teniposide, doxorubicin, irinotecan, topotecan, exatecan, lurtotecan. In yet another embodiment, the chemotherapeutic agent is selected from VEGF inhibitors, such as bevacizumab and ranibizumab.

Notably, the at least one additional active compound provided in the uses and methods for medical use and/or for treatment of a disorder as specified herein together with the "IFI16 pyrin inhibitor" and/or "pyrin-domain analogues" as defined herein above may also be a non-chemotherapeutic agent. In particular, the at least one additional active compound is in one embodiment one or more checkpoint inhibitors. Checkpoint inhibitors are generally drugs that help the body recognize and attack cancer cells Moreover, the uses and methods provided herein for medical use and/or for treatment of a disorder as specified herein, may also involve a combination therapy, where the "IFI16 pyrin inhibitor" and/or "pyrin-domain analogues" as defined herein above may be combined with radiation therapy. Thus, of the "IFI16 pyrin inhibitor" and/or "pyrin-domain analogues" as defined herein are in certain embodiments administered, optionally with the at least one additional active compound before, during and/or after the treated individual is subjected to radiation therapy. Provision of a "IFI16 pyrin inhibitor" and/or a "pyrin-domain analogue" as defined herein in combination with radiation therapy serves to boost the STING-dependent immune response, which is elicited by the radiation therapy and thereby maximizing the effect of the radiation therapy.

In certain embodiments, the IFI16 pyrin inhibitor and/or pyrin-domain analogue is provided for use in the treatment of disorders associated with insufficient or excessive STING activity. These disorders include immuno-deficiency disorders or auto-immune disorders. In these embodiments, the treatment may include one or more additional active compounds selected from immuno-modulating agents, such as TLR agonists, cytokines, chemokines, interleukins, bacterias, vaccines and/or inactivated viruses.

Pharmaceutical Composition

Whilst it is possible for the compounds or polypeptides of the present invention to be administered as the raw chemical, it is preferred to present them in the form of a pharmaceutical composition. Accordingly, the present invention further provides a pharmaceutical composition, which comprises an IFI16 pyrin inhibitor of the present invention or a pharmaceutically acceptable salt thereof, and a pharmaceutically acceptable carrier therefore. The invention also provides pharmaceutical compositions comprising a polypeptide comprising the pyrin-domain of IFI16 or a fragment thereof and a pharmaceutically acceptable carrier therefore.

The pharmaceutical compositions may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients, which may also act as diluents, flavoring agents, solubilizers, lubricants, suspending agents, binders, preservatives, wetting agents, tablet disintegrating agents, or an encapsulating material.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The compounds or polypeptides of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Preferably, the formulation will comprise about 0.5% to 75% by weight of the active ingredient(s) with the remainder consisting of suitable pharmaceutical excipients as described herein.

Pharmaceutically acceptable salts of the IFI16 pyrin inhibitors, where they can be prepared, are also intended to be covered by this invention. These salts will be ones that are acceptable in their application to a pharmaceutical use.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds or polypeptides of the invention are in general administered in an "effective amount" or an amount necessary to achieve an "effective level" in the individual patient. When the "effective level" is used as the preferred endpoint for dosing, the actual dose and schedule can vary, depending on inter-individual differences in pharmacokinetics, drug distribution, and metabolism. The "effective level" can be defined, for example, as the blood or tissue level desired in the patient that corresponds to a concentration of the compounds or polypeptides according to the invention.

The compounds or polypeptides of the invention may be administered together with one or more other active compounds, typically with one or more other active compounds useful for treatment of the particular disorder to be treated. Thus, in embodiments of the invention, wherein the disorder is cancer, the compounds or polypeptides of the invention may be administered together with one or more anti-cancer agents.

Certain embodiments of pharmaceutical compositions of the invention, which preferably are liquid pharmaceutical compositions, may comprise a compound of the invention present in a concentration from about 0.01 mg/ml to about 50 mg/ml, such as from about 1 mg/ml to about 20 mg/ml, e. g. from about 1 mg/ml to about 10 mg/ml. In some embodiments, the composition has a pH from 2.0 to 10.0. A pharmaceutical composition of the invention may further comprise a buffer system, preservative(s), isotonicity agent(s), chelating stabilizer(s) and/or surfactant(s). Particularly useful embodiments of liquid pharmaceutical compositions of the invention are aqueous compositions, i.e. compositions comprising water. Such compositions may be in the form of an aqueous solution or an aqueous suspension. Preferred embodiments of aqueous pharmaceutical compositions of the invention are aqueous solutions. In the context of the invention the term "aqueous composition" will normally refer to a composition comprising at least 50% by weight (50% w/w) of water. Likewise, the term "aqueous solution" will normally refer to a solution comprising at least 50% w/w of water, and the term "aqueous suspension" to a suspension comprising at least 50% w/w of water. In some embodiments, a pharmaceutical composition of the invention comprises an aqueous solution of a compound (or a pharmaceutically acceptable salt or solvate thereof) of the invention present at a concentration of from 0.1 mg/ml or above, together with a buffer, the composition having a pH from about 2.0 to about 10.0, such as a pH from about 6.0 to about 8.5, e.g. from about 6.5 to about 8.5, such as from about 7.0 to about 8.5, or from about 6.5 to about 8.0. In other embodiments of a pharmaceutical composition of the invention, the pH of the composition is a pH selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 155.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.8, 9.9, and 10.0. The pH of the composition may be at least 1 pH unit from (i.e., higher or lower than) the isoelectric point of the constituent compound of the invention, such as at least 2 pH units from (i.e., higher or lower than) the isoelectric point of the peptide compound of the invention. In further embodiments of buffer-containing pharmaceutical compositions of the invention, the buffer or buffer substance is selected from the group consisting of: acetate buffers (e.g. sodium acetate), sodium carbonate, citrates (e.g. sodium citrate), glycylglycine, histidine, glycine, lysine, arginine, phosphates (e.g. chosen among sodium dihydrogen phosphate, disodium hydrogen phosphate and trisodium phosphate), TRIS (i.e., tris(hydroxymethyl)aminomethane), HEPES (i.e., 4-(2-hydroxyethyl)-1-piperazine-ethanesulfonic acid), BICINE (i.e., N,N-bis(2-hydroxyethyl)glycine), and TRICINE (i.e., N-[tris(hydroxymethyl)methyl]glycine), as well as succinate, malate, maleate, fumarate, tartrate, and aspartate buffers, and mixtures thereof.

Preservative

In further embodiments of pharmaceutical compositions of the invention, the composition comprises a pharmaceutically acceptable preservative. Relevant preservatives include preservatives selected from the group consisting of: phenol, o-cresol, m-cresol, p-cresol, methyl p-hydroxybenzoate, ethyl p-hydroxybenzoate, propyl p-hydroxybenzoate, butyl p-5 hydroxybenzoate, 2-phenoxyethanol, 2-phenylethanol, benzyl alcohol, ethanol, chlorobutanol, thiomerosal, bronopol, benzoic acid, imidurea, chlorhexidine, sodium dehydroacetate, chlorocresol, benzethonium chloride, chlorphenesine [i.e. 3-(p-chlorphenoxy)propane-1,2-diol] and mixtures thereof. The preservative may be present in a concentration of from 0.1 mg/ml to 30 mg/ml, such as from 0.1 mg/ml to 20 mg/ml (e.g. from 0.1 mg/ml to 5 mg/ml, or from 5 mg/ml to 10 mg/ml, or from 10 mg/ml to 20 mg/ml) in the final liquid composition. The use of a preservative in pharmaceutical compositions is well known to the skilled worker. In this connection, reference may be made to Remington: The Science and Practice of Pharmacy, 19th edition, 1995.

Isotonicity Agent

In further embodiments, a pharmaceutical composition of the invention comprises an isotonicity agent (i. e., a pharmaceutically acceptable agent which is included in the composition for the purpose of rendering the composition isotonic). In some embodiments, the composition is administered to a subject by injection. Relevant isotonicity agents include agents selected from the group consisting of: salts (e.g., sodium chloride), sugars and sugar alcohols, amino acids (including glycine, arginine, lysine, isoleucine, aspartic acid, tryptophan and threonine), alditols (including glycerol, propyleneglycol (i.e. 1,2-propanediol), 1,3-propanediol and 1,3-butanediol), polyethylene glycols (including PEG400) and mixtures thereof. Suitable sugars include mono-, di- and polysaccharides, and water-soluble glucans, such as fructose, glucose, mannose, sorbose, xylose, maltose, lactose, sucrose, trehalose, dextran, pullulan, dextrin, cyclodextrin, soluble starch, hydroxyethyl starch and carboxymethylcellulose sodium salt. In some embodiments sucrose may be employed. Suitable sugar alcohols include hydroxylated C4-C8 hydrocarbons, including mannitol, sorbitol, inositol, galacititol, dulcitol, xylitol and arabitol. In some embodiments mannitol may be employed. The sugars or sugar alcohols mentioned above may be used individually or in combination. There is no fixed limit to the amount of isotonicity agent used, as long as it is soluble in the liquid formulation, establishes isotonicity and does not adversely affect the stability of the composition. The concentration of isotonicity agent (e.g. sugar or sugar alcohol) in the final liquid composition may be, e.g., from about 1 mg/ml to about 150 mg/ml, such as from 1 mg/ml to 50 mg/ml. In particular embodiments, the concentration may be from 1 mg/ml to 7 mg/ml, or from 8 mg/ml to 24 mg/ml, or from 25 mg/ml to 50 mg/ml. The use of an isotonicity agent in pharmaceutical compositions is well known to the skilled person. In this connection, reference may be made to Remington: The Science and Practice of Pharmacy, 19th edition, 1995. In further embodiments of pharmaceutical compositions of the invention, the composition comprises a chelating agent. Relevant chelating agents include salts of ethylenediaminetetraacetic acid (EDTA), citric acid or aspartic acid, and mixtures thereof. The chelating agent may suitably be present in the final liquid composition in a concentration of from 0.1 mg/ml to 5 mg/ml, such as from 0.1 mg/ml to 2 mg/ml, or from 2 mg/ml to 5 mg/ml. The use of a chelating agent in pharmaceutical compositions is well-known to the skilled worker. In this connection, reference may be made to Remington: The Science and Practice of Pharmacy, 19th edition, 1995.

Stabilizer

In further embodiments of pharmaceutical compositions of the invention, the composition comprises a stabilizer. The use of a stabilizer in pharmaceutical compositions is well-known to the skilled worker, and in this connection reference may be made to Remington: The Science and Practice of Pharmacy, 19th edition, 1995. Particularly useful pharmaceutical compositions of the invention are stabilized liquid compositions with therapeutically active components that include a compound of the invention (e.g., a peptide of the invention) that may otherwise possibly exhibit aggregate formation during storage in a liquid medium. In this context, "aggregate formation" refers to physical interactions between the peptide molecules that result in formation of larger assemblies that undergo some degree of visible precipitation from the solution. As used herein, "during storage in a liquid medium" refers to the storage of a liquid composition that, once prepared, is not necessarily immediately administered to a subject. Instead, following preparation, it may be packaged for storage, either in a liquid form, in a frozen state, or in a dried form for later reconstitution into a liquid form or other form suitable for administration to a subject. As used herein, "dried form" refers to an initially liquid pharmaceutical composition or formulation that has been dried by freeze-drying (i.e., lyophilization), by spray-drying or by air-drying. Aggregate formation by a peptide during storage of a liquid pharmaceutical composition thereof can adversely affect biological activity of the peptide in question, resulting in a loss of therapeutic efficacy of the pharmaceutical composition. Furthermore, aggregate formation may cause other problems, such as blockage of tubing, membranes, or pumps if such a peptide-containing pharmaceutical composition is administered using an infusion system. Thus, peptides of the invention may be beneficial in overcoming these problems. Examples of stabilizers appropriate for incorporation in pharmaceutical compositions of the invention include, but are not limited to, the following: amino acids in their free base form or salt form, e. g. amino acids carrying a charged side chain, such as arginine, lysine, aspartic acid or glutamic acid, or amino acids such as glycine or methionine (in that incorporation of methionine may additionally inhibit oxidation of methionine residues in peptides comprising at least one methionine residue susceptible to such oxidation); certain polymers (e. g., polyethylene glycols (such as PEG 3350), polyvinylalcohol (PVA), polyvinylpyrrolidone (PVP), and carboxy-/hydroxycellulose and derivatives thereof); cyclodextrins; sulfur-containing substances (such as monothioglycerol, thioglycolic acid and 2-methylthioethanol); and surfactants (such as non-ionic surfactants, including non-ionic surfactants of the Poloxamer or Polysorbate (Tween) types. The use of a surfactant in pharmaceutical compositions is well known to the skilled worker. In this connection, reference may be made to Remington: The Science and Practice of Pharmacy, 19th edition, 1995.

Other Types of Constituents

Additional types of constituents may also be present in pharmaceutical compositions of the present invention. Non-limiting examples of classes of such constituents include wetting agents, emulsifiers, antioxidants, bulking agents, oleaginous vehicles and proteins (e. g., human serum albumin or gelatin).

Virus-Like Particles (VLPs) Comprising cGAMP

One aspect of the present invention relates to a method of producing virus-like particles comprising cGAMP, wherein the virus-like particles are produced in cells that overexpress IFI16 protein.

In particular, the method comprises preparing a virus-like particle comprising cyclic GMP-AMP packaged into said virus-like particle, wherein the method comprises:
 a) co-expression of a Cyclic GMP synthase (cGAS) and a viral fusogenic glycoprotein in an eukaryotic cell, which overexpress IFI16 under conditions allowing the synthesis of cGAMP and the viral fusogenic glycoprotein in said cell; and
 b) recovering of the virus-like particles produced by said cell, wherein the virus-like particle comprises cGAMP packaged into said virus-like particle.

The inventors have surprisingly found that a VLP containing cGAMP, can be very efficiently prepared when cGAS is co-expressed with IFI16 in a cell, which also express the components of VLPs.

The eukaryotic producer cell may further express a capsid from retroviridae, and the viral fusogenic glycoprotein is in a preferred embodiment a glycoprotein from retroviridae (including lentivirus and retrovirus), herpesviridae, poxviridae, hepadnaviridae, flaviviridae, togavoridae, coronaviridae, hepatitis D virus, orthomyxoviridae, paramyxoviridae, rhabdoviridae, bunyaviridae, filoviridae, and orthopoxiviridae (e.g. variola), preferably from orthomyxovirus, retroviruses, and rhabdovirus. The viral fusogenic glycoprotein can be a glycoprotein from HIV (Human Immunodeficiency Virus) including HIV-1 and HIV-2, Influenza including Influenza A (e.g. subtypes H5N1 and H1N1) and Influenza B, and, thogotovirus, and VSV (Vesicular Stomatitis Virus). The retroviral capsid is preferably from retroviridae, preferably lentivirus and retrovirus, preferably from HIV or MLV (Murine Leukemia Virus).

Cyclic GMP-AMP synthase belonging to EC 2.7.7.86 and is part of the nucleotidyl transferase superfamily. cGAS have also been well characterized in Bovine, pig and Vibrio cholera serotype 01 (respectively, see UniprotKB ID Nos E1BGN7, 13LM39 and Q9KVG7) and can be also found in *Drosophila* (e.g., *D. melanogaster*), zebrafish (*D. rerio*), *A. carolinensis, A. melanoleuca, A. mellifera, B. floridae, C. lupus familiaris, E. caballus, F. catus, G. gallus, G. gorilla gorilla, H magnipapillata, I. scapularis, M. brevicollis, M. domestica, M. gallopavo, M. mulatta, N. vectensis, N. vitrioennis, O. anatinus, O. aries, O. cuniculus, O. latipes, P. abelii, P. anubis, P. paniscus, P. troglodytes, R. norvegicus, S. harrisii, T. castaneum, T. guttata* and *X. tropicalis* or *laevis* (Wu et al, 2014, Nucleic Acids Research, 42, 8243-8257; the disclosure of which is incorporated by reference). In a preferred embodiment, nucleic acid sequence encoding either the human or murine cGAS is used; cf. SEQ ID NO: 29 and 30, respectively.

The present invention also pertains to virus-like particles obtainable by the above method, where the virus-like particles comprising cGAMP packaged into said virus-like particle.

The virus-like particles obtained according to the method provided herein by overexpression of IFI16 in the producer cells, can be used in therapy according to the invention. For example, these virus-like particles are provided for use in medicine and/or therapy. In particular, the virus-like particles are provided for use in treatment of an auto-immune or inflammatory disorder or an infectious disease or any disorder associated with STING activity. The virus-like particles may thus be used as a vaccine adjuvant.

Thus, the invention also relates to a method of treating an auto-immune or inflammatory disorder or an infectious disease or any disorder associated with STING activity comprising administering the viral particles produced according to the above method.

The virus-like particles are also provided for use in the preparation of a medicament, such as an adjuvant and/or a medicament for treatment of an auto-immune or inflammatory disorder or an infectious disease or any disorder associated with STING activity.

The virus-like particles comprise a lipoprotein envelope including a viral fusogenic glycoprotein, and the virus-like particle contains cyclic guanosine monophosphate-adenosine monophosphate (cGAMP) packaged into the virus-like particle.

The viral fusogenic glycoprotein can be a glycoprotein from retroviridae (including lentivirus and retrovirus), herpesviridae, poxviridae, hepadnaviridae, flaviviridae, togavoridae, coronaviridae, hepatitis D virus, orthomyxoviridae, paramyxoviridae, filoviridae, rhabdoviridae, Bunyaviridae, or orthopoxivridae (e.g. variola), preferably from orthomyxovirus, retroviruses, rhabdovirus.

The viral fusogenic glycoprotein may be a glycoprotein from HIV (Human Immunodeficiency Virus) including HIV-1 and HIV-2, Influenza including Influenza A (e.g. subtypes H5N1 and H1N1) and Influenza B, thogotovirus, or VSV (Vesicular Stomatitis Virus).

In a preferred embodiment, the virus-like particle comprises a capsid from retroviridae, such as from retroviridae, preferably lentivirus and retrovirus. The retroviral capsid is in a preferred embodiment from HIV or MLV (Murine Leukemia Virus).

The cyclic guanosine monophosphate-adenosine monophosphate is preferably cGAMP (2'-3'-cyclic GMP-AMP) or (3'-3'-cyclic GMP-AMP).

The virus-like may further comprise an antigen or any other protein or nucleic acid of interest.

The invention also relates to a pharmaceutical composition, vaccine or veterinary composition comprising the virus-like particle and a pharmaceutically acceptable carrier. The pharmaceutical, vaccine or veterinary composition may further comprise an antigen or a therapeutic active agent.

A non-exhaustive list of antigens which can be further included in VLPs, in addition to the viral glycoprotein and capsid proteins, includes any viral protein from Hepatitis C virus (HCV) such as core protein, p7 protein, NS3 and/or NS4A polypeptides, human immunodeficiency virus (HIV) including HIV-1 and HIV-2 such as gag, nef, Tat, Pol, Rev or reverse transcriptase, simian immunodeficiency virus (SIV), feline immunodeficiency virus (FIV), Puma lentivirus, bovine immunodeficiency virus (BIV), Jembrana disease virus, Equine infections anemia virus, Visna/maedi virus, Caprine arthritis encephalitis virus, feline leukemia virus (FeLV), murine leukemia virus (MLV), bovine leukemia virus (BLV), human T-lymphotropic virus (HTLV, e.g., HTLV-1, -2, -3 or -4), Rous sarcoma virus (RSV), Avian sarcoma leucosis virus, Newcastle disease virus (ND), Dengue virus, Hantaan virus, Influenza viruses A or B such as matrix proteins M1 and M2, Hepatitis B virus (HBV), Vesicular Stomatitis Virus (VSV), thogotovirus, hepatitis A virus (HAV), Ebola virus or Marburg virus such as matric VP40, Murray Valley encephalitis virus, Japanese encephalitis virus and West Nile virus. In a very specific aspect, the viral fusogenic glycoprotein is a glycoprotein from HIV (Human Immunodeficiency Virus) including HIV-1 and HIV-2, thogotovirus, Chikungunya virus such as C protein, human papilloma virus (HPV) such as L1 proteins or antigenic fragment thereof, human severe acute respiratory syndrome coronavirus (SARS CoV), and VSV (Vesicular Stomatitis Virus). More specifically, VLPs can also include antigens from tumor associated antigens such as Her2/neu, CEA (carcinoembryogenic antigen), HER2/neu, MAGE2 and MAGE3 (Melanoma-associated antigen), RAS, mesothelin or p53, from HIV such as Vpr, Vpx, Vpu, Vif and Env, from bacteria such as C. albicans SAP2 (secreted aspartyl proteinase 2), Clostridium difficile, from parasites such as P. falciform proteins such as CSP (circumsporozoite protein), AMA-1 (apical membrane antigen-1), TRAP/SSP2 (sporozoite surface protein 2, LSA (liver stage antigen), Pf Exp1 (Pf exported protein 1), SALSA (Pf antigen 2 sporozoite and liver stage antigen), STARP (sporozoite threonine and aspargins-rich protein) or any protein as disclosed in WO2011/138251.

The invention also in one aspect relates to a method for inducing or enhancing an immune response in a subject comprising administrating the virus-like particle or according to claim 1 or a pharmaceutical composition above. A method for preventing or treating an infectious disease or a cancer in a subject comprising administrating the virus-like particles is also provided.

In one aspect, a recombinant eukaryotic host cell is provided comprising a sequence encoding a cGAS (Cyclic GMP-AMP synthase) and a sequence encoding a viral fusogenic glycoprotein and a sequence encoding Interferon-gamma-inducible protein 16 (IFI16) or part thereof. The sequence encoding IFI16 should preferably ensure overexpression of IFI16. Thus, the IFI16 sequence is in one embodiment not the endogenous sequence. The host cell may also comprise a sequence encoding a retroviral capsid protein.

Cyclic GMP synthase (cGAS) and a viral fusogenic glycoprotein in an eukaryotic cell, which Overexpression of IFI16 can be achieved by stable or transient expression or a combination thereof. In a preferred embodiment, however, IFI16 is stably overexpressed.

The recombinant eukaryotic host may further comprise a sequence encoding an antigen or any other protein or nucleic acid of interest.

Moreover, the recombinant eukaryotic host cell is provided as a medicinal drug or a vaccine adjuvant. The invention therefore also provides a method for inducing or enhancing an immune response or for preventing or treating an infectious disease or a cancer in a subject comprising administrating the recombinant eukaryotic host cell.

Sequences

The following sequences are cited in the present disclosure. It is noted that the biotin-moiety conjugated to polypeptides of SEQ ID Nos: 15-24, 26 and 28, recited herein below, are attached via a six carbon linear aminohexanoic (Ahx) linker.

```
pyrin-domain of human IFI16
                                                    SEQ ID NO: 1
KKYKNIVLLKGLEVINDYHFRMVKSLLSNDLKLNLKMREEYDKIQIADLMEEKFRGDAG
LGKLIKIFEDIPTLEDLAETLKKEKLK gamma-interferon-inducible protein 16 isoform X1 [Homosapiens]
                                                    SEQ ID NO: 2
MSVKMGKKYKNIVLLKGLEVINDYHFRMVKSLLSNDLKLNLKMREEYDKI

QIADLMEEKFRGDAGLGKLIKIFEDIPTLEDLAETLKKEKLKVKGPALSR

KRKKEVDATSPAPSTSSTVKTEGAEATPGAQKRKKSTKEKAGPKGSKVSE

EQTQPPSPAGAGMSTAMGRSPSPKTSLSAPPNSSSTENPKTVAKCQVTPR

RNVLQKRPVIVKVLSTTKPFEYETPEMEKKIMFHATVATQTQFFHVKVLN

TSLKEKFNGKKIIIISDYLEYDSLLEVNEESTVSEAGPNQTFEVPNKIIN

RAKETLKIDILHKQASGNIVYGVFMLHKKTVNQKTTIYEIQDDRGKMDVV
```

-continued

```
GTGQCHNIPCEEGDKLQLFCFRLRKKNQMSKLISEMHSFIQIKKKTNPRN

NDPKSMKLPQEQRQLPYPSEASTTFPESHLRTPQMPPTTPSSSFFTKKSE

DTISKMNDFMRMQILKEGSHFPGPFMTSIGPAESHPHTPQMPPSTPSSSF

LTTKSEDTISKMNDFMRMQILKEGSHFPGPFMTSIGPAESHPHTPQMPPS

TPSSSFLTTLKPRLKTEPEEVSIEDSAQSDLKEVMVLNATESFVYEPKEQ

KKMFHATVATENEVFRVKVFNIDLKEKFTPKKIIAIANYVCRNGFLEVYP

FTLVADVNADRNMEIPKGLIRSASVTPKINQLCSQTKGSFVNGVFEVHKK

NVRGEFTYYEIQDNTGKMEVVVHGRLTTINCEEGDKLKLTCFELAPKSGN

TGELRSVIHSHIKVIKTRKNKKDILNPDSSMETSPDFFF
```

TBK1 serine/threonine-protein kinase TBK1 [Homo sapiens]
SEQ ID NO: 3

```
MQSTSNHLWLLSDILGQGATANVFRGRHKKTGDLFAIKVFNNISFLRPVDVQMREFEV

LKKLNHKNIVKLFAIEEETTTRHKVLIMEFCPCGSLYTVLEEPSNAYGLPESEFLIVLRD

VVGGMNHLRENGIVHRDIKPGNIMRVIGEDGQSVYKLTDFGAARELEDDEQFVSLYG

TEEYLHPDMYERAVLRKDHQKKYGATVDLWSIGVTFYHAATGSLPFRPFEGPRRNKE

VMYKIITGKPSGAISGVQKAENGPIDWSGDMPVSCSLSRGLQVLLTPVLANILEADQEK

CWGFDQFFAETSDILHRMVIHVFSLQQMTAHKIYIHSYNTATIFHELVYKQTKIISSNQE

LIYEGRRLVLEPGRLAQHFPKTTEENPIFVVSREPLNTIGLIYEKISLPKVHPRYDLDGD

ASMAKAITGVVCYACRIASTLLLYQELMRKGIRWLIELIKDDYNETVHKKTEVVITLDFCI

RNIEKTVKVYEKLMKINLEAAELGEISDIHTKLLRLSSSQGTIETSLQDIDSRLSPGGSLA

DAWAHQEGTHPKDRNVEKLQVLLNCMTEIYYQFKKDKAERRLAYNEEQIHKFDKQKL

YYHATKAMTHFTDECVKKYEAFLNKSEEWIRKMLHLRKQLLSLTNQCFDIEEEVSKYQ

EYTNELQETLPQKMFTASSGIKHTMTPIYPSSNTLVEMTLGMKKLKEEMEGVVKELAE

NNHILERFGSLTMDGGLRNVDCL
```

STING_TMEM173 stimulator of interferon genes protein isoform 1 [Homo sapiens]
SEQ ID NO: 4

```
MPHSSLHPSIPCPRGHGAQKAALVLLSACLVTLWGLGEPPEHTLRYLVLHLASLQLGL

LLNGVCSLAEELRHIHSRYRGSYWRTVRACLGCPLRRGALLLLSIYFYYSLPNAVGPP

FTWMLALLGLSQALNILLGLKGLAPAEISAVCEKGNFNVAHGLAWSYYIGYLRLILPEL

QARIRTYNQHYNNLLRGAVSQRLYILLPLDCGVPDNLSMADPNIRFLDKLPQQTGDHA

GIKDRVYSNSIYELLENGQRAGTCVLEYATPLQTLFAMSQYSQAGFSREDRLEQAKLF

CRTLEDILADAPESQNNCRLIAYQEPADDSSFSLSQEVLRHLRQEEKEEVTVGSLKTS

AVPSTSTMSQEPELLISGMEKPLPLRTDFS
```

SEQ ID NO: 5:
KKYKNIVLLKGLEVINDYHFGRKKRRQRRRPQ-NH2

SEQ ID NO: 6:
LEVINDYHFRMVKSLLSNDLGRKKRRQRRRPQ-NH2

SEQ ID NO: 7:
LLSNDLKLNLKMREEYDKIQGRKKRRQRRRPQ-NH2

SEQ ID NO: 8:
EEYDKIQIADLMEEKFRGDGRKKRRQRRRPQ-NH2

SEQ ID NO: 9:
DLMEEKFRGDAGLGKLIKIFGRKKRRQRRRPQ-NH2

SEQ ID NO: 10:
AGLGKLIKIFEDIPTLEDLAGRKKRRQRRRPQ-NH2

-continued

SEQ ID NO: 11:
EDIPTLEDLAETLKKEKLKGRKKRRQRRRPQ-NH2

SEQ ID NO: 12:
NDLKLNLKMREEYDKIQIADLMEEKFRGDAGLGKLIKIFEDIPTLEDLAETLKKEKLKGR
KKRRQRRRPQ-NH2

SEQ ID NO: 13:
KKYKNIVLLKGLEVINDYHFRMVKSLLSNDLKLNLKMREEYDKIQIADLMEEKFGRKKR
RQRRRPQ-NH2

SEQ ID NO: 14:
HFRMVKSLLSNDLKLNLKMREEYDKIQIADLMEEKFRGDAGLGKLIKIFEGRKKRRQR
RRPQ-NH2

SEQ ID NO: 15:
S1: Biotin-KKYKNIVLLKGLEVINDYHFGRKKRRQRRRPQ-NH2

SEQ ID NO: 16:
S2: Biotin-LEVINDYHFRMVKSLLSNDLGRKKRRQRRRPQ-NH2

SEQ ID NO: 17:
S3: Biotin-LLSNDLKLNLKMREEYDKIQGRKKRRQRRRPQ-NH2

SEQ ID NO: 18:
S4: Biotin-EEYDKIQIADLMEEKFRGDGRKKRRQRRRPQ-NH2

SEQ ID NO: 19:
S5: Biotin-DLMEEKFRGDAGLGKLIKIFGRKKRRQRRRPQ-NH2

SEQ ID NO: 20:
S6: Biotin-AGLGKLIKIFEDIPTLEDLAGRKKRRQRRRPQ-NH2

SEQ ID NO: 21:
S7: Biotin-EDIPTLEDLAETLKKEKLKGRKKRRQRRRPQ-NH2

SEQ ID NO: 22:
L1: Biotin-
NDLKLNLKMREEYDKIQIADLMEEKFRGDAGLGKLIKIFEDIPTLEDLAETLKKEKLKGR
KKRRQRRRPQ-NH2

SEQ ID NO: 23:
L2: Biotin-
KKYKNIVLLKGLEVINDYHFRMVKSLLSNDLKLNLKMREEYDKIQIADLMEEKFGRKKR
RQRRRPQ-NH2

SEQ ID NO: 24:
L3: Biotin-
HFRMVKSLLSNDLKLNLKMREEYDKIQIADLMEEKFRGDAGLGKLIKIFEGRKKRRQR
RRPQ-NH2

SEQ ID NO: 25:
S1 (-B): KKYKNIVLLKGLEVINDYHFGRKKRRQRRRPQ-NH2

SEQ ID NO: 26:
S1 (-T)= S1 (-CPP)::
Biotin-KKYKNIVLLKGLEVINDYHF-NH2

SEQ ID NO: 27:
S7 (-B): EDIPTLEDLAETLKKEKLKGRKKRRQRRRPQ-NH2

SEQ ID NO: 28:
S7 (-T) = S7 (-CPP):
Biotin-EDIPTLEDLAETLKKEKLK-NH2

SEQ ID NO: 29: human cGAS
MQPWHGKAMQRASEAGATAPKASARNARGAPMDPTESPAAPEAALPKAGKFGPAR

KSGSRQKKSAPDTQERPPVRATGARAKKAPQRAQDTQPSDATSAPGAEGLEPPAAR

EPALSRAGSCRQRGARCSTKPRPPPGPWDVPSPGLPVSAPILVRRDAAPGASKLRA

VLEKLKLSRDDISTAAGMVKGVVDHLLLRLKCDSAFRGVGLLNTGSYYEHVKISAPNE

FDVMFKLEVPRIQLEEYSNTRAYYFVKFKRNPKENPLSQFLEGEILSASKMLSKFRKIIK

EEINDIKDTDVIMKRKRGGSPAVTLLISEKISVDITLALESKSSWPASTQEGLRIQNWLS

AKVRKQLRLKPFYLVPKHAKEGNGFQEETVVRLSFSHIEKEILNNHGKSKTCCENKEEK

-continued

CCRKDCLKLMKYLLEQLKERFKDKKHLDKFSSYHVKTAFFHVCTQNPQDSQWDRKD

LGLCFDNCVTYFLQCLRTEKLENYFIPEFNLFSSNLIDKRSKEFLTKQIEYERNNEFPVF

DEF

SEQ ID NO: 30: murine cGAS
MEDPRRRTTAPRAKKPSAKRAPTQPSRTRAHAESCGPQRGARSRRAERDG

DTTEKPRAPGPRVHPARATELTKDAQPSAMDAAGATARPAVRVPQQQAIL

DPELPAVREPQPPADPEARKVVRGPSHRRGARSTGQPRAPRGSRKEPDKL

KKVLDKLRLKRKDISEAAETVNKVVERLLRRMQKRESEFKGVEQLNTGSY

YEHVKISAPNEFDVMFKLEVPRIELQEYYETGAFYLVKFKRIPRGNPLSH

FLEGEVLSATKMLSKFRKIIKEEVKEIKDIDVSVEKEKPGSPAVTLLIRN

PEEISVDIILALESKGSWPISTKEGLPIQGWLGTKVRTNLRREPFYLVPK

NAKDGNSFQGETWRLSFSHTEKYILNNHGIEKTCCESSGAKCCRKECLKL

MKYLLEQLKKEFQELDAFCSYHVKTAIFHMWTQDPQDSQWDPRNLSSCFD

KLLAFFLECLRTEKLDHYFIPKFNLFSQELIDRKSKEFLSKKIEYERNNG FPIFDKL.

EXAMPLES

Example 1

The Examples shows two novel functions of human IFI16 in the cGAS-STING pathway. Using human PMA-treated THP1 cells or human monocyte-derived macrophages (MDMs) depleted of IFI16, it was found that early IFN expression in the response to viral infections or DNA transfection requires IFI16. Importantly, in IFI16-deficient cells stimulated with DNA, the level of STING dimerization, phosphorylation and downstream signalling is compromised. Moreover, IFI16 is necessary for efficient cGAMP production through cGAS in response to DNA. Finally, IFI16 actively recruits TBK1 to the cGAMP-stimulated STING complex and thus promotes phosphorylation of STING. Collectively, this suggests that IFI16 serves to regulate STING activation and is an integrated part of the DNA sensing pathway in human macrophages.

Results

Macrophages Lacking IFI16 Showed Impaired Innate Immune Responses to Viral Infections.

Figure 1A:
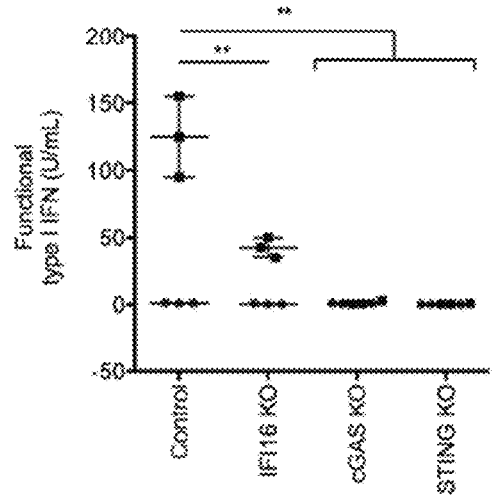
FIGS. 1A-1C: The innate immune response to HSV infection in primary human macrophages and macrophage cell lines is regulated by IFI16.
Figure 1B:
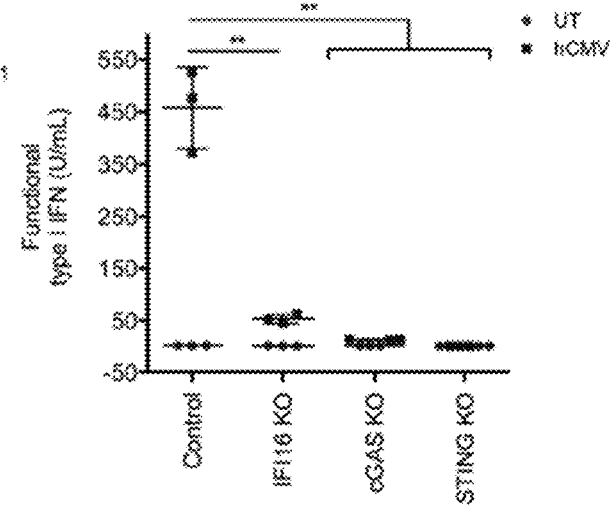
Figure 1C:
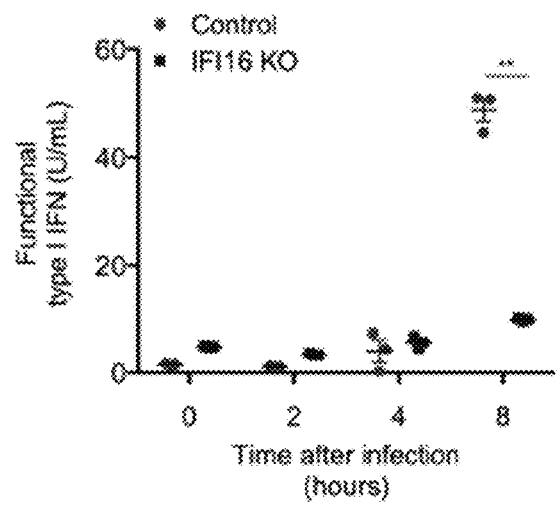

The CRISPR-Cas9 technology was used to generate knockout gene variants in human THP-1 cells, a monocytic cell line that adopts a macrophage-like phenotype upon PMA differentiation. Single cell clones carrying IFI16 mutations were generated based on three different guide RNAs (FIG. 9a). Verification of genetic KO was carried out by Western blot on PMA-treated THP1 cells (FIGS. 8b and c) and by single clone sequencing (FIG. 16d). The THP-1 clones harbouring KO mutations in genes encoding STING and cGAS have been described in Holm et al., 2016. Members of the herpesviridae trigger robust innate immune responses in macrophages. It was determined whether the KO cell lines exhibit a dependence on IFI16 for herpes virus-induced type I IFN production. In control PMA-treated THP1 cells, elevated type I IFN secretion was observed 18 hrs after infection with both herpes simplex virus 1 (HSV-1; FIG. 1a) and human cytomegalovirus (hCMV; FIG. 1b). This response was completely abolished in THP1 cells lacking cGAS and STING, and only minor residual induction of type I IFNs in IFI16 KO cells was observed (FIGS. 1a and 1b). Using a higher MOI of HSV1, we were able to explore IFN secretion at earlier time points (2-8 hrs). The results showed that IFI16 is required for potent early immune activation following HSV-1 infection (FIG. 1c).

To exclude potential off-target effects of the IFI16-directed CRISPR knockout, innate immune responses to the paramyxovirus Newcastle disease virus (NDV) were evaluated, an RNA virus known to trigger RIG-I activation. In this case, type I IFN and TNF-α responses were not affected by knocking out IFI16 (FIGS. 10a and 10b). Additionally, to exclude saturating effects of high NDV titres, we confirmed our results using sequential dilutions of viral inoculums (FIG. 10c). Thus, IFI16 specifically enhanced the capacity of macrophages to sense infection by DNA-containing or -producing viruses.

Figure 2A:
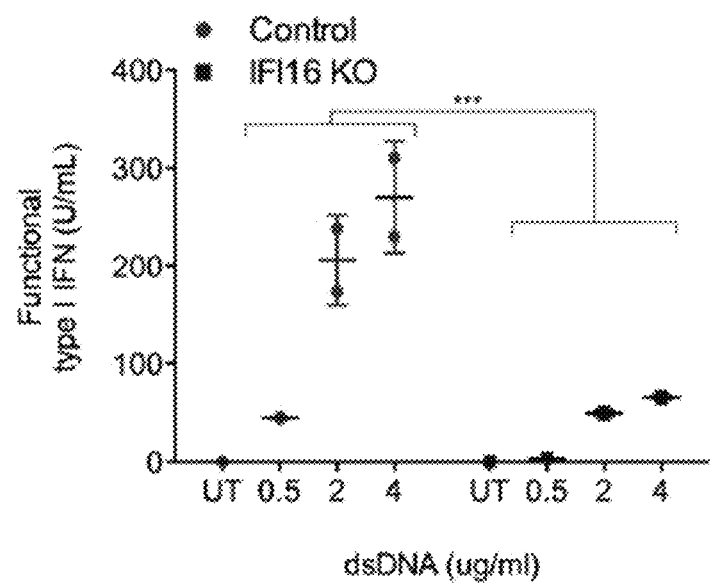
FIGS. 2A-2E: Cytosolic DNA sensing and efficient innate signaling is dependent on IFI16.
Figure 11B:
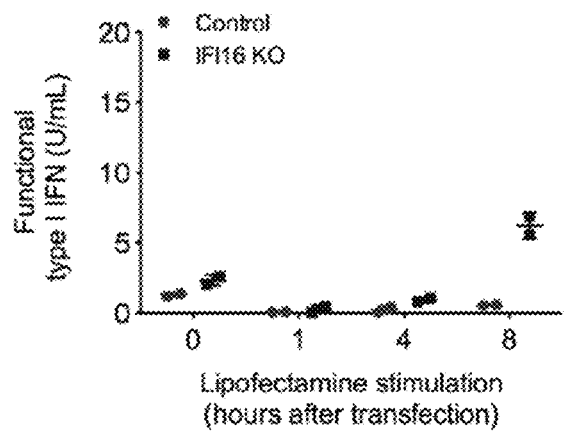

IFI16 regulates early and robust activation of the STING signalling cascade A reliable approach to trigger immune activation by cGAS and STING is liposomal transfection of synthetic DNA of various structures. Control and IFI16 KO cells were transfected with different types and concentrations of synthetic DNA and early type I IFN secretion was evaluated. Both HSV-1 60mer (dsDNA) and herring testis DNA (HT-DNA) induced robust IFN responses in control THP1 cells. In comparison, THP1 cells lacking IFI16 showed a significantly weaker IFN response (FIG. 2a and FIG. 11a).) As a control, lipofectamine transfection alone did not induce substantial amount of type I IFN (FIG. 11b).

Figure 2B:
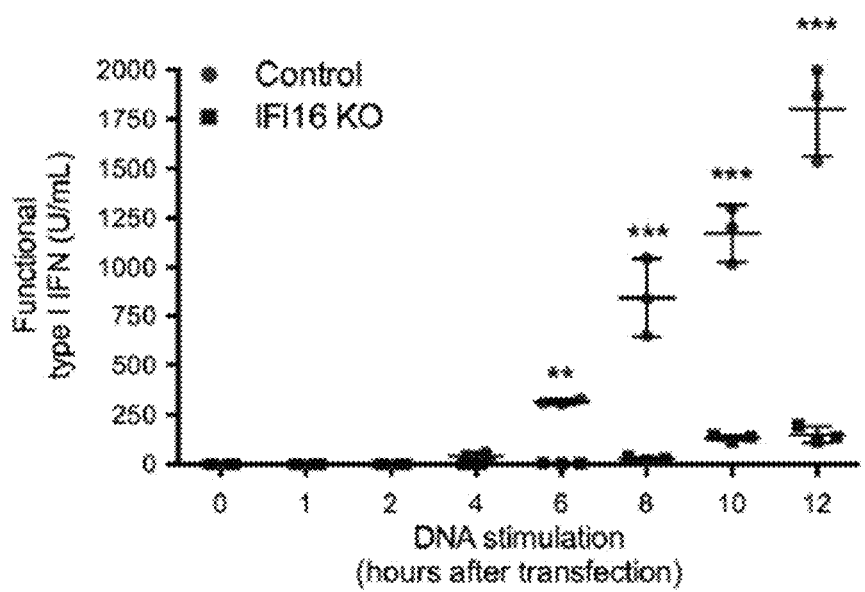
Figure 2C:
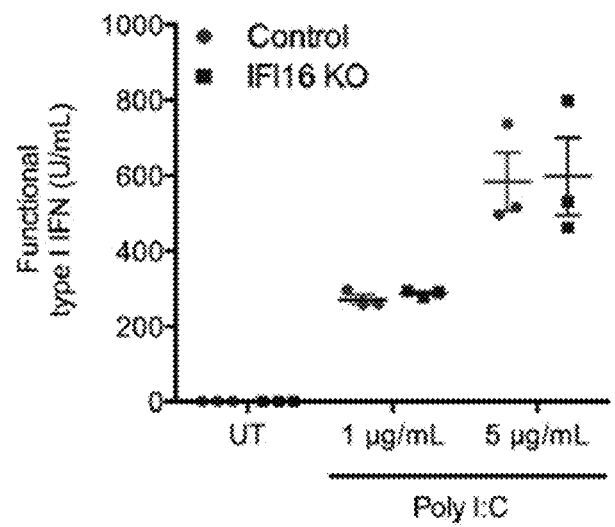
Figure 11C:
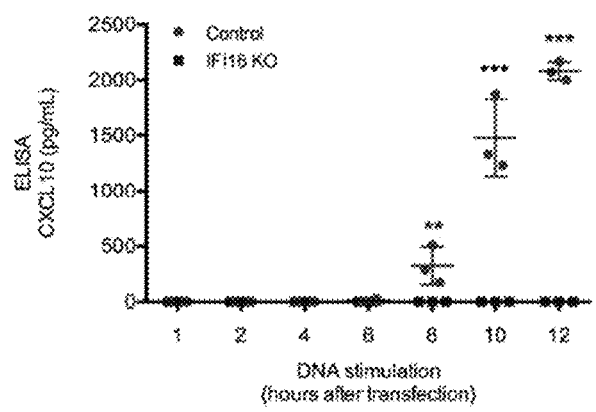
Figure 11D:
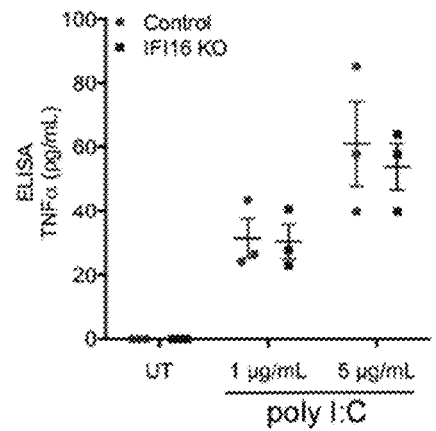

Control and IFI16 KO THP1 cells were transfected with dsDNA and type I IFN secretion determined over a 12 hrs time course. In control cells, a continuing increase of IFN responses was observed, whereas IFI16 KO cells depictured a significantly attenuated and delayed IFN response (FIG. 2b). This impairment in THP1 cells lacking IFI16 was even more pronounced when expression of the IRF3-dependent target gene CXCL10 was evaluated, which was completely absent in IFI16 KO cells (FIG. 11c). In contrast, transfection with polyI:C that activates the RIG-I pathway, induced normal IFN (FIG. 2c) and TNF-α responses (FIG. 11d) in control and IFI16 KO cells. The minimal IFN response observed in IFI16 KO THP1 cells could be due to effects on other innate signalling pathways. However, when control and IFI16 KO cells were pre-treated with the TBK1/IKKε kinase inhibitor BX-795 prior to DNA transfection a complete block of type I IFN responses was observed (FIG. 11e). To confirm that DNA transfection did not affect kinases other than TBK1 in the IFN induction pathway, IFN responses in TBK1 KO THP1 cells were determined (FIG. 11f). TBK1 KO cells did not produce type I IFN upon transfection with dsDNA, whereas control THP1 cells demonstrated robust induction of IFN (FIG. 11g). IFI16 was knocked-down in monocyte-derived-macrophages using siRNA (FIG. 12a) and transfected with dsDNA 48 hours after the final siRNA treatment. Efficient IFI16 depletion was associated with significantly reduced IFN responses following transfection with dsDNA but not polyI:C (FIGS. 12b and c).

These observations were further confirmed in additional THP1 IFI16 KO clones from a total of three different gRNA sequences (FIG. 8b). All clones responded normally to polyI:C transfection or NDV infection but showed strongly impaired type I IFN responses to dsDNA (FIG. 13a-e). Type I IFN responses were also absent upon dsDNA treatment in THP1 cells lacking cGAS or STING (FIG. 13f). Finally, two clones were selected and IFI16 expression was reconstituted by lentiviral gene delivery. These cells demonstrated robust IFI16 expression 48 hrs after transduction (FIG. 13g) and gained the capacity to respond to dsDNA transfection with phosphorylation of IRF3 (FIG. 13g) and production of type I IFN (FIG. 13h).

Figure 2D:
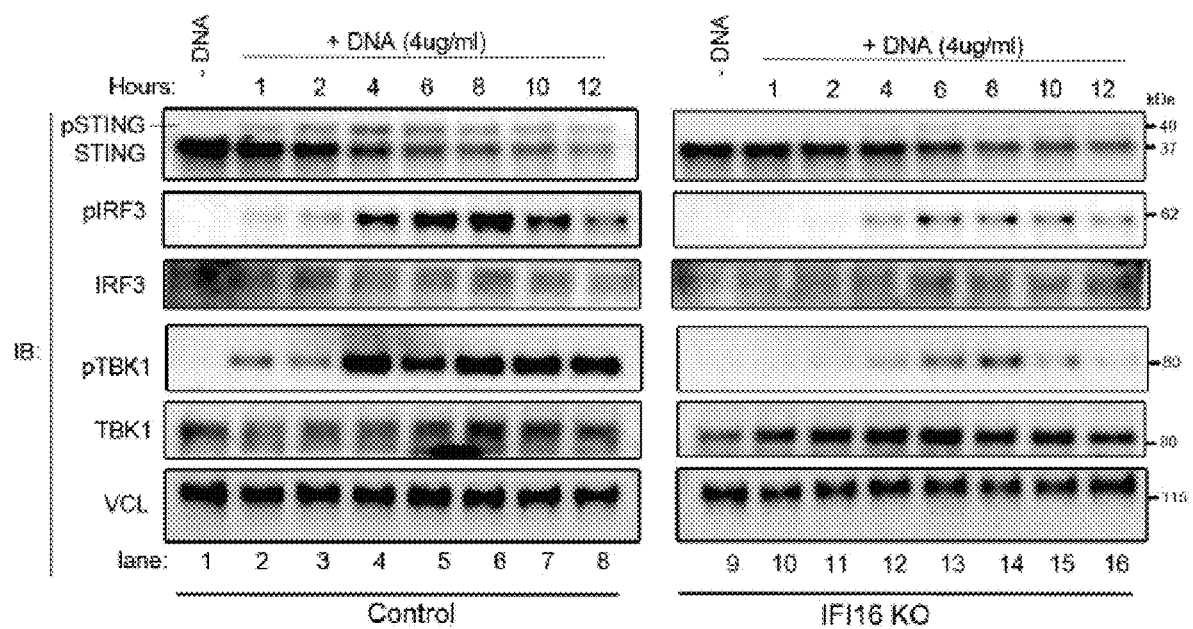
Figure 14A:
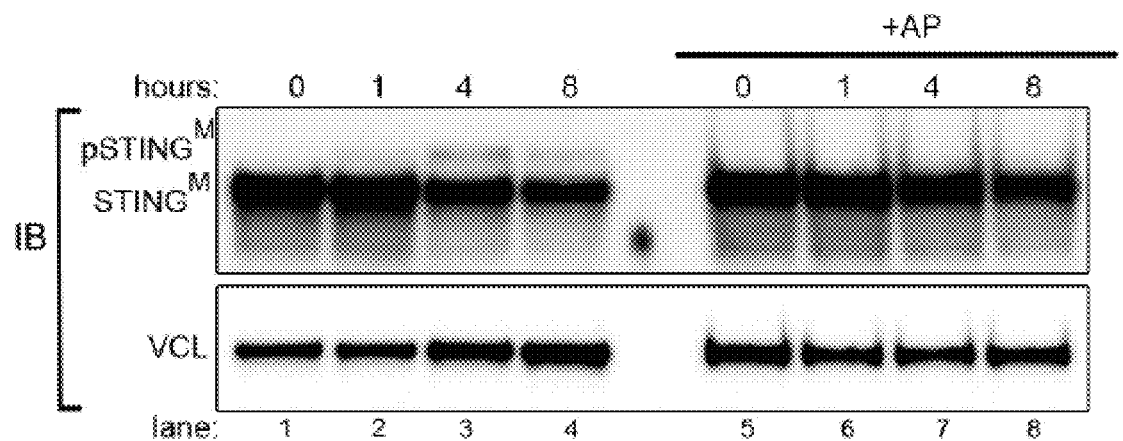

The attenuated IFN responses observed in IFI16 KO THP1 cells could be due to impaired regulation of the STING signalling cascade. To evaluate this, immunoblotting for STING, phospho-TBK1 and phospho-IRF3 was performed. Transfection of cells with dsDNA resulted in the emergence of a slow migrating form of STING (FIG. 14a, left side), possibly due to phosphorylation. To confirm this, samples were treated with alkaline phosphatase prior to SDS-PAGE electrophoresis. This resulted in disappearance of the slower migrating signal (FIG. 14a right panel). Next, control and IFI16 KO THP1 cells were transfected with dsDNA and evaluated for the appearance of the phosphorylated STING band. In control cells, this signal appeared after one hour and peaked between 4 and 6 hrs p.t. (FIG. 2d upper left panel). In contrast, cells lacking IFI16 produced a very faint and transient signal after 4 to 6 hrs p.t. (FIG. 2d upper right panel). Evaluation of TBK1 phosphorylation further indicated that control cells responded rapidly to dsDNA, whereas cells lacking IFI16 had a delayed and transient phosphorylation pattern (FIG. 2d). This attenuated response was also apparent at the level of IRF3 phosphorylation where control THP1 cells induced phosphor-IRF3 after 1 hour and peaked 8 hrs p.t., whereas IFI16 KO cells demonstrated at least a 4 hrs time delay and a weaker signal for phosphor-IRF3 (FIG. 2d, lane 2-4 versus lane 10-12).

Figure 2E:
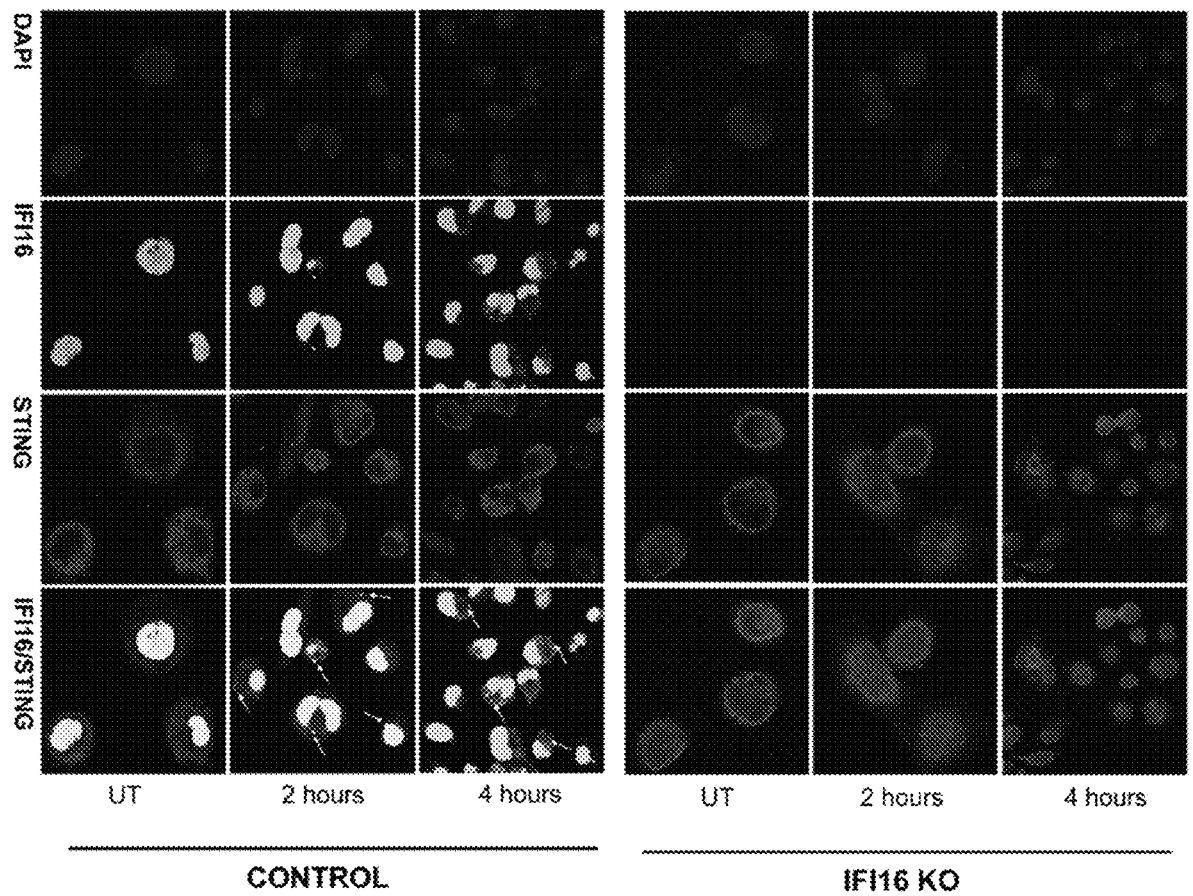
Figure 14B:
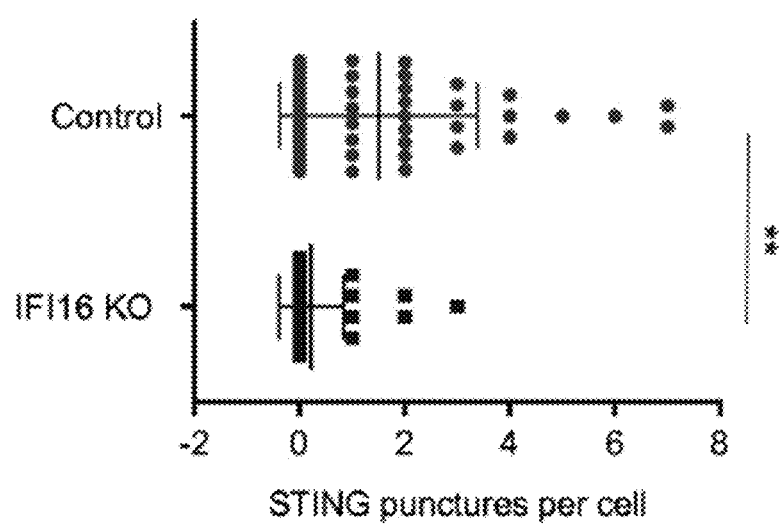
Figure 14C:
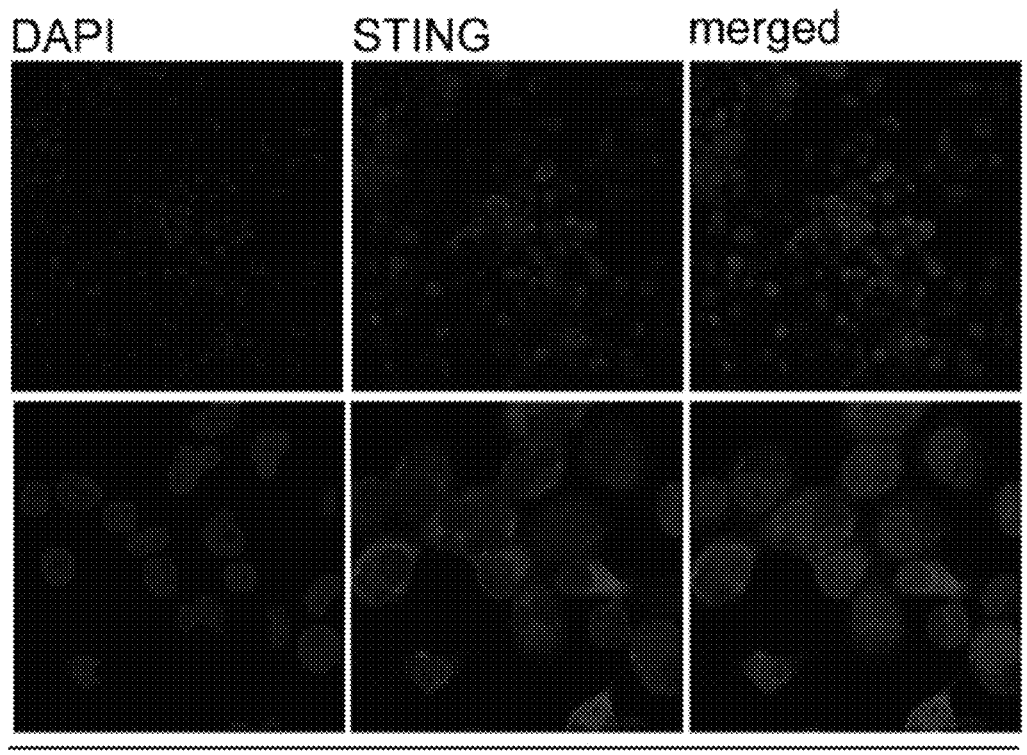
Figure 14C:
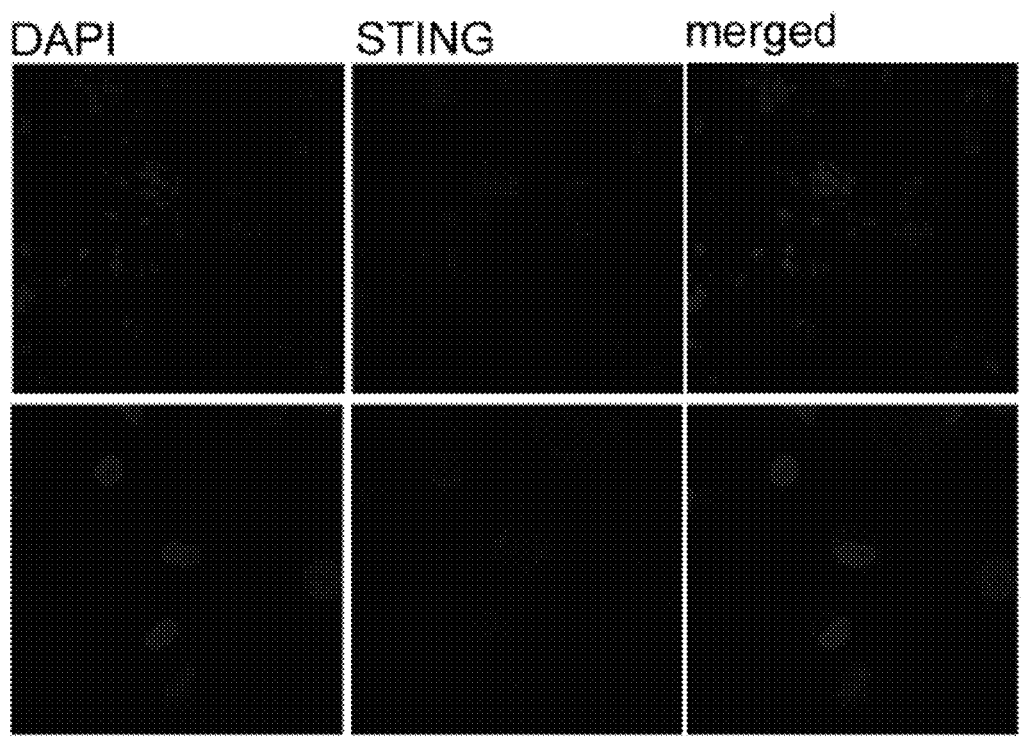

Confocal microscopy was employed to visualise the kinetic of STING activation as assessed by STING puncta formation after dsDNA transfection in both control and IFI16 KO cells. In control THP1 cells, IFI16 and STING colocalized in distinct spots with saturated DAPI staining, indicating transfected dsDNA, which was completely absent in cells lacking IFI16 (FIG. 2e). Furthermore, STING specks were clearly observed in control cells 2 hrs p.t., which further increased at 4 hrs (FIG. 2e). By contrast, THP1 cells lacking IFI16 formed no detectable specks at 2 hrs and very few at 4 hrs p.t. (FIG. 2e). This difference was significant when STING puncta were counted in multiple cells (FIGS. 14b and c). Together these data demonstrate that macrophages, which express cGAS and STING but lack IFI16, do not have the capacity to initiate early and robust STING signal some activation in response to cytosolic dsDNA.

STING Dimerization, Phosphorylation and Downstream ISG Expression is Regulated by IFI16

Figure 14D:
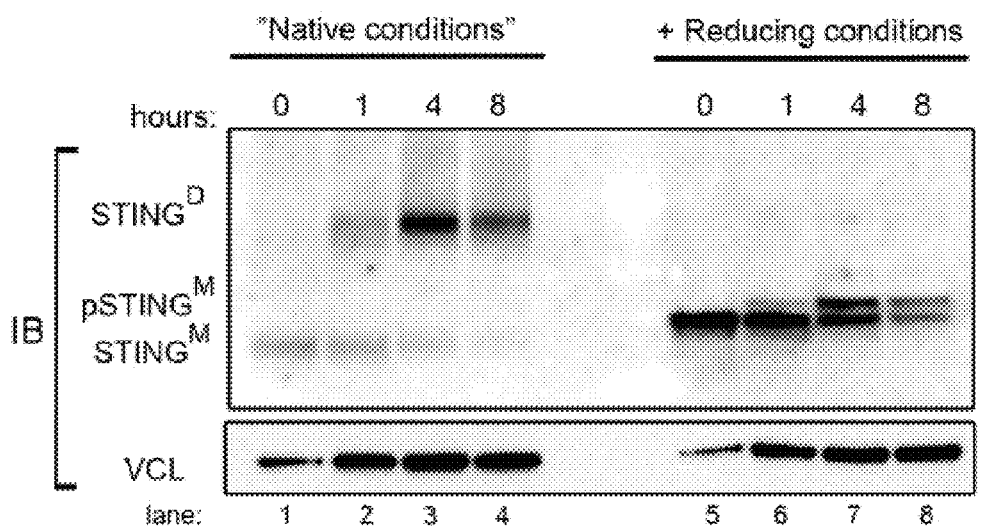
Figure 14E:
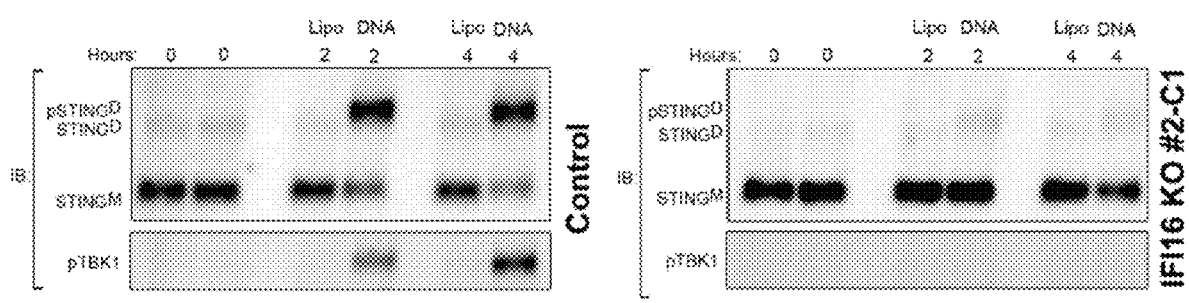

Recently, it has been shown that dimerization of STING through cGAMP interaction precedes active TBK1 phosphorylation of STING and IRF3. An in-house STING dimerization protocol described in Holm et al., 2016 was used that allows investigating the degree of dimerization, as well as level of phosphorylation of STING after dsDNA transfection. To pinpoint STING dimerization, all experiments were conducted under semi-native conditions, as reducing conditions would disrupt the dimerization but not the phosphorylation signal of STING (FIG. 14d). When control THP1 cells were stimulated with dsDNA, an immediate dimerization signal was observed that peaked in intensity after 4 hrs (FIG. 3a lane 2-4). This signal was both delayed and less intense in THP1 cells lacking IFI16 (FIG. 3a lane 10-14). Based on three individual experiments, we calculated that STING dimerization formation peaked at 4 hrs post dsDNA transfection in control THP1 cells, whereas cells lacking IFI16 demonstrated a delay of at least 4 hrs (FIG. 3b). These observations were confirmed in a IFI16 knockout clone generated with a different gRNA (FIG. 14e).

Next it was determined whether the delay in STING activation and phosphorylation is comparable in IFI16 and cGAS KO THP1 cells. As expected, control cells produced rapid STING dimerization after 1 hour. The intensity of the dimerization signal further increased 4 hrs p.t. following a fading signal for STING monomer and increased signal for phosphor-TBK1 (FIG. 3c lane 2-4). As expected, cGAS KO THP1 cells generated a very faint STING dimerization signal (FIG. 3c lane 6-8) as well as a weak signal of phosphorylated TBK1 (FIG. 3c lane 7). In cells lacking IFI16, STING dimerization and phosphorylation was not observed until 4 hrs post-transfection, in which case the signal intensity was inferior to the signals observed for the control cells (FIG. 3c; lane 2-3 versus 10-11). In parallel to the delayed and reduced dimerization of STING, it was also observed that THP1 cells lacking IFI16 did not induce TBK1 phosphorylation before 4 hours p.t (FIG. 3c lane 11).

Figure 15:
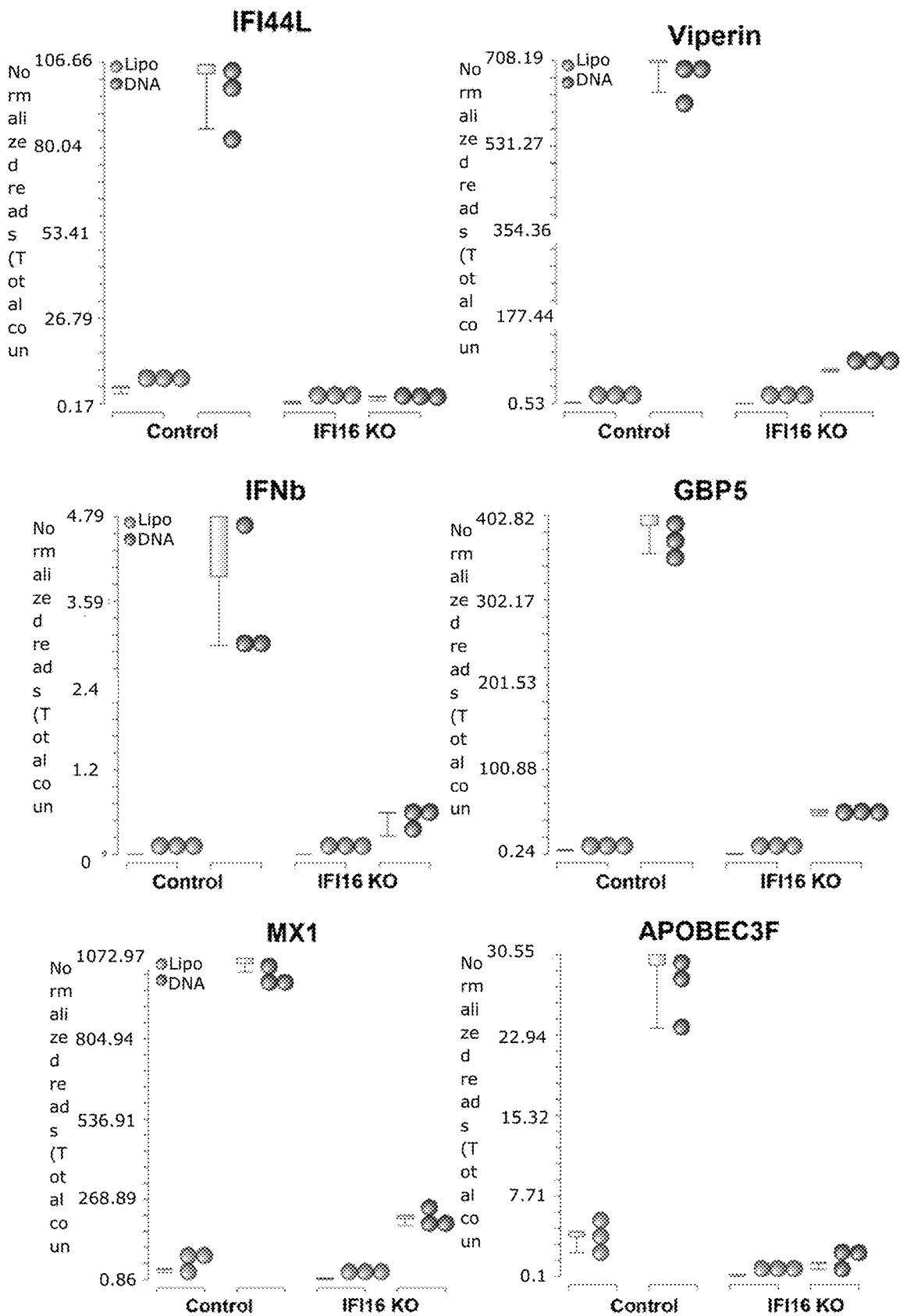

Specific phosphorylation at STING $Ser^{366}$ is essential for downstream signalling to IRF3 and its activation. Thus, STING phosphorylation was evaluated using a phosphor-specific antibody described by Liu et al., 2015 targeting $Ser^{366}$. It was confirmed that control cells stimulated with dsDNA induced a clear signal after 1 hour, which remained elevated until 8 hrs p.t. (FIG. 3d lane 2-4). This signal was absent in cGAS KO cells (FIG. 3d lane 7) and strongly attenuated in IFI16 KO cells (FIG. 3d lane 11). The attenuation and delay of STING activation observed in IFI16 KO cells would influence the capacity of macrophages to mount an early antiviral response, as indicated in FIG. 1. Examination of six classical type I IFN stimulatory genes (ISGs) showed a homogeneous increase of RNA reads in each biological sample of control macrophages stimulated with dsDNA, whereas IFI16 KO cells showed little if any differences (FIG. 15). In conclusion, these data support that IFI16 controls STING activation at or upstream of STING phosphorylation.

IFI16 Recruits TBK1 to STING to Initiate IRF3 Activation

Figure 16:
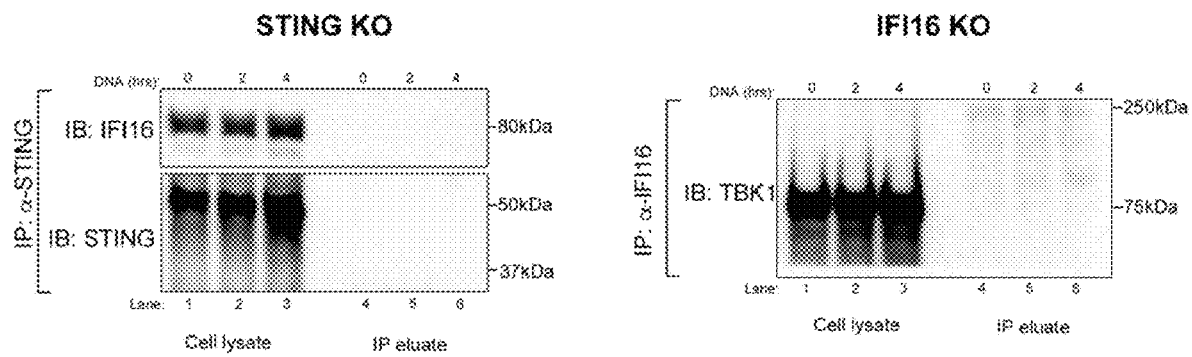

An immunoprecipitation (IP) of STING or IFI16 on cytosolic extracts from THP1 cells and MDMs stimulated with dsDNA was performed (FIG. 4). In STING-IP samples a robust signal for IFI16 was observed 2 hrs p.t. that decreased at 4 hrs p.t. (FIG. 4a, lane 2-3), whereas no IFI16 was pulled down in STING KO cells (FIG. 16). We also observed a strong association between STING and TBK1, as well as phosphor-TBK1, after DNA stimulation (FIG. 4a, lane 2). Consistent with these results, IP with IFI16 antibodies on cytosolic extracts resulted in a robust signal for STING 2 hrs p.t., which was no longer apparent at 4 hrs (FIG. 4a, lane 5-6). Additionally, it was observed that IFI16 strongly associated with TBK1 even in absence of stimulation (FIG. 4a, lane 4). This interaction was specific, since TBK1 was not precipitated by anti-IFI16 in THP1 IFI16 KO cells (FIG. 16). Upon dsDNA transfection, the phosphorylated form of TBK1 was also precipitated together with IFI16 (FIG. 4a, lane 5-6). These results were recapitulated in cell lysates from primary MDMs using the STING-IP protocol (FIG. 4b).

These data show that IFI16 may function as a bridge between STING and TBK1. To test this hypothesis, we next conducted a STING IP of control and IFI16 KO THP1 cells stimulated with dsDNA. Remarkably, TBK1 recruitment to STING was absent in cells lacking IFI16 and these cells failed to mount phosphorylation of STING at $Ser^{366}$ (FIG. 4c, lane 5-6). In contrast, control THP1 cells demonstrated both TBK1 recruitment to STING and strong phosphorylation of STING at position $Ser^{366}$ (FIG. 4c, lane 2-3). Next, we performed IP of IFI16 in STING KO THP1 cells and recapitulated the constitutive association between TBK1 and IFI16 (FIG. 4d). Collectively, these data show that IFI16 may be important for recruitment of TBK1 onto STING following dsDNA stimulation.

Figure 4E:
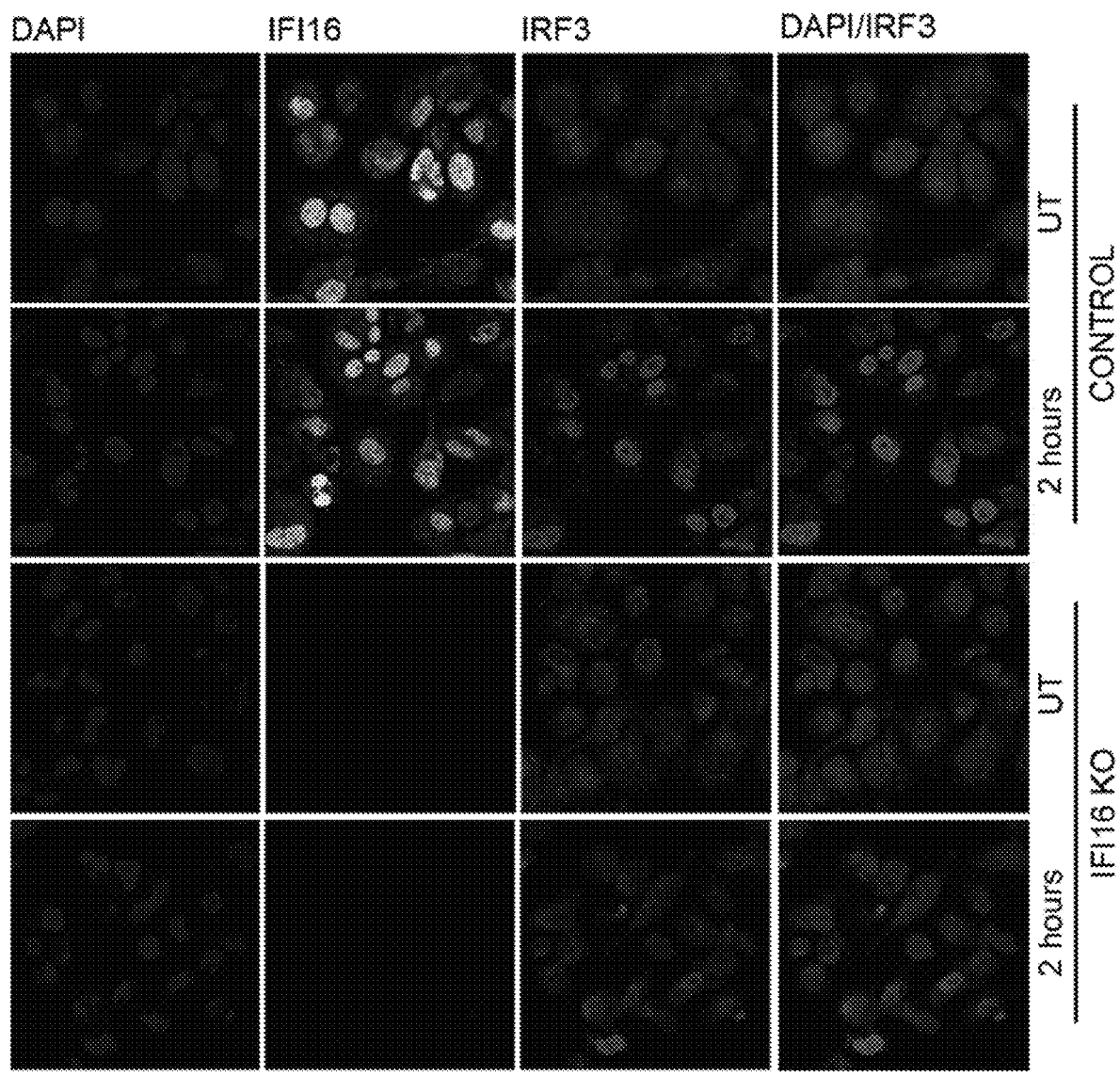
Figure 4F:
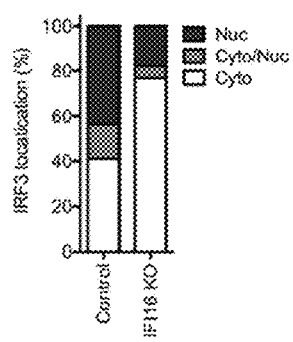

Impaired STING and TBK1 interactions should result in reduced IRF3 activation and translocation to the nucleus. Indeed, confocal microscopy confirmed IRF3 accumulation in the nucleus of control but not of IFI16 KO cells (FIGS. 4e and f). Taken together, these results suggest that IFI16 constitutively interacts with TBK1 and is able to recruit TBK1 to STING following DNA stimulation, thus supporting phosphorylation of STING and subsequent IRF3 activation.

Impaired cGAMP Production in IFI16-Deficient Cells.

Figure 5A:
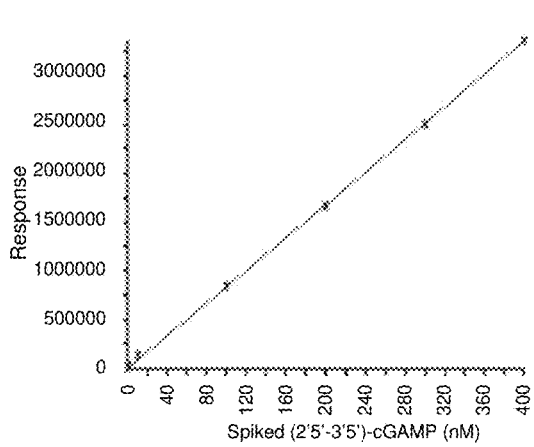
Figure 5C:
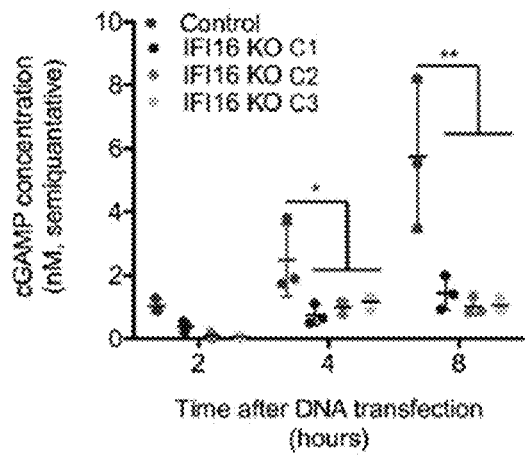
Figure 5B:
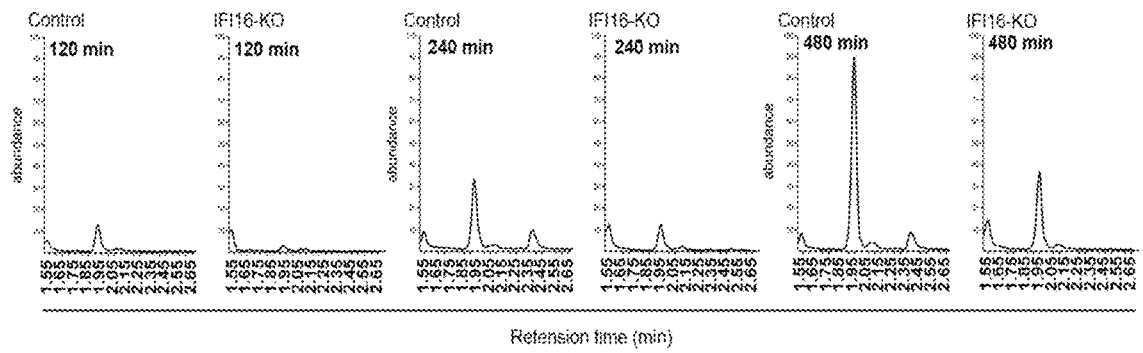
Figure 5D:
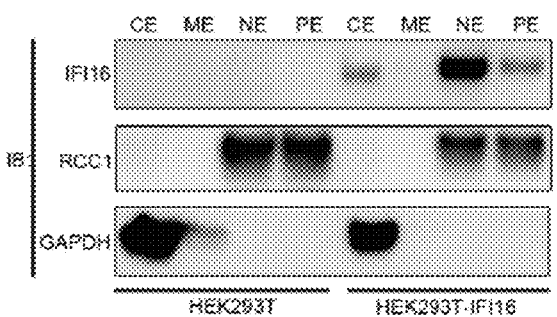

A prerequisite for DNA-stimulated STING activation and TBK1 recruitment is activation of cGAS to produce cGAMP. In dendritic cells, this process has been suggested controlled by a cellular cofactor PQBP1 during sensing of retroviral DNA. Mammalian 2'5'-3'5-cGAMP (hereafter cGAMP) was measured by LC-MS/MS analysis (FIG. 5a). Interestingly, IFI16 KO THP1 cells demonstrated much weaker cGAMP production than control cells following DNA transfection (FIG. 5b). Using the external calibration curve of synthetic cGAMP (FIG. 5a) we were able to quantify cGAMP production over multiple experiments, confirming that control THP1 cells produced significantly more cGAMP after DNA challenge than IFI16 KO clones (FIG. 5c).

Figure 5E:
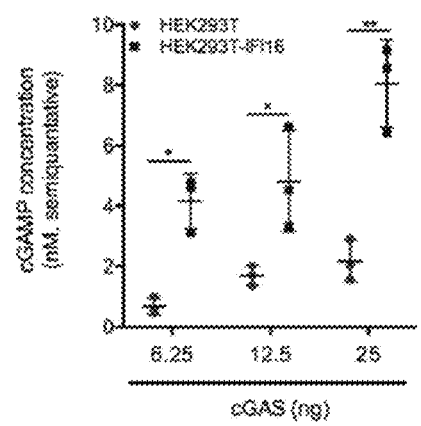

These data indicated that IFI16 directly supports the capacity of cGAS to sense DNA and activate the signalling complex. To confirm this in another system, we used HEK293T cells, which do not express IFI16, cGAS or STING, but do activate the IFNβ promoter in responsive to plasmid DNA transfection upon overexpression of STING and cGAS(Ablasser et al., 2013). Using Sleeping Beauty DNA transposon technology, a HEK293T cell model was generated stably expressing human IFI16. These cells demonstrated a distribution of IFI16 reminiscent of macrophages (FIG. 5d), with the majority of IFI16 accumulating in the nucleus, but a significant portion in the cytoplasm (FIG. 5d, CE and NE lanes). cGAS was titrated into these cells to examine whether IFI16 supported cGAMP production by cGAS in response to sensing of the transfected plasmids. Indeed, $HEK293T^{IFI16}$ cells generated significantly more cGAMP measured by LC-MS/MS than normal HEK293T cells (FIG. 5e).

It was then examined whether overexpression of IFI16 in combination with cGAS had any synergistic effect in the HEK293T stable expressing human STING (FIG. 5f). Overexpression of IFI16 alone did not render cells responsive to plasmid DNA, whereas co-expression of cGAS alone resulted in robust IFNβ promoter-stimulated luciferase activity (FIG. 5g). When we titrated increasing doses of IFI16 in $HEK293T^{STING}$ expressing cGAS we observed prominent dose-response effects of IFI16, indicating that IFI16 enhances cGAS activation (FIG. 5g).

Figure 5I:
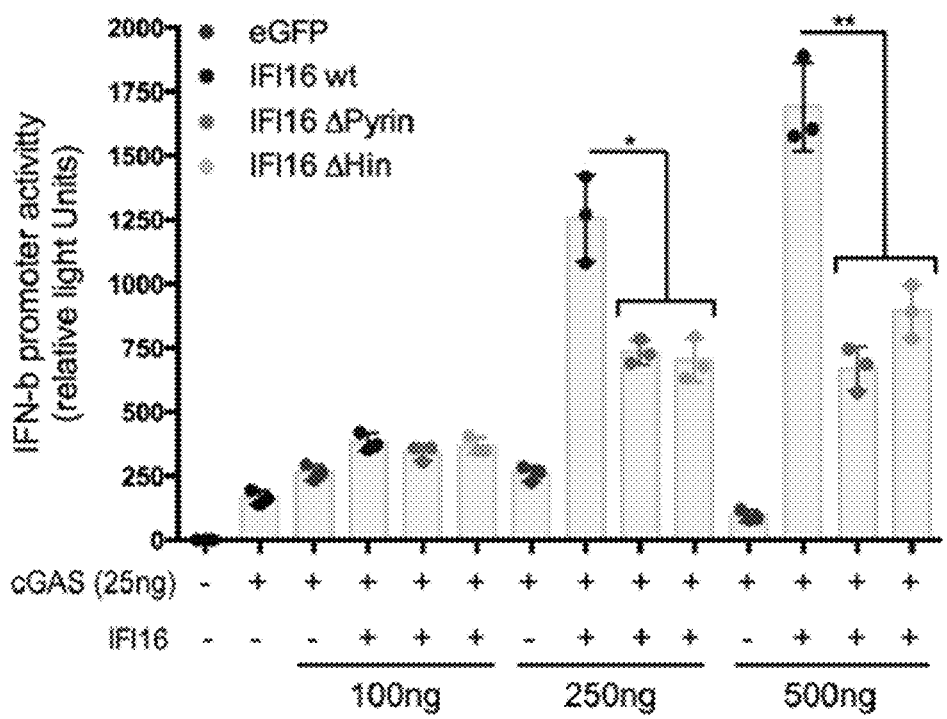
Figure 5J:
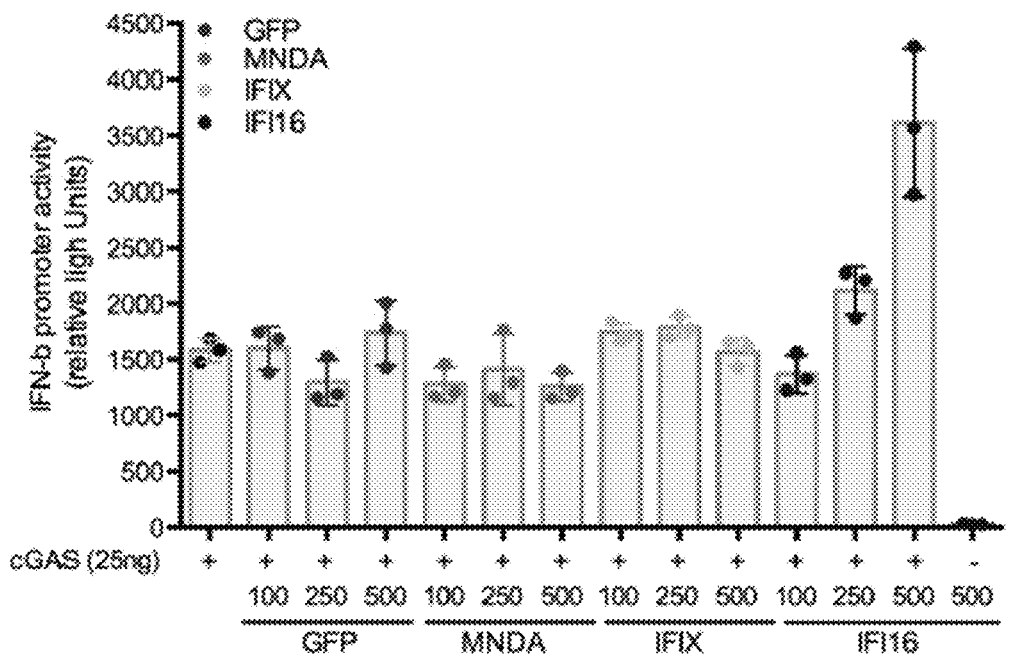
Figure 17:
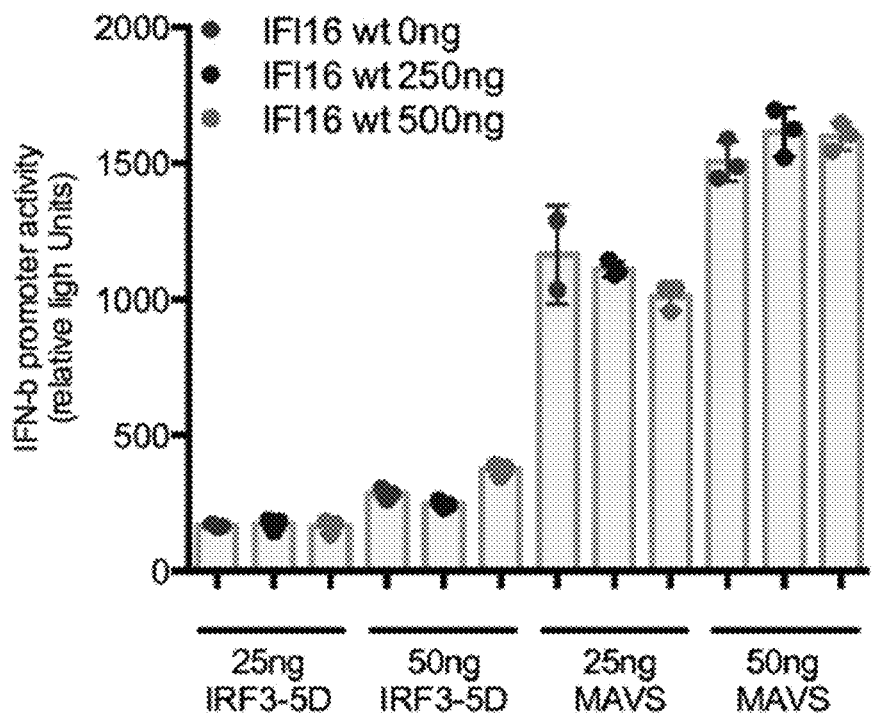

To identify the domain responsible for triggering cGAS activation, $HEK293T^{STING}$ cells were transiently transfection with two different IFI16 mutants: a PYRIN-domain mutant and a DNA-binding mutant, in which we deleted the HIN-a domain and made specific HIN-b site-directed mutagenesis (Jin et al., 2012) in residues essential for DNA binding (FIG. 5h). All IFI16 plasmids contained an IRES-BFP cassette to control for gene expression by flow cytometry (FIG. 5h). When we overexpressed any of the IFI16 constructs in a $HEK293T^{STING}$ background no IFNβ promoter activity was detected (data not shown). However, expression of cGAS in combination with wildtype IFI16 significantly elevated IFNβ promoter activity above control plasmid expression (FIG. 5i). Additionally, when each of the IFI16 mutants were co-expressed together with cGAS, we observed significantly reduced IFNβ-promotor activity compared to IFI16 wildtype. To examine whether this was a specific function by the IFI16 PYRIN domain, two other PYRIN-domain containing proteins also reported as sensors of DNA (MNDA and IFIT)(Diner et al, 2015) were overexpressed in $HEK293T^{STING}$ cells. However, increasing doses of MNDA and IFIX did not increase IFNβ-promoter activity (FIG. 5j). To further confirm specificity of IFI16 for the STING pathway, the IFNβ promoter was activated by overexpression of the phosphor-mimic IRF3 mutant IRF3-5D, or the adaptor protein MAVS (FIG. 17). Co-expression of IFI16 did not elevate IFNβ-promotor activity supporting that the function of IFI16 is specific to the STING pathway. In conclusion, IFI16 augments cGAS-dependent responsiveness to DNA, and this is dependent on the PYRIN and HIN domains of IFI16.

IFI16-Deficient Cells Display Impaired cGAMP-Directed STING Activation

It was determined whether the immune response in IFI16 KO THP1 cells was normalized when bypassing the cGAS-DNA sensing mechanism. This was done by stimulating cells directly with cGAMP. As expected, control cells and cGAS KO THP1 cells demonstrated a clear type I IFN response 4 and 8 hrs after infusion with cGAMP, whereas STING KO cells were insensitive to cGAMP stimulation (FIG. 6a).

Figure 6A:
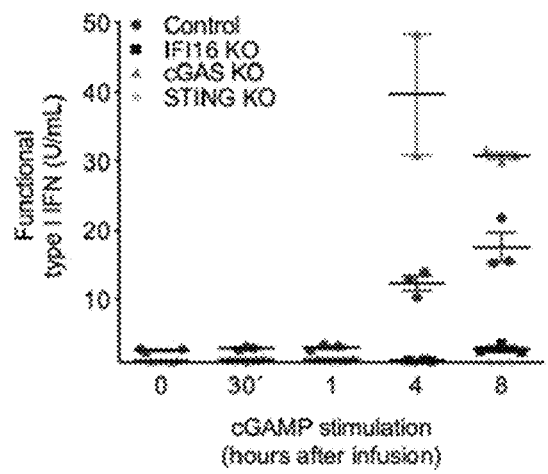
Figure 6B:
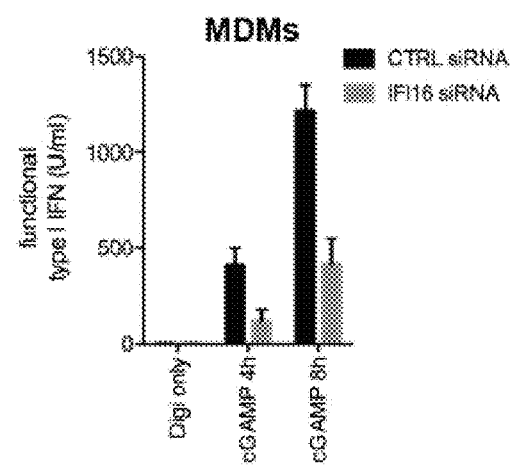
Figure 18:
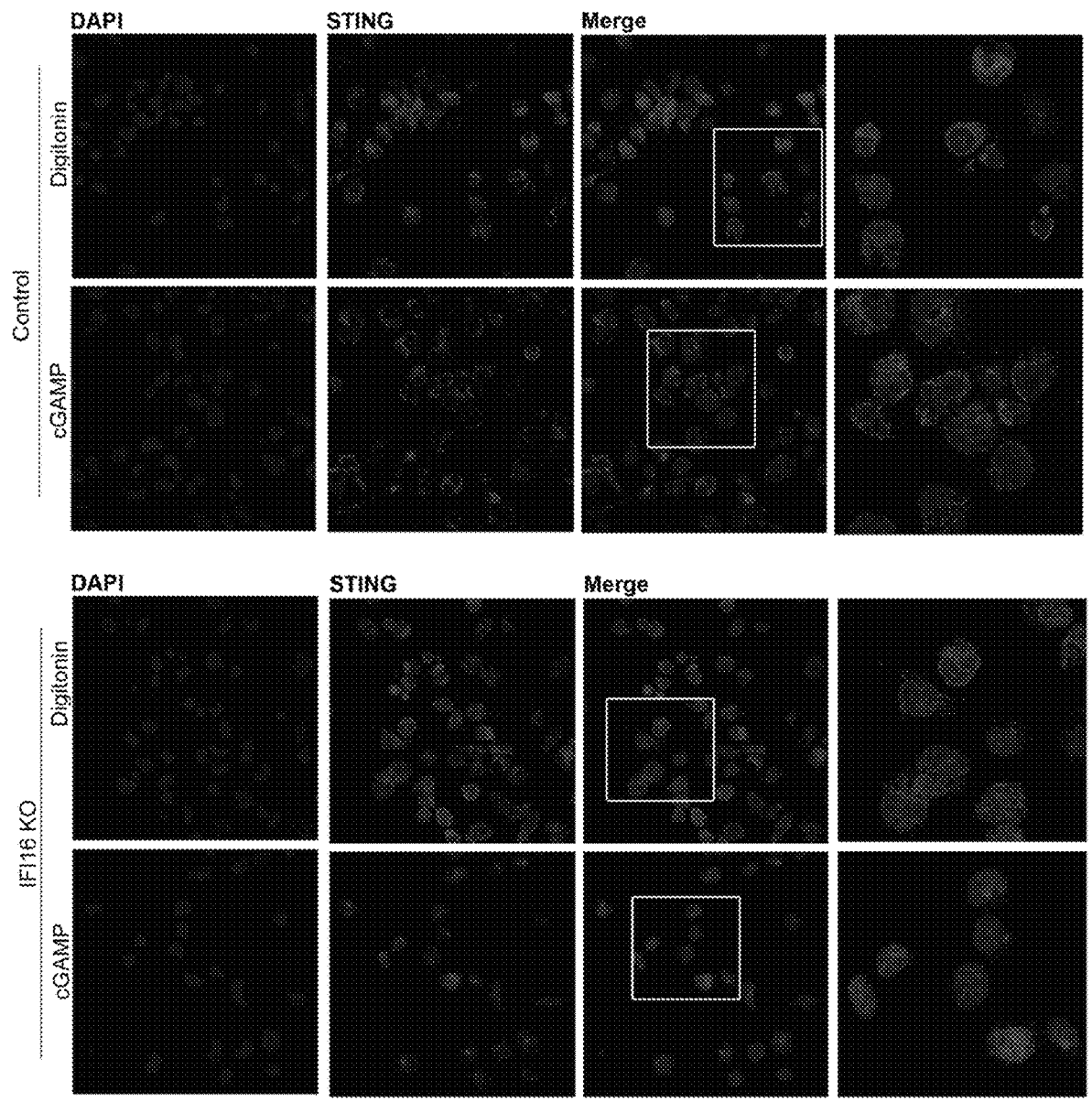

Interestingly, IFI16 KO cells behaved in a similar manner as STING KO cells (FIG. 6a). In MDMs cGAMP infusion resulted in strong type I IFN responses in cells treated with scrambled siRNA whereas the response was significantly lower in MDMs treated with IFI16-specific siRNA (FIG. 6b). Using confocal microscopy we observed that control cells stimulated with cGAMP generated specific STING patterns, including multiple small cytoplasmic puncta and larger aggregations, in ER-like formations (FIG. 18). In contrast, IFI16 KO cells generated small aggregates in ER but no cytoplasmic spots (FIG. 18), indicating that IFI16 participate in regulating the function of STING downstream of cGAMP activation.

Figure 6C:
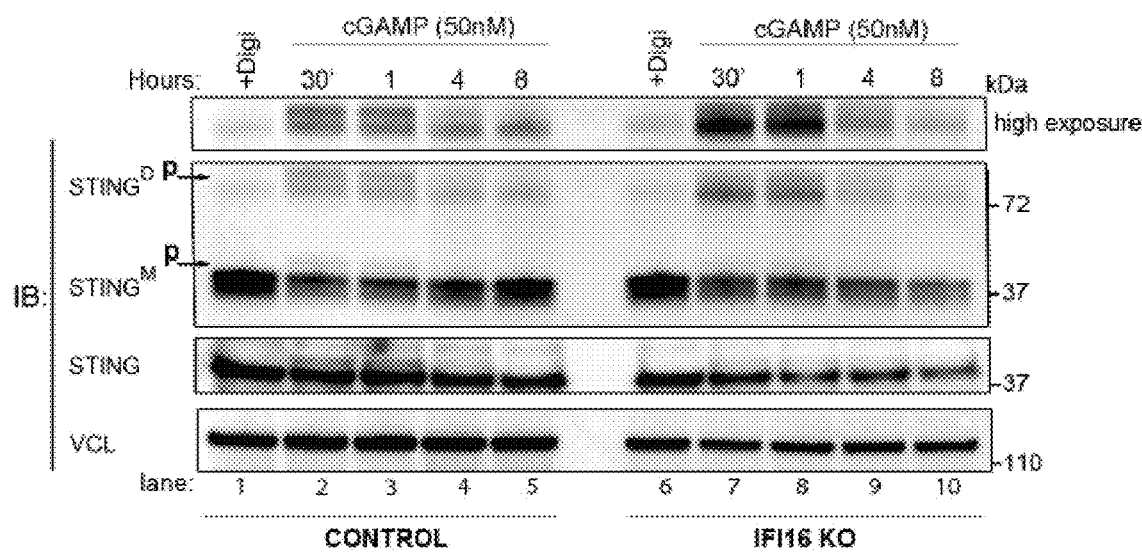
Figure 6D:
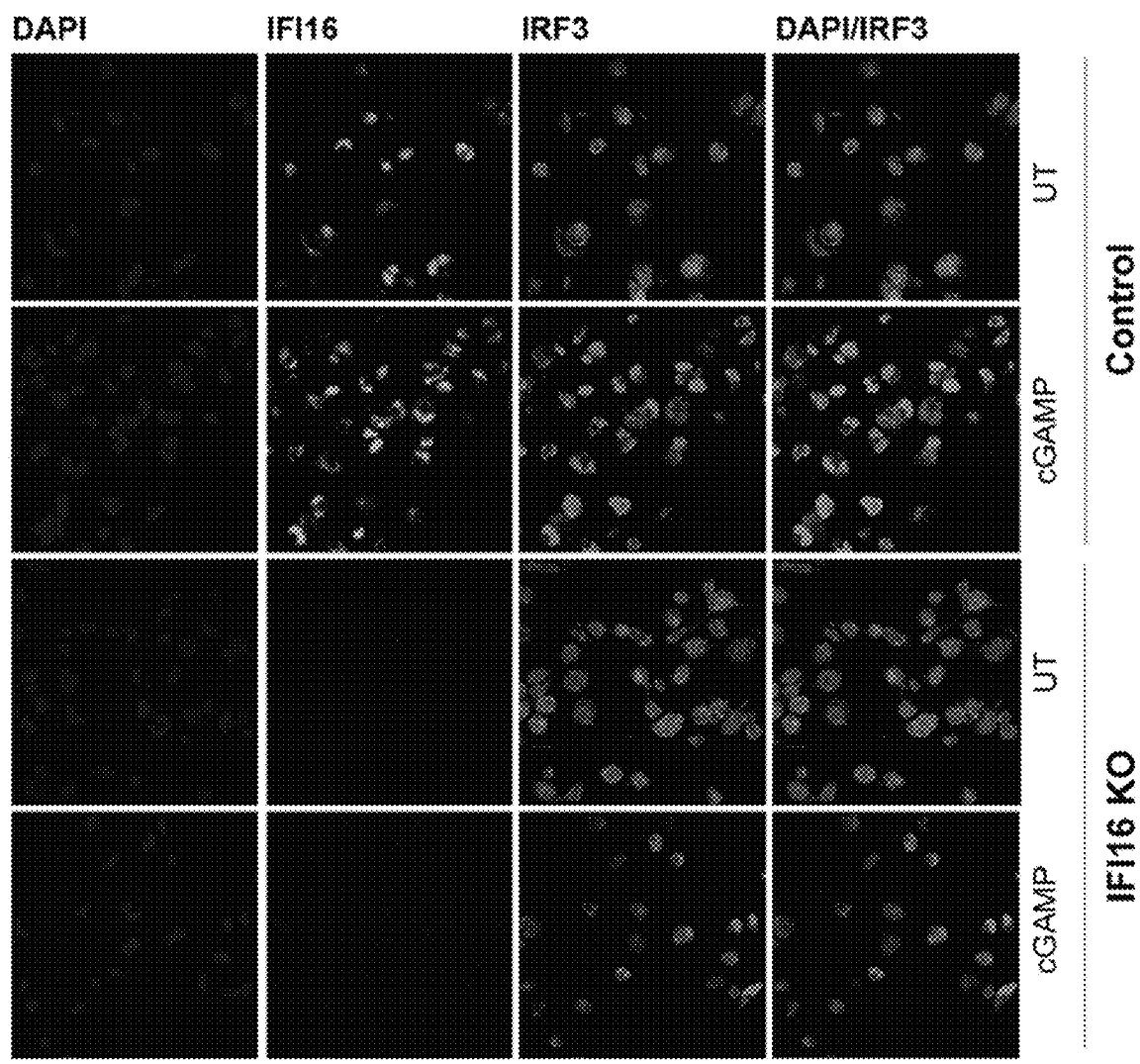
Figures 6E, 6F:
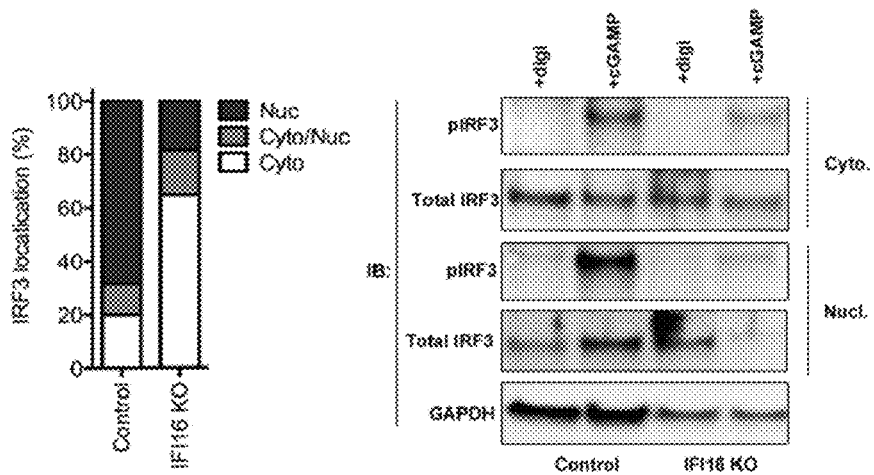

Next, the kinetics of STING dimerization was evaluated and phosphorylation in cells stimulated with cGAMP infusion. Digitonin alone did not result in STING dimerization (FIG. 6c). However, upon stimulation with cGAMP, control THP1 cells demonstrated effective shift in STING dimerization after just 30 min (FIG. 6c). Unexpectedly, IFI16 KO THP1 cells produced a strong STING dimerization signal. However, this was not phosphorylated as observed for the control cells (FIG. 6c high exposure plot; lane 2-3 versus 7-8), suggesting a lack of TBK1 recruitment to the STING dimerization complex in absence of IFI16, which support earlier findings (see FIG. 4). This reduced STING phosphorylation would predict impaired IRF3 activation. This was confirmed by confocal microscopy visualising IRF3 nuclear translocation one hour after cGAMP infusion (FIG. 6d). When multiple cells were evaluated, increased nuclear accumulation of IRF3 in control versus IFI16 KO cells was found (FIG. 6e). These results are supported by immunoblotting for phosphor-IFR3 in lysates from control and IFI16 KO cells stimulated with cGAMP demonstrating strong signals for IRF3 phosphorylation in cytoplasmic fractions of control cells and a very faint signal in IFI16 KO cells (FIG. 6f). In nuclear fractions we observed an about 50% reduction of the signal for phosphor-IRF3 in IFI16 KO cells (FIG. 6f), recapitulating the observations from the confocal microscopy.

Altogether, these results indicate that IFI16 not only cooperates with cGAS to promote cGAMP production but also has a key function downstream of cGAMP-STING interaction involving its recruitment of TBK1 to STING for phosphorylation.

Figure 19D:
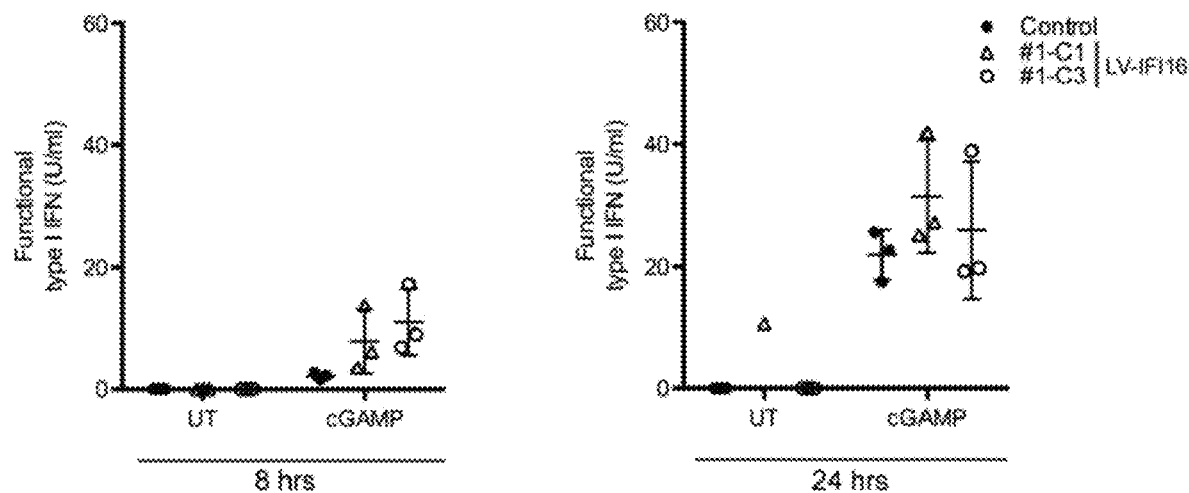
Figure 19E:
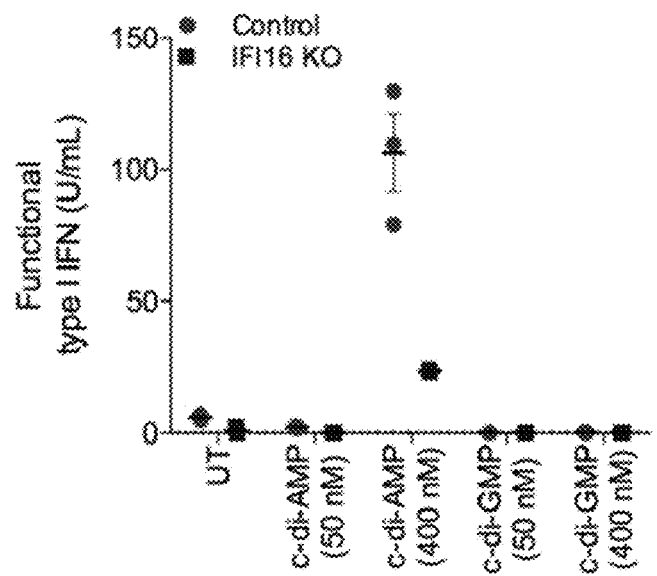

The IFI16 PYRIN Domain is Essential for Promoting cGAMP-Mediated STING Signalling The data presented above suggest that IFI16 and TBK1 cooperate for effective activation of STING. To determine at which step IFI16 acts in the cGAMP-activated pathway, STING dimerization and phosphorylation was measured in control, IFI16 KO, and TBK1 KO THP1 cells. First, it was confirmed that TBK1 KO cells stimulated with cGAMP do not produce type I IFN (FIG. 19a). Multiple THP1 IFI16 KO clones were also evaluated for their response to low (50 nM) and high (400 nM) cGAMP infusion, demonstrating minimal type I IFN production (FIGS. 19b and c). To exclude off-target effects in the THP1 IFI16 KO clones, IFI16 was reconstituted in two individual KO clones by lentiviral transduction prior to cGAMP infusion. These cells responded to cGAMP in a similar manner as THP1 control cells (FIG. 19d). It is known that STING can also be activated by bacterial cyclic di nucleotides such as cyclic-di-AMP. It was found that THP1 cells infused with high and low doses of cyclic-di-AMP responded to high doses of c-di-AMP in an IFI16 dependent manner (FIG. 19e).

Figure 7A:
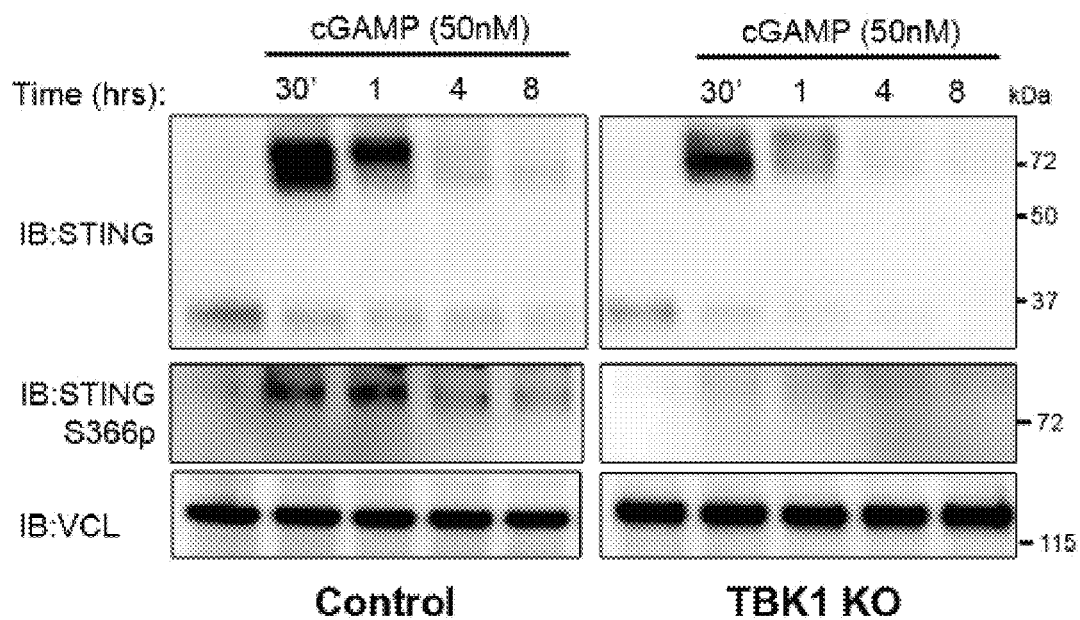
Figure 7B:
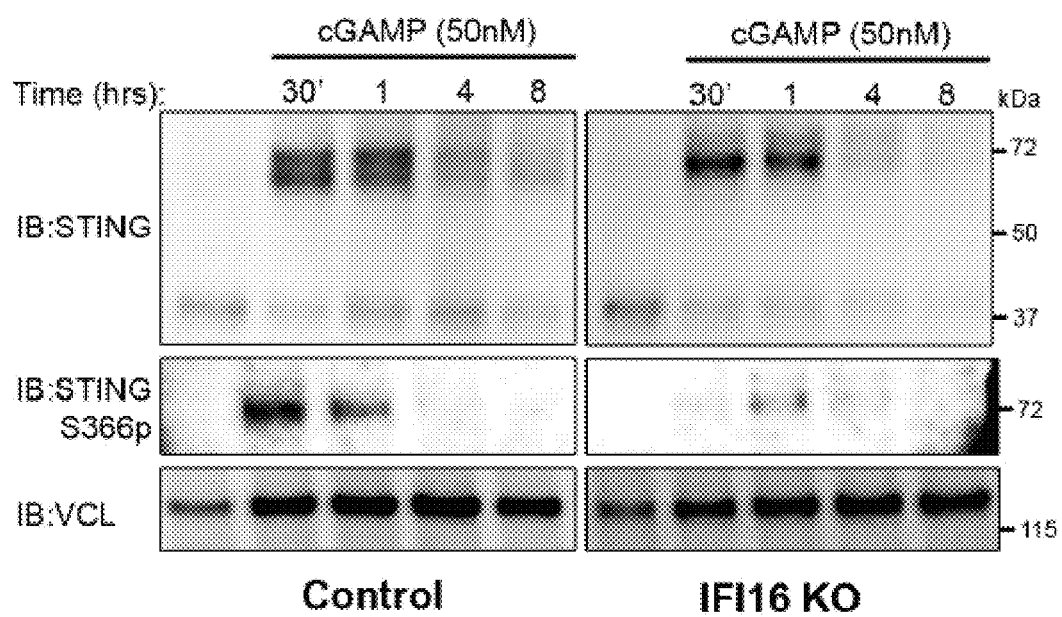

Next STING dimerization was investigated and it was observed that TBK1 KO cells produced STING-dimers at levels similar to control cells at early time points p.i. (FIG. 7a), which was also similar to IFI16 KO cells (FIG. 7b). However, in both cases the slower migrating phosphorylated band seen in the control cells was not detected. Then the degree of direct STING phosphorylation at $Ser^{366}$ as evaluated. Control THP1 cells mounting a robust phosphor-signal 30 min to 1 hour after cGAMP infusion (FIGS. 7a and 7b) but as expected, no signal was detected in TBK1 KO cells (FIG. 7a). Moreover, in IFI16 KO cells merely a very weak STING $Ser^{366}$ phosphor-signal 1 hour after stimulation was observed (FIG. 7b).

Figure 7C:
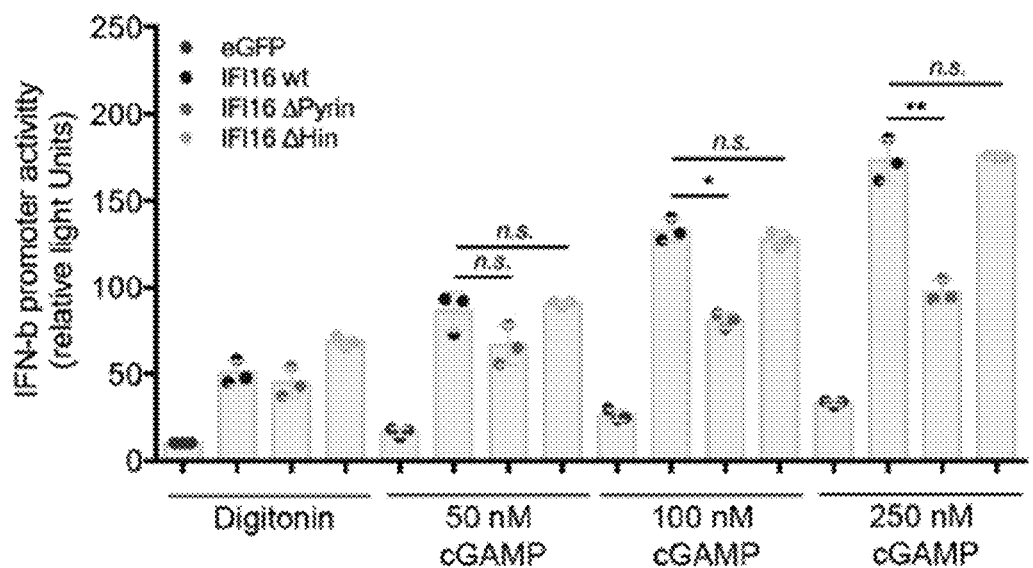
Figure 20:
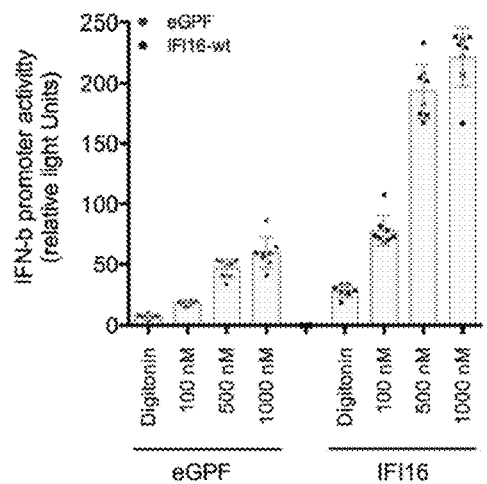
Figure 21:
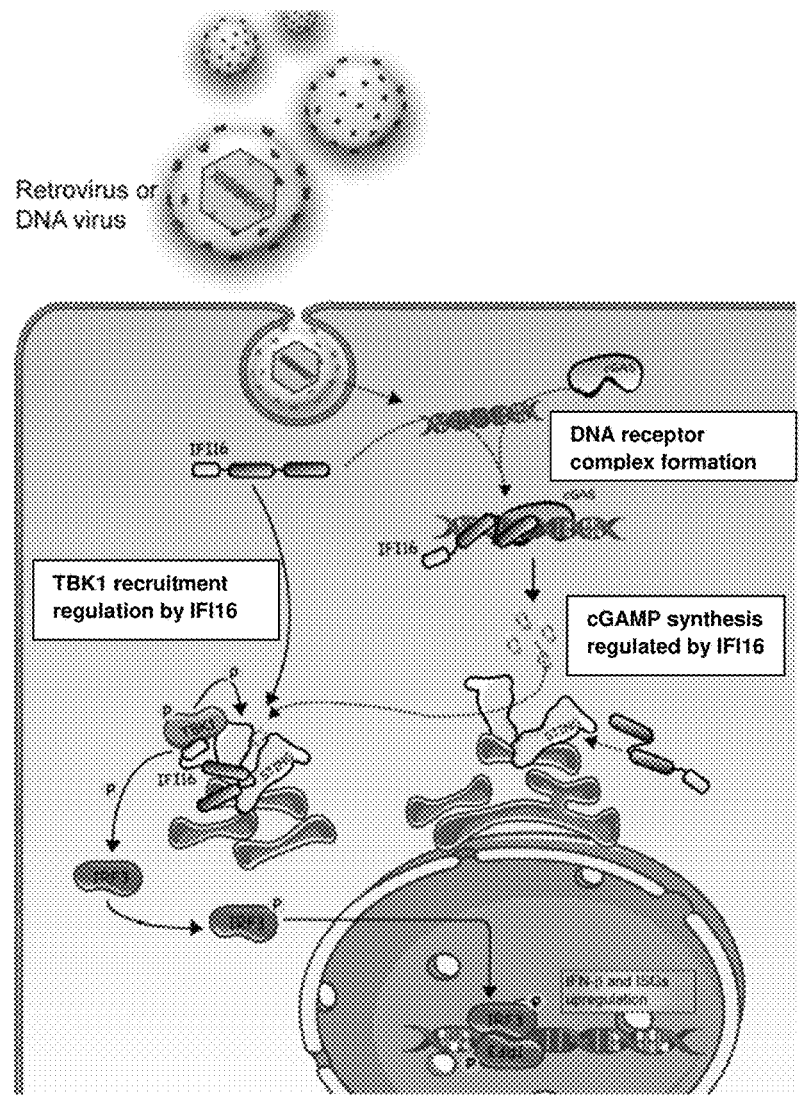

The IFI16 PYRIN domain engages in protein-protein interactions, while the HINb domain is central for DNA binding. To identify the domain(s) responsible for triggering STING activation after cGAMP stimulation, IFNβ promoter activity in HEK293T$^{STING}$ cells overexpressing the various IFI16 constructs was evaluated (see FIG. 5i). In cells expressing wildtype IFI16, a significant increase in the IFNβ promoter-stimulated luciferase activity response to cGAMP was observed compared to cells expressing eGFP only, which was saturated between 500 and 1000 nM cGAMP (FIG. 20). Interestingly, the ΔHin-IFI16 mutant augmented reporter gene expression to the same extent as wildtype IFI16, whereas the ΔPyrin-IFI16 mutant was impaired in enhancing cGAMP-stimulated STING dependent IFNβ promoter activation (FIG. 7c). To exclude the possibility that cell activation levels had been oversaturated by infusion of high doses of recombinant cGAMP, the response of cGAMP production inside HEK293T was also investigated and possible transfer to other cells through gap-junctions.

Figure 7D:
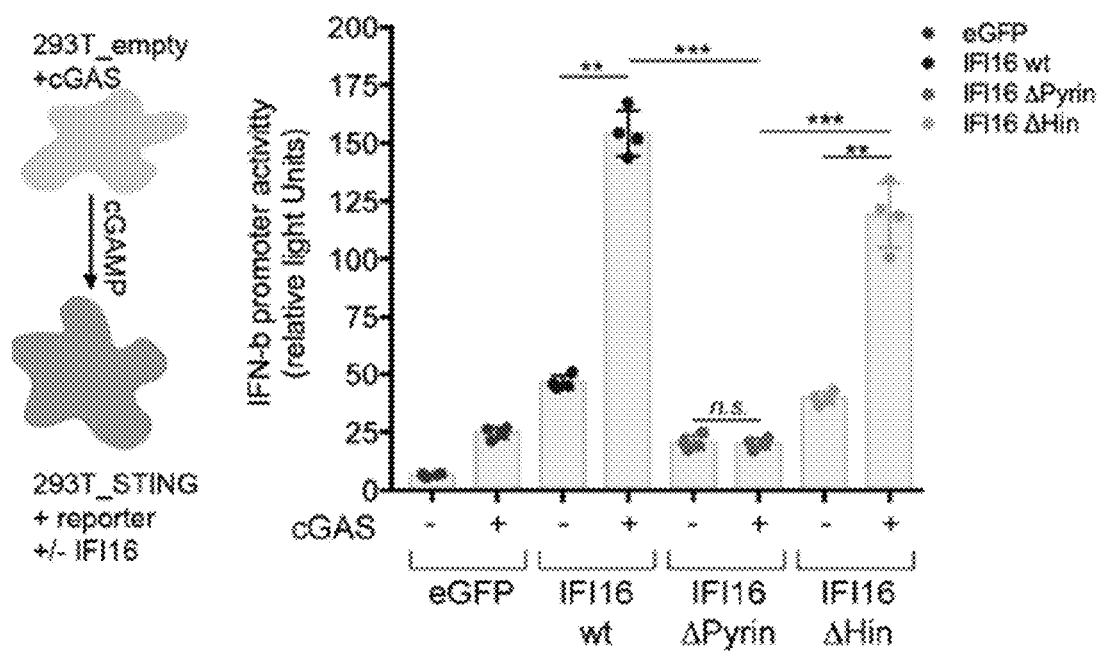

HEK293T cells were transfected with cGAS-expressing plasmid and subsequently co-cultured with HEK293T$^{STING}$ co-expressing one of the three IFI16 variants. Co-culturing cGAS-expressing cells with HEK293T$^{STING}$ resulted in minor IFNβ promoter-stimulated luciferase activity (FIG. 7d). Co-expressing eGFP from control plasmid resulted in low IFNβ activity possible due to a direct STING activation, but when these cells were co-cultured with cGAS-expressing cells the IFNβ promoter-stimulated luciferase activity significantly increased above background levels (FIG. 7d). When HEK293T$^{STING}$-IFI16 cells were co-cultured with cGAS-expressing cells, the IFNβ promoter-stimulated luciferase activity significantly increased, once again indicating that IFI16 expression supports cGAMP-transferred activation of STING. A similar response was observed when the ΔHin-IFI16 mutant was investigated (FIG. 7d). Finally, overexpression of the ΔPyrin-IFI16 did not increase IFNβ promoter-stimulated luciferase activity (FIG. 7d), indicating that the protein-protein interaction domain of IFI16 is necessary for efficient activation and signalling of STING following cGAMP production.

Materials and Methods

Cyclic [G(2',5')pA(3',5')p] (cGAMP) was obtained from BioLog. For details regarding dsDNA (HSV1-60mer) see Unterholzner et al., 2010 and ssDNA1 see Jakobsen et al., 2013. Herring testis DNA was from Sigma Aldrich (D6898); BX795 (tlrl-bx7) and poly I:C (tlrl-pic) were both acquired from InvivoGen.

Plasmids

IFI16 mutant plasmid constructs were originated from a pCDNA3 human IFI16-HA tagged expression construct kindly provided by Professor Andrew Bowie, Trinity College Dublin. Overlap extension PCR was used to construct a Pyrin domain (consisting of amino acids 87-729 of IFI16 of SEQ ID NO:2) or a DHIN-A domain+HIN-B domain specific mutations (consisting of amino acids 1-191 and 460-729 of IFI16 of SEQ ID NO:2 and the point mutations K572A, K607A, R611A, S614A, K618A, N654A, K676A, K678A, K703A). Each PCR product was then recloned into a BamHI- and XhoI-digested pCCL-PGK-eGFP together with a PCR-amplified IRES-BFP fragment by NEBuilder HiFi DNA Assembly according to manufactures instructions. For illustration see FIG. 5h.

The mBanana-cGAS fusion construct was engineered by PCR amplification of mBanana and cGAS and subsequent cloning into a NotI-digested pT2/CMV-eGFP.SV40-neo by NEBuilder HiFi DNA assembly according to manufactures instructions.

Cell Culture.

Human acute monocytic leukemia cell line (THP-1) was cultured in RPMI 1640 (Lonza) supplemented with 10% heat inactivated fetal calf serum, 200 IU/mL Penicillin, 100 µg/mL Streptomycin and 600 µg/mL glutamine (hereafter termed RPMI complete). Mycoplasma infection was tested and ruled on a monthly basis using Lonza MycoAlert kit (LT07-703). To differentiate THP-1 cells into adherent phenotypically macrophages, cells were stimulated with 100 nM Phorbol 12-myristate 13-acetate (PMA, Sigma Aldrich 79346 5MG) in RPMI complete for 24 hours before medium was refreshed with normal RPMI complete and allowed to further differentiate an additional day (hereafter defined as macrophages). Of note, the haplotype of STING in the THP-1 parental cell type has been identified to be HAQ.

Peripheral Blood Mononuclear cells (PBMCs) were isolated from healthy donors by Ficoll Paque gradient centrifugation (GE Healthcare). Monocytes were separated from PBMCs by adherence to plastic in RPMI 1640 supplemented with 10% AB-positive human serum. Differentiation of monocytes to macrophages was achieved by culturing in Dulbecco's Modified Eagle Medium (DMEM) supplemented with 10% heat inactivated AB-positive human serum; 200 IU/mL Penicillin; 100 µg/mL Streptomycin and 600 µg/mL glutamine for 10 days in the presence of 10 ng/mL M-CSF (R&D Systems).

HEK293T cells were cultured in Dulbecco's Modified Eagle Medium (DMEM) supplemented with 10% heat inactivated FCS; 200 IU/mL Penicillin; 100 µg/mL Streptomycin and 600 µg/mL glutamine. HEK-Blue™ IFN-α/β (InvivoGen) cells were cultured in DMEM supplemented with 10% heat inactivated FCS; 200 IU/mL Penicillin, 100 µg/mL Streptomycin, 600 µg/mL glutamine, 100 µg/mL normocin (InvivoGen), 30 µg/mL blasticidin (InvivoGen) and 100 µg/mL zeocin (InvivoGen).

TZM-bl indicator cells (kindly provided by Drs. Kappes and Wu and Tranzyme Inc. through the NIH AIDS Reagent Program) were cultured in Dulbecco's Modified Eagle Medium (DMEM) supplemented with 10% heat inactivated FCS; 200 IU/mL Penicillin; 100 µg/mL Streptomycin and 600 µg/mL glutamine.

Viruses.

Newcastle Disease Virus (NDV) was kindly provided by professor Peter Palese (The mount Sinai Hospital, USA); HSV1+17 and hCMV (AD169) viral strains were propagated in-house.

VSVg-pseudotyped Vpx-packed particles were generated by transfecting HEK293T cells with the plasmid pMD.2G and SIV3+ (containing all SIVmac proteins except Env, kindly provided by professor Gregory Towers, UCL). Supernatants were harvested after 48 hours, concentrated through a 20% sucrose cushion. Viral pellets were resuspended in PBS, DNase treated and stored at −80° C. Each Vpx prep was concentration determined by p24 ELISA and used at 125 µg p24 setup.

Transduction of THP-1 Cells with Lentiviral CRISPR/Cas9

We employed the CRISPR/Cas9 system to generate a set of THP-1 single clones with specific gene knockouts. Specifically, we used a lentiviral CRISPR/Cas9 vector described by van de Weijer et al., 2014 that encodes a codon-optimized nuclear-localized Cas9 gene N-terminally fused to the puromycin resistance gene via a T2A ribosome-skipping sequence. Additionally, the vector contains a human U6 promoter driving expression of a guideRNA (gRNA) consisting of a gene-specific CRISPR RNA (crRNA) fused to the trans-activating crRNA (tracrRNA) and a terminator sequence. The gene-specific crRNA sequences cloned were:

For Control KO cells we used the gene of beta-2-microglobulin (5'-GAGTAGCGCGAGCACAGCTA-3'(SEQ ID NO: 31)); for IFI16 KO (#1; 5'-GTACCAACGCTTGAAGACC-3'(SEQ ID NO: 32)), (#2; 5'-GTTCCGAGGTGATGCTGGTT-3'(SEQ ID NO: 33)) or (#3; 5'-GACCAGCCCTATCAAGAAAG-3'(SEQ ID NO: 34)); for cGAS KO (5'-GACTCGGTGGGATCCATCG-3'(SEQ ID NO: 35)); for STING KO (5'-GAGCACACTCTCCGGTACC-3'(SEQ ID NO: 36)); and for TBK1 KO (5'-GTCAGATTCTGGTAGTCCAT-3'(SEQ ID NO: 37)). VSVg-pseudotyped lenti-CRISPR virions were produced by transfecting HEK293T cells with the following plasmids: CRISPR/Cas9 vector, pMD.2G, pRSV-REV, and pMDIg/p-RRE. Viral supernatants were harvested after 72 hrs and used to transduce THP-1 cells by infection in the presence of 4 ug/ml polybrene. Transduced cells were selected with 2 µg ml$^{-1}$ puromycin at 2 days post transduction. After two weeks a single cell suspension culture was established using limiting dilution. After three weeks individual clones were subjected to western blotting to confirm absence of the targeted gene products. At least 15 clones were then assessed for proper cell proliferation and expansion, and dismissed if they were slow growing or increased cell death.

Reconstitution of IFI16 by Lentiviral Transduction.

For the IFI16 reconstitution, the lentiviral vector pCCL/PGK-IFI16 was generated by inserting a PCR amplified IFI16 fragment from pCCL/CMV-DH287-IRES-BFP into BamHI- and XhoI-digested pCCL-PGK-eGFP by NEBuilder HiFi DNA assembly. Packaging plasmids pMD2.G, pRSV-Rev and pMDIg/pRRE were calcium phosphate-transfected together with pCCL/PGK-IFI16 into HEK293T cells. Vector-containing supernatants were harvested by filtration through a 0.45 µm filter (Sarstedt) and ultracentrifuged at RPM 25,000 at 4° C. for 2 hr on a 20% sucrose cushion. Pellets were re-suspended in PBS and stored at −80° C. Two hundred and fifty ng p24 LV-IFI16 inoculums were then used to infect 1-day old PMA-differentiated THP1 IFI16 KO cells using 6 ug/ml polybrene. Forty-eight hours later, cells were stimulated with DNA or cGAMP. Supernatant was harvest after 8 or 20 hrs for type I IFN bioassay and cells were lysed for verification of IFI16 expression by immunoblotting.

Transfection of HEK293T Cells

Human Embryonic Kidney 293T (HEK293T) cells were stably transfected with wild type human STING using the sleeping beauty-mediated transposition system. Human STING and SB100X encoding vectors were mixed with Polyethyleneimine in a 1:3 relationship and administered to the cells which were allowed to incubate for 48-hours. Cells were subsequently selected with 1 µg ml$^{-1}$ puromycin for two weeks and allowed to expand before analyzing stable expression of STING via western blotting.

DNA/RNA Stimulation of Cells

Standard stimulation of primary macrophages and two-days PMA-differentiated THP-1 with dsDNA, ssDNA and poly (I:C) was conducted on 2×10^5 cells in a 24-well format with 500 ul medium using lipofectamine 2000 (Life Technologies 11668-019) as carrier. Transfection protocols were as according to the manufacturer's instructions using a ratio of lipo-DNA/RNA of 1:1. For experimental details regarding concentration of DNA/RNA and time points before supernatant harvest and lyses of cells see figure legends.

cGAMP Stimulation of Cells

Two-hundred thousand PMA-differentiated THP-1 cells in 24-well plates were permeabilized with digitonin permeabilization buffer (50 nM HEPES, 100 mM KCl, 3 mM $MgCl_2$, 0.1 mM DTT, 85 mM sucrose, 0.2% BSA, 1 mM ATP, 1 mM GTP, pH 7) containing 5 µg/mL digitonin in the presence or absence of cGAMP. After incubation at 37° C. for 10 min, the permeabilization buffer was removed and replaced with warm RPMI medium with 10% FCS and 600 µg/mL glutamine. For experimental details regarding concentration of cGAMP and time points before supernatant harvest and lyses of cells see figure legends.

Functional Type I IFN Assay

To quantify functional type I IFN the reporter cell line HEK-Blue™ IFN-α/β (InvivoGen) was utilized according to the manufacturers instructions. Thirty thousand HEK-Blue cells were seeded in a 96-well plates with 150 µl medium devoid of Blasticidin and Zeocin and given 50 µl supernatant the next day. This cell line expresses secreted embryonic alkaline phosphatase under the control of the IFN-α/β inducible ISG54 promotor. SEAP activity was assessed by measuring optical density (OD) at 620 nm on a micro plate reader (ELx808, BioTEK). The standard range was made with IFN-α (A2) (PBL Assay Science).

Enzyme-Linked Immunosorbent Assay

Protein levels of the cytokines CXCL10 and TNF-α in supernatants, were measured using ELISA kits from Pepro-Tech (CXCL10; 900-T39.) and BioLegend (TNF-α; 430201.) following the manufacturer's instructions.

RNA Analysis

Gene expression was determined by real-time PCR, using TaqMan detection systems (Applied Biosciences). Genomic RNA from cells was collected using the High Pure RNA Isolation kit (Applied Bioscience) and RNA was quality controlled by Nanodrop spectrometry. RNA for human ISG54 (HS00533665), IFNβ (Hs01077958_s1), RNaseP (ThermoFisher #4316844) and DAG1 (HS00189308_M1) were analyzed with premade TaqMan assays and the RNA-to-$C_t$-1 kit following manufactures procedures (Applied Biosciences). The MX3005 (Stratagene) was used for PCR quantification.

Western Blot

Generally, 2×10^5 cells were lysed in 150 ul Pierce RIPA buffer (Thermo Scientific) supplemented with 10 mM NaF, 1× complete protease cocktail inhibitor (Roche), 0.2% SDS, 1×XT Sample Buffer (Bio-Rad) and 1× XT Reducing Agent (Bio-Rad). Whole cell lysates were sonicated using a Bio-rupture (Diagenode) 5 min at high intensity and denatured at 95° C. for 5 min prior to loading on gel. Separation was done on 10% or 4-20% SDS-PAGE gel electrophoresis (Criterion™ TGX™ gels, Bio-Rad). Transfer onto poly-vinylidene difluoride membranes (Bio-Rad) was done using a Trans-Blot®-Turbe transfer system. All western blots were incubated and washed with TBS supplemented with 0.05% Tween-20. The following specific antibodies were used with PVDF membranes blocked in 5% skim-milk (Sigma Aldrich 70166-500G) and 1% skim-milk in antibody solutions: anti-IFI16 (Santa Cruz sc-6050), anti-cGAS (Sigma HPA031700), anti-STING (Cell Signaling #13647) and anti-vinculin (Sigma Aldrich v9131). The following specific antibodies were used with PVDF membranes blocked in 5% BSA (Roche 10 739 086 001) and 1% BSA in antibody solutions: anti-STING S-366 (a gift from Zhijian James Chen, UT southwestern Medical school, Texas), anti-phospho-TBK1 (Cell Signaling #4947s), anti-TBK1 (Cell Signaling cat not), anti-IRF-3 (Cell Signaling #3013), and anti-phospho-IRF3 (Cell Signaling #5483s). Secondary antibodies, peroxidase-conjugated F(ab')2 donkey anti-mouse IgG (H+L), peroxidase-conjugated Affinipure F(ab')2 donkey anti-rabbit IgG (H+L) and peroxidase conjugated F(ab')2 donkey anti-goat IgG (H+L), were purchased from Jackson Immuno Research. IRF3 western blotting was conducted on nuclear fractions according to the manufacturer's instructions (Subcellular Protein Fractionation Kit for Cultured Cells, Thermo Scientific) using anti-IRF3 (Santa Cruz sc-9082). All membranes were exposed using Clarity™ Western ECL Blotting Substrate. The levels of proteins were for some experiments quantified by densitometry (ImageJ) as specified in the figure. To verify phosphorylation events on proteins, whole cell lysates were pre-treated with 10 units of FastAP Thermosensitive Alkaline phosphatase according to manufacturer's protocol (Thermo Scientific).

Semi-Native WB STING Dimerization Assay

STING dimerization was assayed under semi-native conditions. Two hundred thousand cells were lysed in 150 ul Pierce RIPA buffer (Thermo Scientific) supplemented with 10 mM NaF, 1× complete protease cocktail inhibitor (Roche), 1×XT Sample Buffer (Bio-Rad). Whole cell lysates were sonicated using a Bioruputre (Diagenode) 5 min at high intensity prior to loading on gel without heating. Separation was done on 4-20% SDS-PAGE gel electrophoresis (Criterion™ TGX™ gels, Bio-Rad) where each gel was run initially for 10 min at 70V and subsequently for 45 min at 120V. Transfer onto poly-vinylidene difluoride membranes (Bio-Rad) was done using a Trans-Blot®-Turbe transfer system. The blots were incubated and washed with TBS supplemented with 0.05% Tween-20. The following specific antibodies were used on membranes blocked in 5% skim-milk (Sigma Aldrich 70166-500G) and 1% skim-milk antibody solutions: anti-STING (Cell Signaling #13647) and anti-vinculin (Sigma Aldrich v9131). Secondary antibodies, peroxidase-conjugated F(ab")2 donkey anti-mouse IgG (H+L) and peroxidase-conjugated Affinipure F(ab")2 donkey anti-rabbit IgG (H+L). Membranes were exposed using Clarity™ Western ECL Blotting Substrate.

Confocal Microscopy

For visualization of IFI16 following transfection with DNA or cGAMP infusion, 50.000 cells on 1.2 mm coverslips were fixed with 2% PFA for 15 min and permeabilized with 0.2% Triton X-100. Coverslips were stained with antibodies directed against IFI16 (C-18, Santa Cruz sc-6050), STING (R&D Systems, AF6516) or IRF3 (Cell Signaling 4302s). Secondary antibodies included Alexa Fluor 488 Donkey-anti-rabbit, Alexa Fluor 568 Donkey-anti-sheep, and Alexa Fluor 488 Donkey-anti-goat (Molecular probes, A11002, A21099, and A11055, resp). Images were acquired using a Zeiss LSM 710 or LSM 780 confocal microscope using a 63×1.2 water lens. Images were handled using Zen 2011 (Zeiss) and ImageJ.

Co-Immunoprecipitation

Ten million THP-1 macrophages grown in T75 flask with 15 ml medium were transfected with 4 ug/ml dsDNA using lipofectamine. Cells were harvested and resuspended in 500 ul Pierce Co-IP lysis buffer (Thermo Scientific) supplemented with 1× Complete Ultra (Roche) and NaF 10 mM. Cells were allowed to lyse at 4 C for 90 min under rotation and cytosolic supernatants were cleared by centrifugation at 2000×g for 10 min. These lysates were then incubated at 4° C. overnight with 6 ug anti-IFI16 (Santa Cruz sc-6050) or 6 ug anti-STING (Cell Signaling 13647) primary antibodies. On the following day, each lysate was incubated with pre-washed Dynabeads magnetic protein G (Invitrogen), washed four times in Pierce Co-IP lysis buffer and proteins were detached from beads by incubating samples in a pH 2 elution buffer for 10 min on ice. Samples were subsequently neutralized, mixed with SDS-loading buffer and reducing agent, heated and loaded on SDS-page.

Determination of cGAMP by Liquid Chromatography Tandem Mass Spectrometry (LC-MS/MS)

Three million THP-1 cells were seeded in 6-well plates with 3 ml medium and allowed to PMA-differentiate for two days before transfecting with 2 µg/ml dsDNA. Cells were subsequently lyzed in (80% methanol, 2% acetic acid, 18% deionized water). Lysates were spun at 10.000×g for five minutes before collecting supernatant A. The pellet was resuspended in 2% acetic acid and incubated for five minutes on ice before being spun at 10.000×g. Supernatant B was collected and pooled with supernatant A. The previous step was repeated generating supernatant C which was pooled with A+B. Supernatants were added to HyperSep aminopropyl solid phase extraction (SPE) cartridges (Thermo Scientific) for cGAMP purification. The SPE cartridges were conditioned with methanol following deionized water prior to applying supernatants. After supernatant run-through columns were washed in deionized water followed by methanol. cGAMP was eluted in 1.5 ml alkaline methanol (80% methanol+20% concentrated aqueous ammonia (25% $NH_4OH$)). Eluates were evaporated using a vacuum centrifuge and redissolved in 50 µl mobile phase A (0.1% aqueous formic acid).

The liquid chromatography system was a Waters Acquity UPLC system that consisted of a binary pump, a flow-through-needle sample manager thermostated at 5±2° C. and a column oven set at 45±2° C. (Waters). The tandem mass spectrometer was a Waters Xevo TQ-S triple-quadrupole instrument with an electrospray ionization (ESI) source. A volume of 10 µl of the purified cGAMP was injected onto a HSS T3 column (1.8 µm, 200 Å, 2.1 mm I.D.×100 mm) (Waters) running 100% mobile phase A. The mobile phase was changed through a linear gradient to 80% A and 20% B (0.1% FA in acetonitrile) over 5 min. Then, the gradient was changed to 100% B over 0.1 min. Eight minutes after injection, the gradient was returned to 100% A over 0.1 min, and the column was equilibrated for 3.9 min before the next injection, resulting in a total runtime of 12 min. The column flow rate was 400 µl/min. The source and desolvation temperatures were set at 150° C. and 600° C., respectively, and the cone and desolvation nitrogen gas flows were set at 150 l/h and 1000 l/h, respectively. The mass spectrometer was operated in both positive and negative ion modes with a capillary voltage of 2.3 kV and a cone voltage of 30 V. The dominant precursor ions were the double charged molecular ions, m/z 338 in ESI(+) and m/z 336 in ESI(−). Several useful transition products were obtained by collision-induced dissociation using argon as collision gas. The transition products measured in ESI(+) were m/z 152 (obtained by applying a collision energy (CE) of 15 eV), m/z 524 (CE 9 eV) and m/z 136 (CE 22 eV). In ESI(−) m/z 134 (CE 18 eV) and m/z 150 (CE 18 eV) were measured. To achieve semi-quantitative results corresponding blank samples were spiked with cGAMP to a concentration of 10 nM (for single point calibration curves) or concentrations of 0.1, 1, 10, 100, 200, 300 and 400 nM (for 7-point calibration curves). The m/z 152 product ion obtained in ESI(+) was used as the primary quantifier.

siRNA Mediated Knock Down

On days 6 and 8 post isolation, monocyte derived macrophages were transfected with a pool of IFI16 specific siRNAs (#HSS105205,6,7; Life Technologies or #L-020004-00; Dharmacon) or the respective scrambled siRNA controls (45 nM) using Lipofectamine RNAiMax (Life technologies) according to the manufacturer's instructions, followed by infection or stimulation at day nine or day 10 respectively.

Luciferase Assay

HEK293T overexpressing STING cells were seeded in 6-well plates at a density of $5\times10^5$ cells/well and cultured for 24 h. The cells were transiently transfected with a transfection mixture consisting of DNA and the transfection agent polyethylenimine-max (PEI-max) in a ratio of 1:3. For all experiments, the DNA mixture contained 968,5 ng reporter plasmid containing firefly luciferase under the control of the IFN-β promoter, 31,2 ng reporter plasmid containing Renilla luciferase under the control of the β-actin promoter and 1000 ng plasmid DNA of the IFI16-wt, IFI16-PYRIN, IFI16-HIN-A type, cGAS, or eGFP as a control. The DNA and PEI mixtures were mixed and incubated 15 min at room temperature before applied to the cells. Cells were incubated for 18 h and reseeded on 96-well plate coated with poly-L-Lysine (Sigma 3438-100-01) and incubated for 18 hours before infusion with cGAMP or digitonin buffer as a control for 10 min. After incubation media was removed and cells were lyzed (Promega E2920) and luciferase and Renilla signal was measured according to manufactory instructions.

Sequencing.

Genomic DNA was extracted and purified from THP1 KO cells using DNeasy Blood & Tissue Kit (Qiagen) followed by PCR amplification with primers designed to cover an area of 350 nucleotide around the gRNA target sequence in the IFI16 gene. PCR fragments were inserted into the TOPO-TA plasmid following the manufactures procedure. At least 10 individual clones from each gRNA target were evaluated by Sanger sequencing (GATC, Germany).

Statistical Analysis

For analysis of statistically significant differences between multiple groups of data we used unpaired Student t-test for multiple comparisons using Holm-Sidak. For analysis of three groups of data we used one-way ANOVA with Dunnett's multiple comparisons test.

REFERENCES

Ablasser, A. et al. Cell intrinsic immunity spreads to bystander cells via the intercellular transfer of cGAMP. *Nature* 503, 530-534, doi:10.1038/nature12640 (2013).

Diner, B. A. et al. The functional interactome of PYHIN immune regulators reveals IFIX is a sensor of viral DNA. *Mol Syst Biol* 11, 787, doi:10.15252/msb.20145808 (2015).

Holm, C. K. et al. Influenza A virus targets a cGAS-independent STING pathway that controls enveloped RNA viruses. *Nature communications* 7, 10680, doi: 10.1038/ncomms10680 (2016).

Jakobsen, M. R. et al. IFI16 senses DNA forms of the lentiviral replication cycle and controls HIV-1 replication. *Proceedings of the National Academy of Sciences of the United States of America* 110, E4571-4580, doi:10.1073/pnas.1311669110 (2013).

Jin, T. et al. Structures of the HIN domain:DNA complexes reveal ligand binding and activation mechanisms of the AIM2 inflammasome and IFI16 receptor. *Immunity* 36, 561-571, doi:10.1016/j.immuni.2012.02.014 (2012).

Liu, S. et al. Phosphorylation of innate immune adaptor proteins MAVS, STING, and TRIF induces IRF3 activation. *Science* 347, aaa2630, doi:10.1126/science.aaa2630 (2015).

Unterholzner, L. et al. IFI16 is an innate immune sensor for intracellular DNA. *Nature immunology* 11, 997-1004, doi:10.1038/ni.1932 (2010).

van de Weijer, M. L. et al. A high-coverage shRNA screen identifies TMEM129 as an E3 ligase involved in ER-associated protein degradation. *Nature communications* 5, 3832, doi:10.1038/ncomms4832 (2014).

Example 2

The example illustrate that a method designed to produce virus-like particles comprising cGAMP can be significantly improved by the co-expression of IFI16 in the producer cells.

Results

Figure 23:
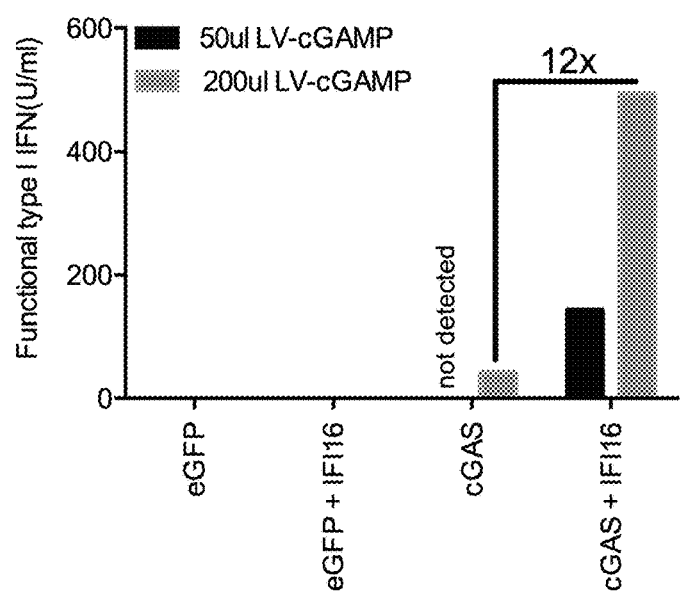

Recently, it has been demonstrated that production of HIV-1-based lentiviral particles by plasmid transfection in HEK293T cells that co-expresses cGAS, allows the generation of cGAMP by cGAS sensing plasmid DNA. The produced cGAMP is then packed into newly generated lentiviral particles budding of the HEK293T cells (REFs). These particles psuedotyped with the surface receptor of VSVg are immunostimulatory, as they deliver cGAMP to target cells that activates STING (FIG. 22). Bases on our recent data (see FIG. 5e) we speculated that the production of lentiviral particles carrying cGAMP could be improved by co-expression of IFI16, as it synergistic enhances the function of cGAS. We generated HEK293T-IFI16 stable expressing cells (FIG. 5d) and transfected them with plasmid expressing cGAS, VSVg and the gag/pol fraction of HIV-1 (FIG. 22). Seventy-two hours later supernatants were harvests and used to stimulate PMA-differentiated THP1 cells. Viral particles produced in HEK293T and HEK293T-IFI16 cells co-expressing eGFP did not show any immunostimulatory effects, measured by THP1 cells capacity to secrete type I interferon (FIG. 23). Lentiviral particles produced in HEK293T cells co-expressing cGAS has very low immunostimulatory effects, whereas from HEK293T-IFI16 cells the particles generated a significant 12-fold increased type I interferon production (FIG. 23 grey bars), and even a low dosis of particles were able to produce strong immunostimulatory signals (FIG. 23 black bars).

To conclude, producer cells that express IFI16 in combination with cGAS are superior to generate virus-like particles with cGAMP as immunostimulatory adjuvants compared to prior practise where IFI16 has been excluded.

Methods

Cell Culture.

Human acute monocytic leukemia cell line (THP-1) was cultured in RPMI 1640 (Lonza) supplemented with 10% heat inactivated fetal calf serum, 200 IU/mL Penicillin, 100 μg/mL Streptomycin and 600 μg/mL glutamine (hereafter termed RPMI complete). Mycoplasma infection was tested and ruled on a monthly basis using Lonza MycoAlert kit (LT07-703). To differentiate THP-1 cells into adherent phenotypically macrophages, cells were stimulated with 100 nM Phorbol 12-myristate 13-acetate (PMA, Sigma Aldrich 79346 5MG) in RPMI complete for 24 hours before medium was refreshed with normal RPMI complete and allowed to further differentiate an additional day (hereafter defined as macrophages). Of note, the haplotype of STING in the THP-1 parental cell type has been identified to be HAQ.

HEK293T cells were cultured in Dulbecco's Modified Eagle Medium (DMEM) supplemented with 10% heat inactivated FCS; 200 IU/mL Penicillin; 100 μg/mL Streptomycin and 600 μg/mL glutamine. HEK-Blue™ IFN-α/β (InvivoGen) cells were cultured in DMEM supplemented with 10% heat inactivated FCS; 200 IU/mL Penicillin, 100 μg/mL Streptomycin, 600 μg/mL glutamine, 100 μg/mL normocin (InvivoGen), 30 μg/mL blasticidin (InvivoGen) and 100 μg/mL zeocin (InvivoGen).

Cells

Human Embryonic Kidney 293T (HEK293T) cells were stably transfected with wild type human IFI16 using the sleeping beauty-mediated transposition system. Human IFI16 and SB100X encoding vectors were mixed with Polyethyleneimine in a 1:3 relationship and administered to the cells which were allowed to incubate for 48-hours. Cells were subsequently selected with 1 μg ml$^{-1}$ puromycin for two weeks and allowed to expand before analyzing stable expression of IFI16 via western blotting.

Production of VLP-cGAMP

HEK293T and HEK293T overexpressing IFI16 cells were seeded in 6-well plates at a density of 5×10$^5$ cells/well and cultured for 24 h. VSVg-pseudotyped virus-like particles (e.g. VLPs) were generated by transfecting HEK293T cells −/+IFI16 with the plasmid pMD.2G; SIV4+ and mBanana-cGAS fusion in a ratio of 1-2-1 using the transfection agent polyethylenimine-max (PEI-max). Supernatants were harvested after 48 hours and filtrated through 20 um sterile membranes, aliquated in small volumes and stored at −80° C.

VLP-cGAMP Stimulation and of Cells

Two-hundred thousand PMA-differentiated THP-1 cells in 48-well plates were stimulated with increasing volume of the inoculum of VLPs produced in HEK293T and HEK293T-IFI16 cells. Twenty hours later supernatants were harvest for functional type I IFN measurements.

To quantify functional type I IFN the reporter cell line HEK-Blue™ IFN-α/β (InvivoGen) was utilized according to the manufacturers instructions. Thirty thousand HEK-Blue cells were seeded in a 96-well plates with 150 μl medium devoid of Blasticidin and Zeocin and given 50 μl supernatant the next day. This cell line expresses secreted embryonic alkaline phosphatase under the control of the IFN-α/β inducible ISG54 promotor. SEAP activity was assessed by measuring optical density (OD) at 620 nm on a micro plate reader (ELx808, BioTEK). The standard range was made with IFN-α (A2) (PBL Assay Science).

Example 3

Experiment 1: Uptake in HEK293T Cells

Each peptide was diluted in water and added to HEK293T cells with increasing doses. After 20 hrs cells were washed 3× times and then lysed for immunoblotting with anti-biotin.

Results demonstrate that all peptides are capable of penetrating cells at different degrees; cf. FIG. 24

Experiment 2: Uptake in Human PBMCs

Each peptide was diluted in water and added to a culture of human PBMCs at a final concentration of 5 ug/ml. After 20 hrs cells were washed and lysed for immunoblotting using anti-biotin.

Results demonstrate that all peptides are able to penetrate PBMCs at variable levels; cf. FIG. 25.

Experiment 3a: Uptake in Human PBMCs—Time Kinetics

Each peptid was diluted in water and added to a culture of human PBMCs at a final concentration of 5 ug/ml. After 1, 2, and 4 hrs cells were washed and lysed for immunoblotting using anti-biotin.

Results demonstrate that some peptides had faster uptake and stable expression within the PBMC culture; cf. FIG. 26.

Experiment 3b: Stimulation of PBMCs with DNA in Combination with Peptides

Each peptid was diluted in water and added to a culture of human PBMCs at a final concentration of 5 ug/ml. After 1, 2, and 4 hrs cells were washed and stimulated with DNA (activates cGAS to produce cGAMP that stimulate STING and lead to IFN secretion).

FIG. 27: Results demonstrate that PBMCs stimulated with DNA gave a robust IFN signal but in combination with most peptides this response increase even further. Also, this increased response was dependent on the kinetic of peptide uptake. Furthermore, peptides alone did not lead to any IFN response.

Experiment 4: Stimulation of Macrophages (PMA-Differentiated THP1 Cells) with Peptides Each peptid was diluted in water and added to a culture of macrophages at a final concentration of 5 ug/ml. After 1, 4,6 and 20 hrs cells were washed and lysed for immunoblotting of STING, pTKB1 and Biotin FIG. 28: Results demonstrate that most peptides are degraded within cells after 20 hrs but also that some peptides lead to a preactivated form of STING (e.g. dimerization of STING=$STING_D$). None of the peptides lead to phosphorylation of TBK1, supporting that peptides alone do not trigger IFN responses.

Experiment 5: Stimulation of Macrophages (PMA-Differentiated THP1 Cells) with Peptides and cGAMP Each peptid was diluted in water and added to a culture of macrophages at a final concentration of 5 ug/ml. After 1, 4, and 6 hrs cells were washed and stimulated with cGAMP infusion.

FIG. 29: Results demonstrate that some peptides had superior effects on cGAMP stimulation of up to 3 fold enhanced IFN responses compared to cells without peptides.

Experiment 6: Stimulation of Murine Macrophages with Peptides and cGAMP

Each peptid was diluted in water and added to a culture of murine macrophages at a final concentration of 5 ug/ml. After 6 hrs cells were washed and stimulated with cGAMP infusion. After 20 hrs supernatants were harvest and cell lysed for immunoblotting.

FIG. 30: Results demonstrate that some peptides had poor stability in the murine macrophage model. However all peptides demonstrated superior enhanced immune responses in combination with cGAMP—measured by CXCL10 secretion.

Experiment 7: Stimulation of Human Primary Macrophages with Peptides and cGAMP or HT-DNA Costimulation Each peptide was diluted in water and added to a culture of primary human macrophages generated from a donor monocyte population at a final concentration of 5 ug/ml. After 1 hour cells were washed and stimulated with increasing doses of cGAMP (0.25 uM, 0.5 uM or 1 uM) or HT-DNA (0.2 ug/ml, 0.4 ug/ml, 0.8 ug/ml) formulated with lipofectamine2000. After 6 hours supernatants were collected and evaluated for type I IFN and CXCL10 secretion by bioassay and ELISA, respectively.

FIG. 31: Results demonstrate that peptides has superior effects on stimulating STING upon activation with either cGAMP or HT-DNA.

Experiment 8: Stimulation of Human Primary Macrophages with Peptide S1 with or without Biotin and HIV-Tat Cell Penetrating Motif Peptide S1 was synthesised with (S1(SEQ ID NO: 15)) or without biotin (—B) (SEQ ID NO: 25) or HIV-tat (-T) (SEQ ID NO: 26). Each peptide were diluted in water and added to a culture of primary human macrophages generated from a donor monocyte population at a final concentration of 5 ug/ml. After 1 hour cells were washed and stimulated with HT-DNA (0.4 ug/ml) formulated with lipofectamine2000. After 6 hours supernatants were collected and evaluated for type I IFN and CXCL10 secretion by bioassay and ELISA, respectively FIG. 32: Results demonstrate that a peptide without biotin comprise similar functionality as peptides with biotin. However, a peptide lacking a cell penetrating motif have decreased effects to induce CXCL10 expression.

Experiment 9: In Vivo Stimulation with Peptides

Each peptide with (+) or without (−) cell penetrating peptide (CPP) was diluted in physiological salt water and subcutaneously injected into the flank of C57BL/6J mice at a dose of 20 ug/mice. After 6 hours, each mice was killed and skin at injection site was surgical removed. Tissue was then homogenised and used to extract genomic RNA. Quantitative RT-PCR was used to evaluate the gene expression of IFNb, CXCL10 and the early interferon regulated gene IFIT2.

FIG. 33: Results demonstrate that peptides with and without CPP is able to induce a strong immune response in vivo.

Items

Particularly preferred, however, nonlimiting embodiments of the present invention are described in the items set forth below.

1. A compound capable of binding to the pyrin-domain of IFI16 or a fragment thereof for use in the treatment of a disorder associated with STING activity.
2. The compound according to item 1, wherein the compound is capable of binding a polypeptide comprising or consisting of
a. the pyrin-domain of human IFI16 (human pyrin-domain) provided herein as SEQ ID NO:1
b. a fragment of said human pyrin-domain consisting of a consecutive sequence of at least 5 amino acids of SEQ ID NO:1
c. a functional homologue of the human pyrin-domain sharing at least 70% sequence identity with SEQ ID NO:1.
3. The compound according to any one of the preceding items, wherein said compound is capable of inhibiting interaction between IFI16 and TBK1.
4. The compound according to any one of the preceding items, wherein said compound is capable of inhibiting interaction between TBK1 and STING
5. The compound according to any one of the preceding items, wherein said compound is capable of inhibiting interaction between IFI16 and STING.

6. The compound according to any one of the preceding items, wherein said compound is capable of inhibiting STING activation.

7. The compound according to any one of the preceding items, wherein said compound is capable of inhibiting STING phosphorylation.

8. The compound according to any one of the preceding items, wherein said compound is a peptide.

9. The compound according to any one of the preceding items, wherein said compound is a small molecule interacting with the Pyrin-domain of IFI16.

10. The compound according to any one of the preceding items, wherein the compound is an antibody, an antigen-binding fragment of an antibody or a synthetic antibody specifically binding the pyrin-domain of IFI16 or a fragment thereof.

11. A method of treating a disorder associated with STING activity comprising administering a compound capable of binding to the pyrin-domain of IFI16 or a fragment thereof to an individual in need thereof.

12. The method according to item 11, wherein the compound is the compound according to any one of items 1 to 10.

13. Use of a compound capable of binding to the pyrin-domain of IFI16 or a fragment thereof for the preparation of a medicament for the treatment of a disorder associated with STING activity.

14. Use according to item 13, wherein the compound is the compound according to any one of items 1 to 10.

15. The compound, method or use according to any one of the preceding items, wherein said disorder is associated with TBK1 activity.

16. The compound, method or use according to any one of the preceding items, wherein the disorder associated with STING activity is an inflammatory disorder, for example psoriasis, Crohn's disease, Inflammatory bowel disease (IBD).

17. The compound, method or use according to any one of the preceding items, wherein the disorder associated with STING activity is an auto-immune disease, for example systemic lupus erythematosus (SLE), Aicardi-Goutieres syndrome, Sjogren's syndrome, Type 1 diabetes and multiple sclerosis.

18. The compound, method or use according to any one of the preceding items, wherein the disorder associated with STING activity is cancer, for example a cancer induced by chronic inflammatory signalling.

19. The compound, method or use according to any one of the preceding items, wherein the cancer is a cutaneous skin tumour, for example basal cell (BCC) or squamous cell carcinoma (SCC).

20. A method of identifying a compound capable of binding the pyrin-domain of IFI16, said method comprising the steps of
a) providing a pyrin-domain of IFI16 or a fragment thereof
b) providing a library of test compounds
c) contacting the pyrin-domain of IFI16 with said test compounds
d) detecting and isolating test compounds, which interact with the pyrin-domain of IFI16 or the fragment thereof
thereby identifying an anti-inflammatory agent.

21. The method according to item 20, wherein the test compounds are selected from the group consisting of peptides, small organic molecules, antibodies, antigen binding fragments of antibodies and synthetic antibodies.

22. The method according to any one of items 20 to 21, wherein the method further comprising the step of detecting and isolating test compounds, which inhibit interaction between IFI16 and TBK1, and/or inhibit interaction between IFI16 and STING.

23. A compound capable of mimicking the pyrin-domain of IFI16, thereby inducing STING activity.

24. A polypeptide comprising or consisting of the pyrin-domain of IFI16 or a fragment thereof, wherein the polypeptide optionally may be linked to at least one conjugated moiety.

25. The polypeptide according to item 24, wherein the polypeptide comprises or consists of
a. the pyrin-domain of human IFI16 (human pyrin-domain) provided herein as SEQ ID NO:1;
b. a fragment of said human pyrin-domain consisting of a consecutive sequence of at least 5 amino acids of SEQ ID NO:1; or
c. a functional homologue of the human pyrin-domain sharing at least 70% sequence identity with SEQ ID NO:1.

26. The compound or polypeptide according to any one of items 23 to 25, wherein said compound or polypeptide is capable of interacting with TBK1 and/or STING.

27. The compound or polypeptide according to any one of items 23 to 26, wherein said compound or polypeptide is capable of inducing phosphorylation of STING at Ser366.

28. The compound or polypeptide according to any one of items 23 to 27, wherein said compound or polypeptide is capable of inducing STING activation.

29. The method according to any one of items 20 to 22, wherein the pyrin-domain of IFI16 or a fragment thereof is the polypeptide according to any one of items 24 to 28.

30. A method of identifying a compound capable of mimicking the pyrin-domain of IFI16, said method comprising the steps of
a) providing a library of test compounds
b) testing whether said test compounds are capable of inducing STING activity
thereby identifying a compound capable of mimicking IFI16.

31. A compound or polypeptide according to any one of items 23 to 28 for use in the treatment of a disorder associated with insufficient STING activity.

32. A method of treating a disorder associated with insufficient STING activity comprising administering the compound or the polypeptide according to any one of items 23 to 28 to an individual in need thereof.

33. Use of the compound or the polypeptide according to any one of items 23 to 28 for the preparation of a medicament for the treatment of a disorder associated with insufficient STING activity.

34. The polypeptide, the method or the use according to any one of items 31 to 33, wherein said disorder is cancer.

35. The polypeptide, the method or the use according to any one of items 31 to 33, wherein said disorder is an infection with a DNA pathogen, for example malaria or listeria.

36. The compound, the method, the use or the polypeptide according to any one of items 1 to 19 and 31 to 35, wherein said treatment of said disorder further comprises administration of one or more additional active compounds.

37. The compound, the method, the use or the polypeptide according to item 36, wherein the additional active compound is an anti-cancer agent.

38. A method of producing viral particles comprising cGAMP, wherein the virus-like particles are produced in cells that stably overexpress IFI16 protein.

39. A virus-like particle comprising cGAMP obtainable by the method of item 38.

40. A method of treating an auto-immune or inflammatory disorder comprising administering virus-like particle comprising cGAMP obtainable by the method of item 38.

41. A virus-like particle comprising cGAMP obtainable by the method of item 38 for use in medicine, such as for use as a vaccine adjuvant and/or for treatment of an auto- immune or inflammatory disorder or an infectious disease or any disorder associated with STING activity.

42. A recombinant eukaryotic host cell comprising a sequence encoding a cGAS (Cyclic GMP-AMP synthase) and a sequence encoding a viral fusogenic glycoprotein and a sequence encoding Interferon-gamma-inducible protein 16 (IFI16).

The invention claimed is:

1. A method of treating a disorder associated with insufficient stimulator of interferon genes (STING) activity comprising administering to an individual in need thereof a polypeptide having at least 80% sequence identity with a polypeptide selected from the group consisting of SEQ ID NOs: 5-28 to treat a disorder associated with insufficient STING activity, wherein the disorder is cancer or infection.

2. The method of claim 1, wherein the polypeptide has at least 85% sequence identity with a polypeptide selected from the group consisting of SEQ ID NOs: 5-28.

3. The method according to claim 1, wherein said compound is capable of inducing STING activity.

4. The method according to claim 1, wherein said polypeptide is conjugated to a cell penetrating peptide.

5. The method according to claim 1, wherein said treatment comprises administration of one or more additional active compounds.

6. The method of claim 1, wherein said polypeptide induces phosphorylation of STING at $Ser^{366}$.

7. The method according to claim 1, wherein said infection is malaria or listeria.

8. A method of treating a disorder associated with insufficient stimulator of interferon genes (STING) activity comprising administering to an individual in need thereof a polypeptide wherein said polypeptide is SEQ ID NO: 5 and/or SEQ ID NO: 11.

* * * * *